United States Patent
Frendéus et al.

(10) Patent No.: US 12,139,547 B2
(45) Date of Patent: Nov. 12, 2024

(54) AGONISTIC ANTI TNFR2 ANTIBODY MOLECULES

(71) Applicant: BIOINVENT INTERNATIONAL AB, Lund (SE)

(72) Inventors: Björn Frendéus, Lund (SE); Ingrid Teige, Lund (SE); Linda Mårtensson, Bjärred (SE); Petra Holmkvist, Kävlinge (SE); Monika Semmrich, Malmö (SE)

(73) Assignee: BIOINVENT INTERNATIONAL AB, Lund (SE)

( * ) Notice: Subject to any disclaimer, the term of this patent is extended or adjusted under 35 U.S.C. 154(b) by 688 days.

(21) Appl. No.: 17/290,340

(22) PCT Filed: Nov. 1, 2019

(86) PCT No.: PCT/EP2019/080003
§ 371 (c)(1),
(2) Date: Apr. 30, 2021

(87) PCT Pub. No.: WO2020/089473
PCT Pub. Date: May 7, 2020

(65) Prior Publication Data
US 2022/0002426 A1  Jan. 6, 2022

(30) Foreign Application Priority Data

Nov. 1, 2018 (EP) .................................... 18203996

(51) Int. Cl.
*A61P 35/00* (2006.01)
*A61K 39/395* (2006.01)
*A61K 45/06* (2006.01)
*C07K 16/28* (2006.01)
*A61K 39/00* (2006.01)

(52) U.S. Cl.
CPC ...... *C07K 16/2878* (2013.01); *A61K 39/3955* (2013.01); *A61K 45/06* (2013.01); *A61P 35/00* (2018.01); *C07K 16/2818* (2013.01); *C07K 16/283* (2013.01); *A61K 2039/505* (2013.01); *A61K 2039/507* (2013.01); *C07K 2317/21* (2013.01); *C07K 2317/31* (2013.01); *C07K 2317/33* (2013.01); *C07K 2317/565* (2013.01); *C07K 2317/75* (2013.01); *C07K 2317/92* (2013.01)

(58) Field of Classification Search
CPC .................................................. C07K 16/2878
USPC ..................................................... 424/136.1
See application file for complete search history.

(56) References Cited

U.S. PATENT DOCUMENTS 5,693,762 A * 12/1997 Queen .................. C07K 16/087
424/143.1

FOREIGN PATENT DOCUMENTS

| WO | 2004/003164 A2 † | 1/2004 |
|---|---|---|
| WO | WO 2014/124134 | 8/2014 |
| WO | WO 2016/187068 | 11/2016 |
| WO | WO 2017/040312 | 3/2017 |
| WO | WO 2017/040312 A1 | 3/2017 |
| WO | WO 2017/083525 | 5/2017 |
| WO | WO 2017/197331 | 11/2017 |

OTHER PUBLICATIONS

Wang et al (Biochemical and Biophys Research Comm, 2017, 487: 1-7).*
Ebert et al (Immunity, 2016, 44: 609-621).*
Casset et al. (Biochemical and Biophysical Research Communications, 2003, 307:198-205).*
Shin et al (Molecular Therapy, 2013, 21(3): 688-695).*
Rudikoff et al. (Proceedings of the National Academy of Sciences, 1982, 79:1979-1983).*
"PE hamster anti-mouse CD120b" Technical data sheet (2017).
Ait-Ali D et al., Tumor Necrosis Factor (TNF)-a Persistently Activates Nuclear Factor-B Signaling through the Type 2 TNF Receptor in Chromaffin Cells: Implications for LongTerm Regulation of Neuropeptide Gene Expression in Inflammation Endocrinology. 2008, 149(6):2840-52.
Almishri W.et al. TNFα Augments Cytokine-Induced NK Cell IFNγ Production through TNFR2. J Innate Immun. 2016;8:617-629.
Amrani et al. Activation of the TNF alpha-p55 receptor induces myocyte proliferation and modulates agonist-evoked calcium transients in cultured human tracheal smooth muscle cells. 1996. Am. J. Respir. Cell. Mol. Biol. 15:55-63.
Bianchi, Elisabetta, et al. "High level expression and rational mutagenesis of a designed protein, the minibody: from an insoluble to a soluble molecule." *Journal of Molecular Biology* 236.2 (1994): 649-659.
Binyamin, L., et al.(2008). Blocking NK cell inhibitory self-recognition promotes antibody-dependent cellular cytotoxicity in a model of anti-lymphoma therapy. Journal of immunology 180, 6392-6401.
Bommareddy. et al 2018. 'Integrating oncolytic viruses in combination cancer immuno-therapy', Nat Rev Immunol, 18: 498-513.
Buchan et al., "Antibodies to Costimulatory Receptor 4-1BB Enhance Anti-tumor Immunity via T Regulatory Cell Depletion and Promotion of CD8 T Cell Effector Function", Immunity 2018 49(5):958-970.
Chan et al. 2014. 'Oncolytic Poxviruses', Annu Rev Virol, 1: 119-41.
Chen et al., TNFR2 expression by CD4 effector T cells is required to induce full-fledged experimental colitis. Sci Rep. Sep. 7, 2016;6:32834.
Chu et al. "Inhibition of B cell receptor-mediated activation of primary human B cells by coengagement of CD19 and FcgammaRIIb with Fc-engineered antibodies." Mol Immunol. Sep. 2008;45(15):3926-33.

(Continued)

*Primary Examiner* — Sean E Aeder
(74) *Attorney, Agent, or Firm* — Parker Highlander PLLC

(57) ABSTRACT

Described are novel antibody molecules that specifically bind to TNFR2 on a target cell and thereby agonize TNFR2, but that do not block the ligand TNF-α from binding to the TNFR2. Also described is the use of such antibody molecules in medicine, i.a, in treatment of cancer or chronic inflammatory diseases.

29 Claims, 34 Drawing Sheets
Specification includes a Sequence Listing.

(56) References Cited

OTHER PUBLICATIONS

Dahan et al. 2016. 'Therapeutic Activity of Agonistic, Human Anti-CD40 Monoclonal Anti-bodies Requires Selective FcgammaR Engagement', Cancer Cell, 29: 820-31.

Faustman DL et al., TNF Receptor 2 and Disease: Autoimmunity and Regenerative Medicine, Front Immunol. 2013; 4: 478.

Galloway, Cynthia J., et al. "Anti-tumor necrosis factor receptor and tumor necrosis factor agonist activity by an anti-idiotypic antibody." *European Journal of Immunology* 22.11 (1992): 3045-3048.

Gao, Qing-Sheng, et al. "Molecular cloning of a proteolytic antibody light chain." *Journal of Biological Chemistry* 269.51 (1994): 32389-32393.

Heap, Caroline J., et al. "Analysis of a 17-amino acid residue, virus-neutralizing microantibody." *Journal of general virology* 86.6 (2005): 1791-1800.

Jacobsen, Frederick W., et al. "Engineering an IgG scaffold lacking effector function with optimized developability." *Journal of Biological Chemistry* 292.5 (2017): 1865-1875.

K.C. Sheehan et al., "Monoclonal antibodies specific for murine p55 and p75 tumor necrosis factor receptors: identification of a novel in vivo role for p75". J Exp Med 1995 607-617.

Kampan et al., Interleukin 6 Present in Inflammatory Ascites from Advanced Epithelial Ovarian Cancer Patients Promotes Tumor Necrosis Factor Receptor 2-Expressing Regulatory T Cells; Frontiers in Immunology. 2017, vol. 8:1482.

Kleinpeter et al. 2016. 'Vectorization in an oncolytic vaccinia virus of an antibody, a Fab and a scFv against programmed cell death −1 (PD-1) allows their intratumoral delivery and an improved tumor-growth inhibition', Oncoimmunology, 5: e1220467.

Ladner, Robert Charles. "Antibodies cut down to size." *Nature Biotechnology* 25.8 (2007): 875-877.

Laune, Daniel, et al. "Systematic exploration of the antigen binding activity of synthetic peptides isolated from the variable regions of immunoglobulins." *Journal of Biological Chemistry* 272.49 (1997): 30937-30944.

Lazar et al. 2006. 'Engineered antibody Fc variants with enhanced effector function', Proc Natl Acad Sci U S A, 103: 4005-10.

Li et al. 2011. 'Inhibitory Fcγ gamma receptor engagement drives adjuvant and anti-tumor activities of agonistic CD40 antibodies', Science, 333: 1030-4.

Liu et al. "NF-κB signaling in inflammation". Signal Transduct Target Ther. 2017;2. pii: 17023.

Madsen et al., Oligodendroglial TNFR2 Mediates Membrane TNF-Dependent Repair in Experimental Autoimmune Encephalomyelitis by Promoting Oligodendrocyte Differentiation and Remyelination. J Neurosci. May 4, 2016;36(18):5128-43.

Marabelle, A., et al. 2013, J Clin Invest 123(6):2447-2463.

Marino et al. 2017. 'Development of a versatile oncolytic virus platform for local intra-tumoural expression of therapeutic transgenes', PLoS One, 12: e0177810.

Mimoto et al. "Engineered antibody Fc variant with selectively enhanced FcγRIIb binding over both FcγRIIaR131 and FcγRIIaH131". Protein Eng Des Sel. Oct. 2013; 26(10): 589-598.

Monnet, Céline, et al. "Synthetic peptides derived from the variable regions of an anti-CD4 monoclonal antibody bind to CD4 and inhibit HIV-1 promoter activation in virus-infected cells." *Journal of Biological Chemistry* 274.6 (1999): 3789-3796.

Nicaise, Magali, et al. "Affinity transfer by CDR grafting on a nonimmunoglobulin scaffold." *Protein Science* 13.7 (2004): 1882-1891.

Nimmerjahn, Falk, and Jeffrey V. Ravetch. "Divergent immunoglobulin g subclass activity through selective Fc receptor binding." *Science* 310.5753 (2005): 1510-1512.

Okubo et al., Treg activation defect in type 1 diabetes: correction with TNFR2 agonism. Clin Transl Immunology. Jan. 8, 2016;5(1).

Pessi, Antonello, et al. "A designed metal-binding protein with a novel fold." *Nature* 362.6418 (1993): 367-369.

Qiu, Xiao-Qing, et al. "Small antibody mimetics comprising two complementarity-determining regions and a framework region for tumor targeting." *Nature Biotechnology* 25.8 (2007): 921-929.

Quiocho, F. A. "Making of the minibody." *Nature* 362.6418 (1993): 293-294.

Richards et al. 2008. 'Optimization of antibody binding to Fcg ammaRIIa enhances macrophage phagocytosis of tumor cells', Mol Cancer Ther, 7: 2517-27.

Richman et al. 2014. 'Anti-human CD40 monoclonal antibody therapy is potent without FcR crosslinking', Oncoimmunology, 3: e28610.

Sharabi et al. "Regulatory T cells in the treatment of disease". Nat Rev Drug Discov. Oct. 12, 2018.

Smith, Diana M., et al. "Enhanced synthesis of tumor necrosis factor-inducible proteins, plasminogen activator inhibitor-2, manganese superoxide dismutase, and protein 28/5.6, is selectively triggered by the 55-kDa tumor necrosis factor receptor in human melanoma cells." *Journal of Biological Chemistry* 269.13 (1994): 9898-9905.

Söderlind, Eskil, et al. "Recombining germline-derived CDR sequences for creating diverse single-framework antibody libraries." *Nature Biotechnology* 18.8 (2000): 852-856.

Stypulowski et al., The depalmitoylase APT1 directs the asymmetric partitioning of Notch and Wnt signaling during cell division. Sci Signal. 2018; 11(511).

Tartaglia, L. A., et al. "Stimulation of human T-cell proliferation by specific activation of the 75-kDa tumor necrosis factor receptor." *The Journal of Immunology* 151.9 (1993): 4637-4641.

Tartaglia, Louis A., Diane Pennica, and D. V. Goeddel. "Ligand passing: the 75-kDa tumor necrosis factor (TNF) receptor recruits TNF for signaling by the 55-kDa TNF receptor." *Journal of Biological Chemistry* 268.25 (1993): 18542-18548.

Tato et al. "Opposing roles of NF-kappaB family members in the regulation of NK cell proliferation and production of IFN-gamma". Int Immunol. Apr. 2006;18(4):505-13.

Thommesen et al. "Distinct differences between TNF receptor 1- and TNF receptor 2-mediated activation of NFkappaB". J Biochem Mol Biol. May 31, 2005;38(3):281-9.

Vanamee ES et al., TNFR2: A Novel Target for Cancer Immunotherapy, Trends in Molecular Medicine, 2017, vol. 23, issue 11, 1037-1046.

Vaughan & Sollazzo 2001, Combinatorial Chemistry & High Throughput Screening, 4: 417-430.

Vessillier, S., et al. "Cytokine release assays for the prediction of therapeutic mAb safety in first-in man trials—Whole blood cytokine release assays are poorly predictive for TGN1412 cytokine storm." *Journal of Immunological Methods* 424 (2015): 43-52.

White et al. 2011. 'Interaction with Fc gammaRIIB is critical for the agonistic activity of anti-CD40 monoclonal anti-body', J Immunol, 187: 1754-63.

White et al. 2014. 'Fcgamma receptor dependency of agonistic CD40 antibody in lympho-ma therapy can be overcome through antibody multimerization', J Immunol, 193: 1828-35.

Williams GS et al, Phenotypic screening reveals TNFR2 as a promising target for cancer immunotherapy, Oncotarget. 2016; 7(42): 68278-68291.

Yang et al. "Role of TNF-TNF Receptor 2 Signal in Regulatory T Cells and Its Therapeutic Implications". Front Immunol. Apr. 19, 2018;9:784.

Ando, D. et al., "Creation of mouse TNFR2-selective agonistic TNF mutants using a phage display technique," *Biochemistry and Biophysics Reports*, 7 (2016): 309-315.

Badri, H. et al., "Optimization of radiation dosing schedules for proneural glioblastoma," *Journal of Mathematical Biology*, 72 (2016): 1301-1336, abstract only.

Baylot, V. et al., "TCTP Has a Crucial Role in the Different Stages of Prostate Cancer Malignant Progression," *TCTP/tpt1—Remodeling Signaling from Stem Cell to Disease*, 64 (2017): 255-261, abstract only.

He, X. et al., "A TNFR2-Agonist Facilitates High Purity Expansion of Human Low Purity Treg Cells," *PLOS One*, 11 (2016): 1-17.

Zou, H. et al., "Modulation of Regulatory T Cell Activity by TnF Receptor Type ii-Targeting Pharmacological Agents," *Frontiers in Immunology*, 9 (2018): 1-10.

(56) References Cited

OTHER PUBLICATIONS

Nakayama, S. et al., "TNF-α Receptor 1 Expression Predicts Poor Prognosis of Diffuse Large B-cell Lymphoma, Not otherwise specified," *The American Journal of Surgical Pathology*, 38.8 (2014): 1138-1146, abstract.
Office Action issued in European Patent Application No. 19805900.8, dated May 5, 2024.
Barnhart et al., Immunol. Cell Biol. 95(4): 340-346, 2017.†
Vanamee et al., Trends Mol. Med. 23(11): 1037-1046, 2017.†
Torrey et al., Leukemia. 33(5): 1206-1218, 2019.†
Faustman, Diabetes Metab. Res. Rev. 34(1), 2018.†

\* cited by examiner
† cited by third party

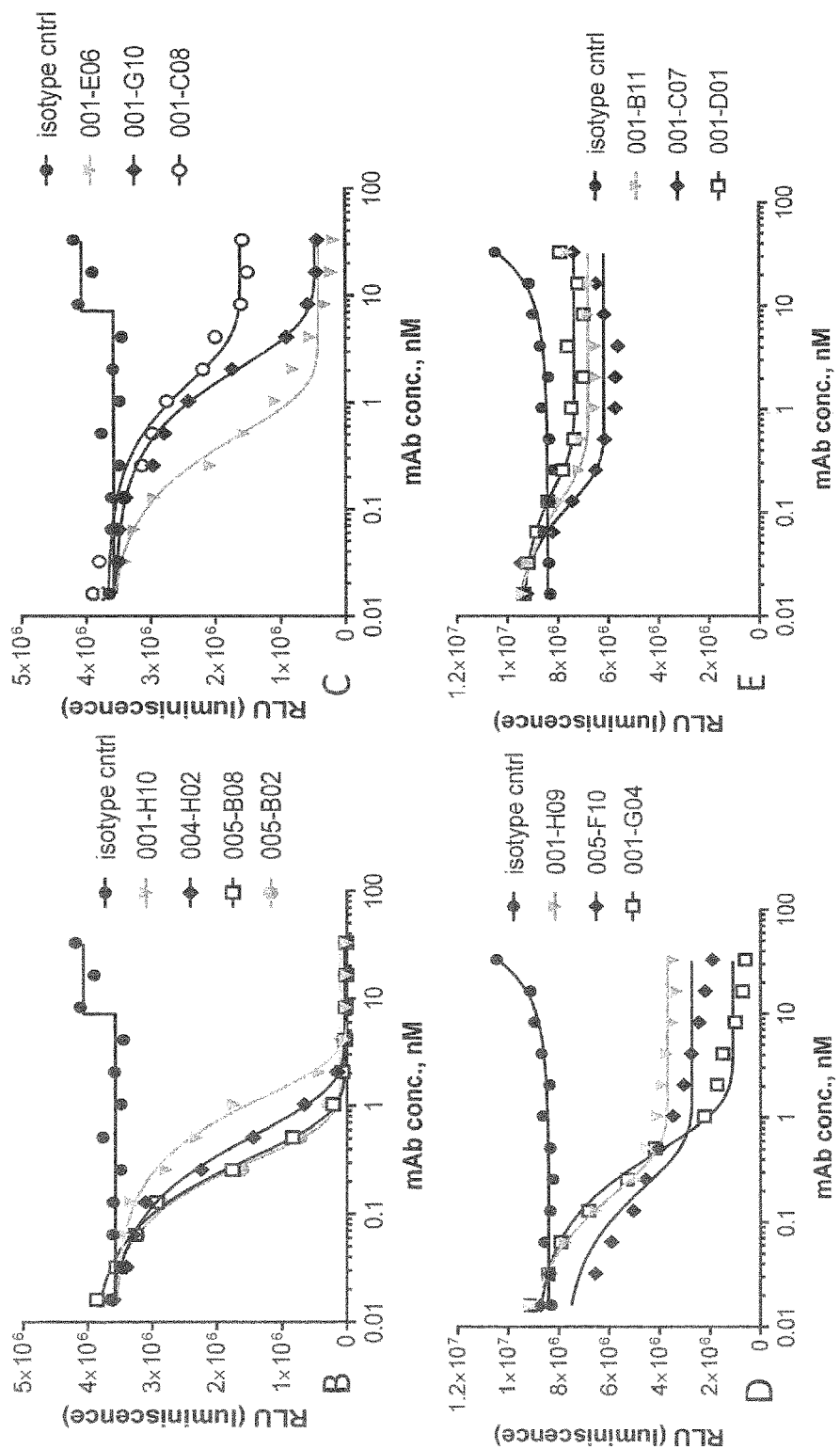
Fig. 6, cont.

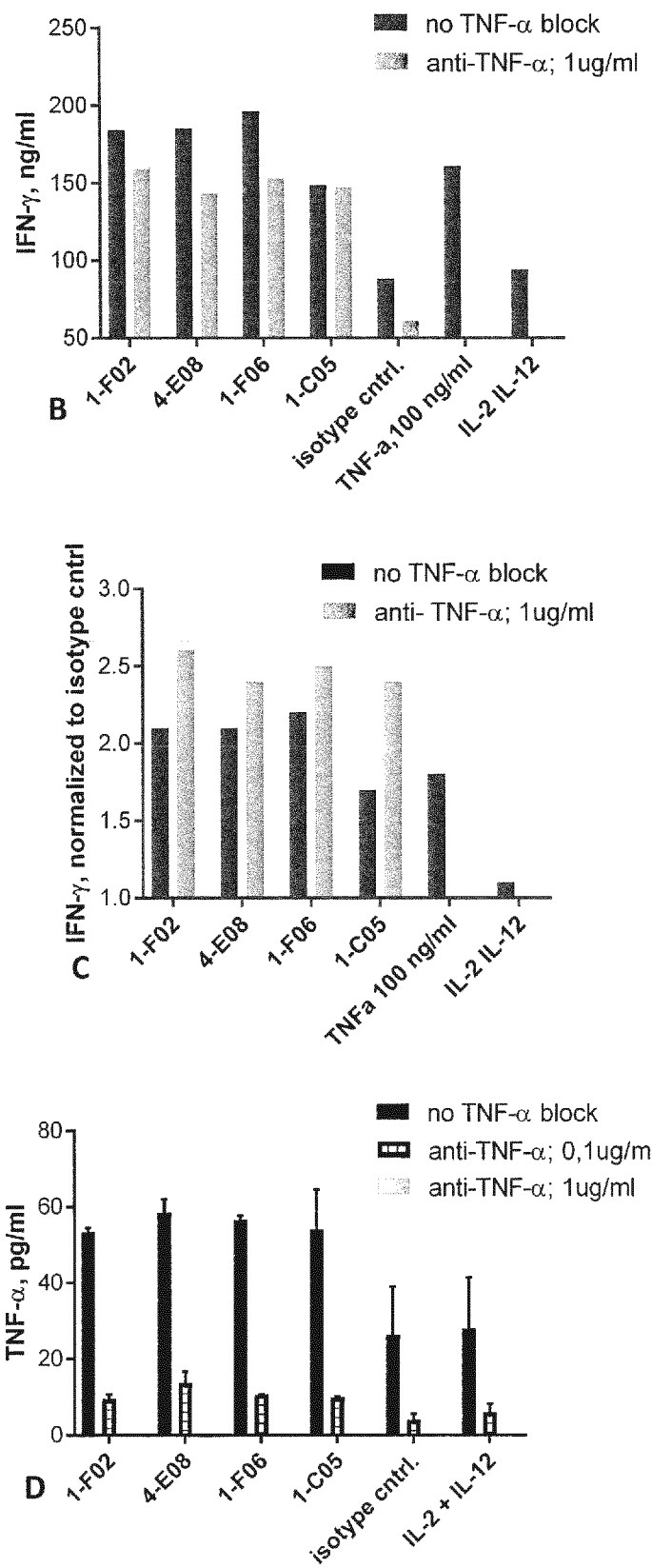
*Fig.8, cont.*

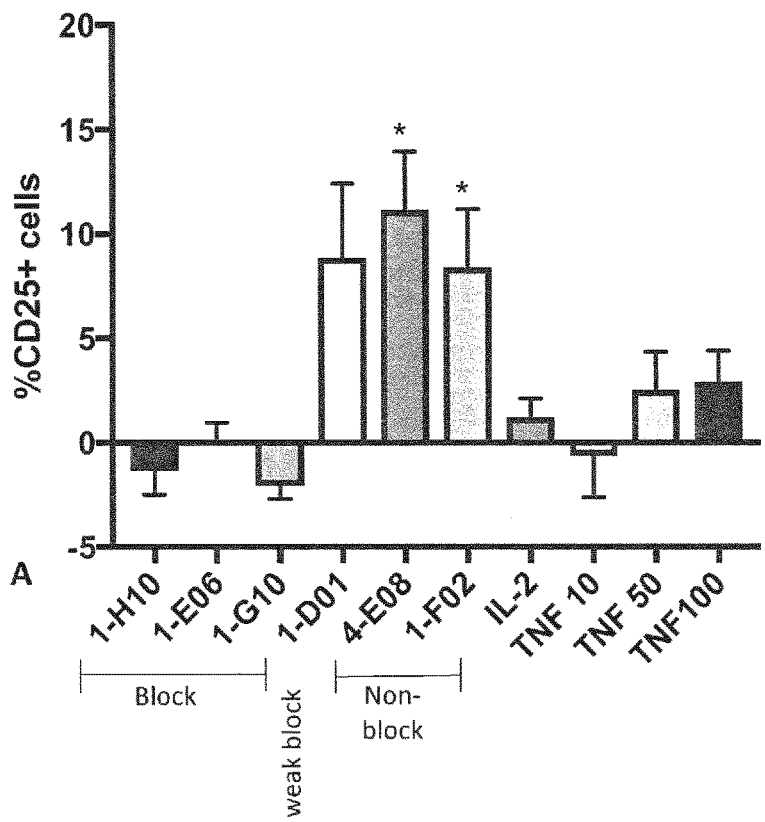
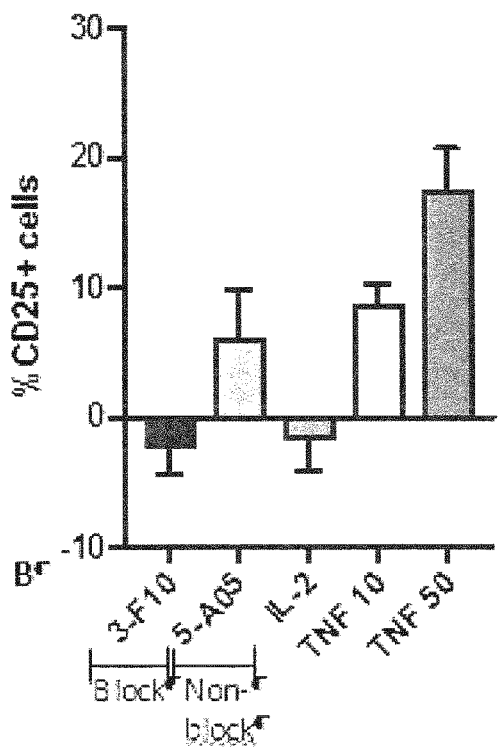
Fig. 9

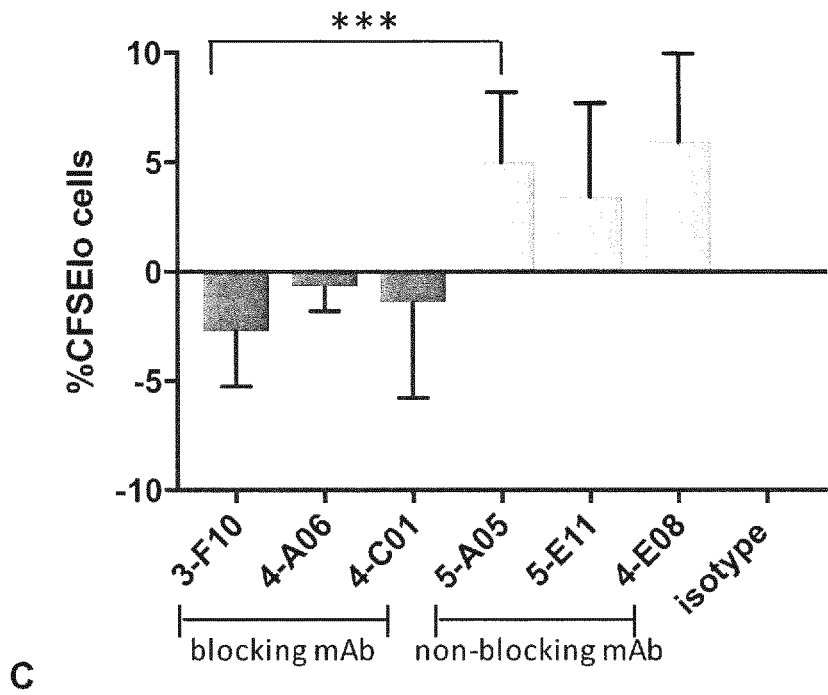
C
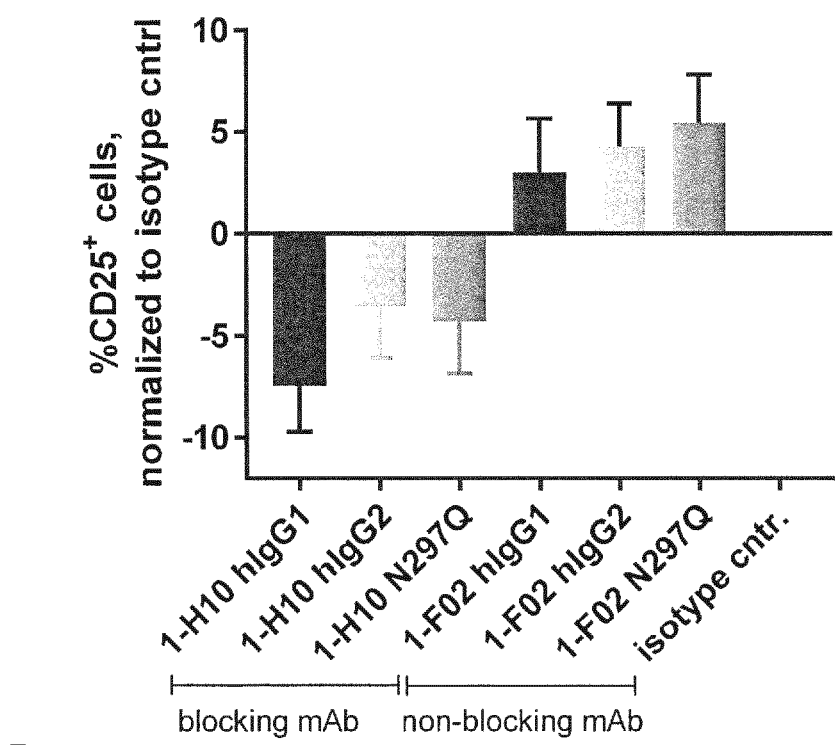
D
*Fig. 10, cont.*

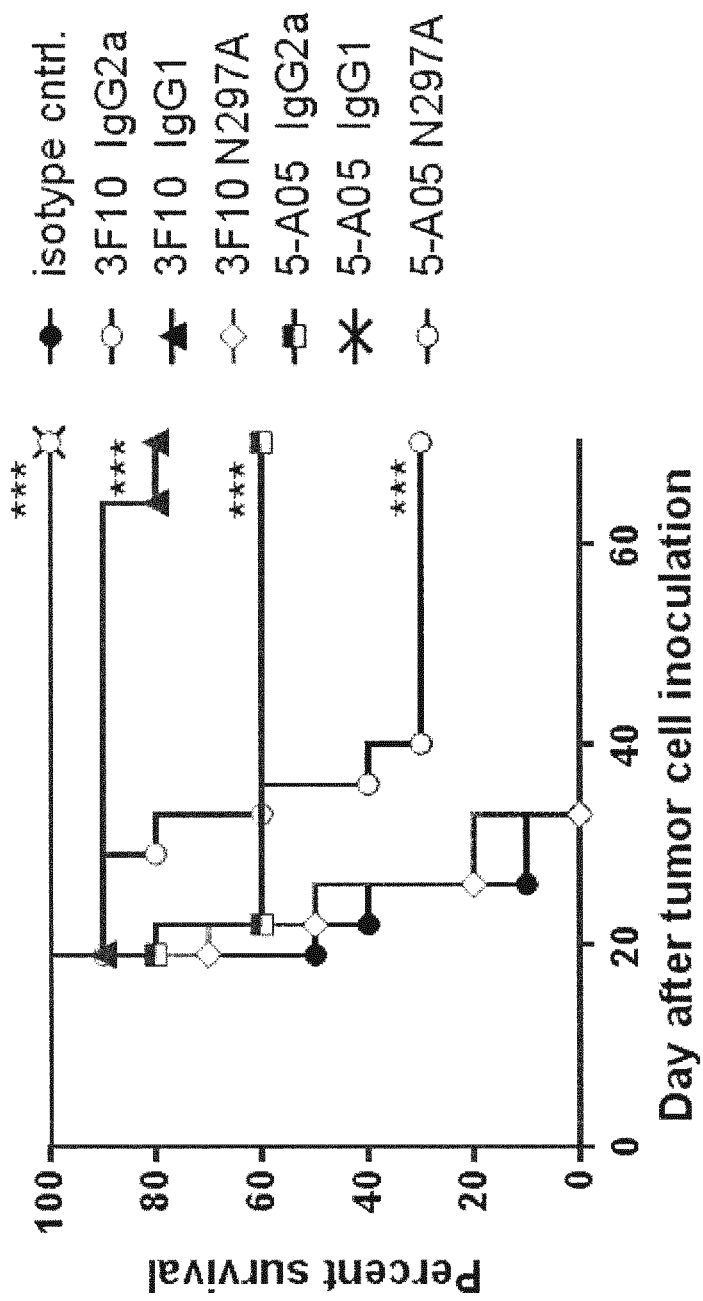
Fig. 11, cont.

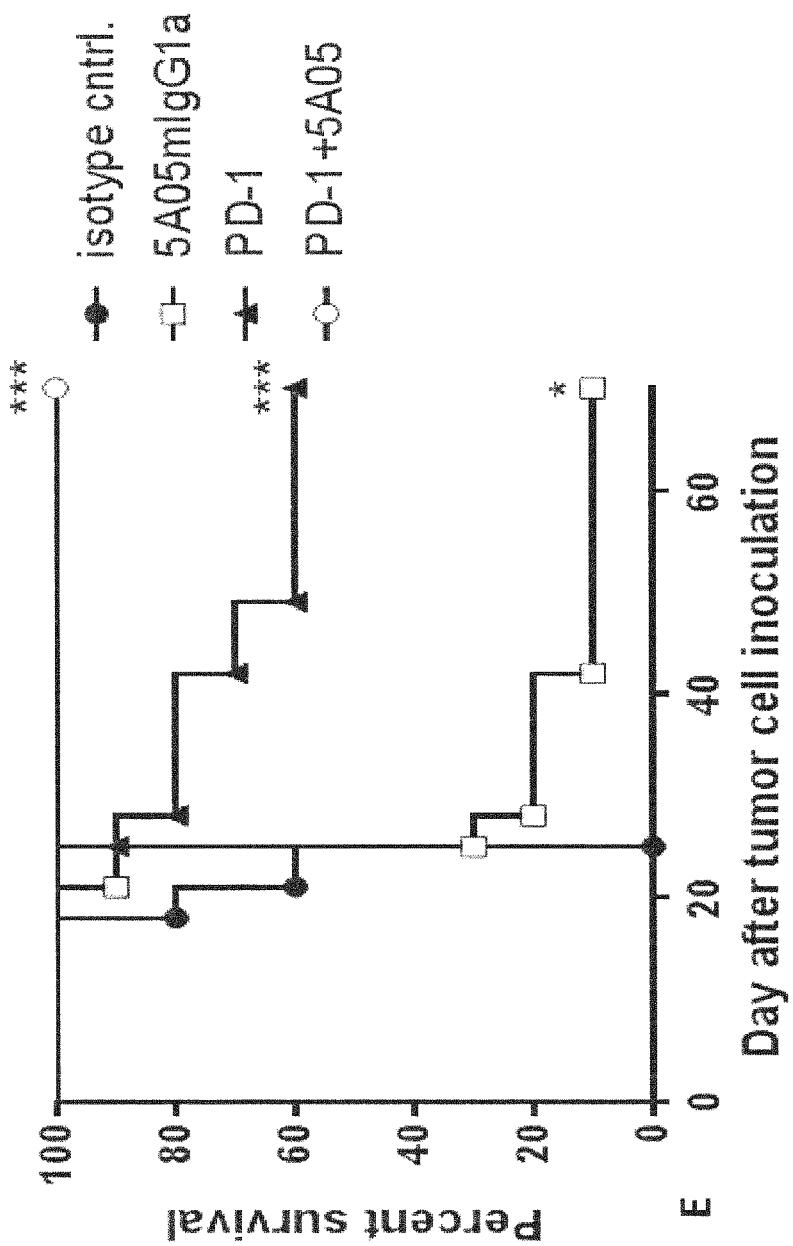
Fig. 12, cont.

Fig. 20, cont.

TNFR2 domain 3

| | T | C | R | P | G | W | Y | C | A | L | S | K | Q | E | G | · | C | R | L | C | A | P | L | R | K | C | R | P | G | F | G | V | A | R | P | G | T | E | T | S | D | V | V | C | K |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Human-D3 sequence | T | C | R | P | G | W | Y | C | A | L | S | K | Q | E | G | · | C | R | L | C | A | P | L | R | K | C | R | P | G | F | G | V | A | R | P | G | T | E | T | S | D | V | V | C | K |
| Murine-D3 sequence | A | C | E | A | G | R | Y | C | A | L | K | T | H | S | G | · | C | R | Q | C | M | R | L | S | K | C | G | P | G | F | F | G | V | A | S | S | R | A | P | N | G | N | V | L | C | K |

WT           T C R P G W Y C A L S K Q E G C R L C A P L R K C R P G F G V A R P G T E T S D V V C K

Mouse sequence 1   A C E A G R Y C A L K T H S G C R L C A P L R K C R P G F G V A R P G T E T S D V V C K
                                         aa 119-132

Mouse sequence 2   T C R P G W Y C A L S K Q E G S C R Q C M R L S K C G P G F G V A R P G T E T S D V V C K
                                                              aa 134-144

Mouse sequence 3   T C R P G W Y C A L S K Q E G C R L C A P L R K C R P G F G V A S S R A P N G N V L C K
                                                                             aa 151-160

Mouse sequence 4   T C R P G W Y C A L S T H S G S C R Q C M R L S K C G P G F G V A R P G T E T S D V V C K
                                                             aa 130-144

Fig. 21

AGONISTIC ANTI TNFR2 ANTIBODY MOLECULES

This application is a national phase application under 35 U.S.C. § 371 of International Application No. PCT/EP2019/080003, filed Nov. 1, 2019, which claims priority to European Application No. 18203996.6, filed Nov. 1, 2018. The entire contents of each of the above referenced disclosures is specifically incorporated herein by reference.

FIELD OF THE INVENTION

The present invention relates to novel agonistic antibodies that specifically bind to tumor necrosis factor receptor 2 (TNFR2) but that do not block the ligand TNF-α from binding to the TNFR2. The invention also relates to use thereof in medicine, such as in treatment of cancer or chronic inflammatory diseases.

BACKGROUND OF THE INVENTION

Tumor necrosis factor (TNF) receptor 2 (TNFR2, TNFR-2 or TNFRII), also known as tumor necrosis factor receptor superfamily member 1B (TNFRSF1B) and CD120b, is a membrane receptor that binds tumor necrosis factor-alpha (TNF-α or TNFα). It is found i.e. on the surface of T cells, monocytes and macrophages, and can activate the proliferation of TNFR2 receptor expressing cells through nuclear factor kappa B (NF-κB). Notably, TNFR2 is highly upregulated in cancer and in particular on tumor-infiltrating immune cells, e.g. regulatory T cells (Tregs), $CD8^+$ cytotoxic effector T cells, and different myeloid cell subpopulations TNFR2 has been discussed as a promising target for cancer immunotherapy, and has been described to be highly expressed on the surface of i.a. intratumoral Tregs and many human tumor cells (Williams G S et al, Oncotarget. 2016; 7(42): 68278-68291; Vanamee E S et al, Trends in Molecular Medicine, 2017, vol. 23, issue 11, 1037-1046; Frontiers in Immunology, November 2017|Volume 8|Article 1482, Sci Signal. 2018 Jan. 2; 11(511)).

Regulatory T cells (which may also be called Treg cells, Tregs or $T_{regs}$, and which formerly were known as suppressor T cells or suppressive regulatory T cells) constitute a subpopulation of T cells capable of suppressing other immune cells in normal and pathological immune settings. Tregs are CD4 positive cells ($CD4^+$ cells). There are other $CD4^+$ T cells that are not Tregs; however, Tregs can be separated from non-Treg $CD4^+$ cells in that Tregs also are FOXP3 positive ($FOXP3^+$) while the non-Treg $CD4^+$ cells are FOXP3 negative ($FOXP3^-$). Tregs can also be separated from non-Treg $CD4^+$ cells in that Tregs also are CD25+ $CD127^{neg/low}$ while the non-Treg $CD4^+$ cells are either $CD25^-CD127^+$ or $CD25^+CD127^+$.

TNFR2 has also been discussed in connection with autoimmune diseases (Faustman D L et al, Front Immunol. 2013; 4: 478, Clin Transl Immunology. 2016 Jan. 8; 5(1), J Neurosci. 2016 May 4; 36(18):5128-43) and inflammatory diseases (Ait-Ali D et al, Endocrinology. 2008 June; 149 (6):2840-52, Sci Rep. 2016 Sep. 7; 6:32834).

Anti-TNFR2 antibodies of different types and with various characteristics have also been described previously. For example, Williams et al (Oncotarget. 2016 Oct. 18; 7(42): 68278-68291) describes both ligand blocking and ligand non-blocking agonistic antibodies.

WO 2014/124134 discloses the use of a TNFR2 agonist, such as an agonistic anti-TNFR2 antibody and/or an NF-κB activator for in vitro production of a composition enriched in $CD4+CD25^{hi}$ Tregs. The composition is said to be useful in treatment of immunological disorders or infectious diseases in patients.

WO 2017/040312 discloses anti-TNFR2 antibodies, and in particular agonistic anti-TNFR2 antibodies, that are capable of promoting TNFR2 signaling and having an effect on expansion or proliferation of Tregs. WO 2017/040312 discloses antibodies that bind specifically to an epitope comprising the sequence KCSPG (SEQ ID NO: 224), but not to an epitope comprising the sequence KCRPG (SEQ ID NO: 225), thus excluding the antibodies of U.S. Pat. No. 9 821 010 discussed above, or alternatively not to another TNFR superfamily member. The agonistic antibodies are said to be useful in treatment of immunological diseases. WO 2017/040312 further sets out the full sequence of human TNFR2.

WO 2017/083525 discusses pharmacological compositions comprising antiTNFR2 antibodies and use thereof in treatment of disorders associated with TNF-α and/or TNFR2, such as cancer. WO 2017/083525 further discusses antibodies comprising a human IgG1 Fc domain which is null for binding to an Fcγ receptor, and also suppression of expansion of Tregs.

In addition, anti-TNFR2 antibodies that are capable of acting as TNFR2 agonists are described in Galloway et al, (Eur. J. Immunol. 22:3045-3048, 1992), Tartaglia et al. (J. Biol. Chem. 268:18542-18548, 1993), Tartaglia et al, (J. Immunol. 151:4637-4641, 1993), Smith et al. (J. Biol. Chem. 269:9898-9905, 1994), and Armani et al. (Am. J. Respir. Cell. Mol. Biol. 15:55-63, 1996).

However, none of these documents teach or suggest agonistic TNFR2 antibodies which specifically bind to TNFR2, but that do not block the ligand TNF-α from binding to the same TNFR2.

Fc receptors are membrane proteins which are found on the cell surface of immune effector cells including monocytes, macrophages, dendritic cells, neutrophils, mast cells, basophils, eosinophils and Natural Killer cells and B lymphocytes. The name is derived from their binding specificity for the Fc region of antibodies. Fc receptors are found on the cell membrane—otherwise known as the plasma membrane or cytoplasmic membrane, Fc receptors can be subdivided into activating FcγR and inhibitory FcγR, which are known to co-ordinately regulate cellular activation through binding of aggregated immunoglobulin G Fc's, and transmission of activating or inhibitory signals into the cell through intracellular ITAM or ITIM motifs. FcR binding of aggregated immunoglobulin or immune complexes, can mediate antibody internalization into the cell, and can result in antibody-mediated phagocytosis, antibody-dependent cell-mediated cytotoxicity, or antigen presentation or cross-presentation. FcRs are also known to mediate or enhance cross-linking of antibody-bound cell surface receptors. Such cross-linking is known to be required for some (Li et al 2011. 'Inhibitory Fcgamma receptor engagement drives adjuvant and anti-tumor activities of agonistic CD40 antibodies', *Science*, 333: 1030-4; White et al. 2011. 'Interaction with FcgammaRIIB is critical for the agonistic activity of anti-CD40 monoclonal antibody', *J Immunol*, 187: 1754-63) but not all (Richman et al 2014. 'Anti-human CD40 monoclonal antibody therapy is potent without FcR crosslinking', *Oncoimmunology*, 3: e28610) antibodies ability to activate signaling in targeted cells, and may or may not be required to achieve therapeutic effects.

A subgroup of the Fc receptors is Fcγ receptors (Fc-gamma receptors, FcgammaR, FcγR), which are specific for IgG antibodies. There are two types of Fcγ receptors: activating Fcγ receptors (also denoted activatory Fcγ receptors) and inhibitory Fcγ receptors. The activating and the inhibitory receptors transmit their signals via immunoreceptor tyrosine-based activation motifs (ITAM) or immunoreceptor tyrosine-based inhibitory motifs (ITIM), respectively. In humans, FcγRIIb (CD32b) is an inhibitory Fcγ receptor, while FcγRI (CD64), FcγRIIa (CD32a), FcγRIIc (CD32c) and FcγRIIIa (CD16a) are activating Fcγ receptors. FcγgRIIIb is a GPI-linked receptor expressed on neutrophils that lacks an ITAM motif but through its ability to cross-link lipid rafts and engage with other receptors is also considered activatory. In mice, the activating receptors are FcγRI, FcγRIII and FcγRIV.

It is well-known that antibodies can modulate immune cell activity through interaction with Fcγ receptors. Specifically, how antibody immune complexes modulate immune cell activation is determined by their relative engagement of activating and inhibitory Fcγ receptors. Different antibody isotypes bind with different affinity to activating and inhibitory Fcγ receptors, resulting in different A:I ratios (activation:inhibition ratios) (Nimmerjahn et al; Science. 2005 Dec. 2; 310(5753):1510-2).

By binding to inhibitory Fcγ receptors, an antibody can inhibit, block and/or down-modulate effector cell functions. By binding to an inhibitory FcγR, antibodies can further stimulate cell activation through aggregation of antibody-targeted signaling receptors on a target cell (Li et al. 2011. 'Inhibitory Fcgamma receptor engagement drives adjuvant and anti-tumor activities of agonistic CD40 antibodies', *Science*, 333: 1030-4; White et al 2011. 'Interaction with FcgammaRIIB is critical for the agonistic activity of anti-CD40 monoclonal antibody', *J Immunol*, 187: 1754-63; White et al 2014. 'Fcgamma receptor dependency of agonistic CD40 antibody in lymphoma therapy can be overcome through antibody multimerization', *J Immunol*, 193: 1828-35).

By binding to an activating Fcγ receptor, an antibody can activate effector cell functions and thereby trigger mechanisms such as antibody-dependent cellular cytotoxicity (ADCC), antibody dependent cellular phagocytosis (ADCP), cytokine release, and/or antibody dependent endocytosis, as well as NETosis (i.e. activation and release of NETs, Neutrophil extracellular traps) in the case of neutrophils. Antibody binding to an activating Fcγ receptor can also lead to an increase in certain activation markers, such as CD40, MHCII, CD38, CD80 and/or CD86.

Recent data published by i.a. the inventors demonstrate a critical and differential dependence of CD8 T cell agonist and Treg-depleting anti-4-1BB antibodies for binding to activating and inhibitory FcγRs respectively, for therapeutic efficacy (Buchan et al., 'Antibodies to Costimulatory Receptor 4-1BB Enhance Anti-tumor Immunity via T Regulatory Cell Depletion and Promotion of CD8 T Cell Effector Function', *Immunity* 2018 49(5):958-970). Moreover, and critically, simultaneous administration of CD8 T cell agonist and Treg depleting anti-4-1BB antibodies optimized for binding to activating and inhibitory FcγR respectively, impaired therapeutic activity. These data demonstrate the critical importance of developing antibodies with appropriate and tailored engagement of activating and inhibitory FcγRs to maximize therapeutic activity of antibodies with distinct mechanism-of-action. At the same time, they demonstrate that suboptimal engagement of activating and inhibitory FcγRs may severely reduce therapeutic efficacy.

These data were surprising as they contrasted with findings for antibodies to other TNFSR members, notably immune stimulatory anti-CD40 antibodies, which show an obligate need for engagement of the inhibitory, but not activating, FcγRs (Li et al. 2011. 'Inhibitory Fcgamma receptor engagement drives adjuvant and anti-tumor activities of agonistic CD40 antibodies', *Science*, 333: 1030-4; White et al. 2011. 'Interaction with FcgammaRIIB is critical for the agonistic activity of anti-CD40 monoclonal antibody', *J Immunol*, 187: 1754-63). Taken together, these results demonstrate that FcγR-dependence can vary between antibodies to different targets of the same receptor superfamily, and even between different types of antibodies to the same target, in a manner that is not easily predictable yet may be critical to understand and harness when developing antibodies for therapeutic use.

SUMMARY OF THE INVENTION

In the work leading to the present invention, and also to a parallel invention, two major different groups of anti-TNFR2 antibodies with powerful therapeutic effects, and different characteristics and mechanism-of-actions, were identified.

The inventors first identified a powerful therapeutic activity of antagonistic anti-TNFR2 antibodies that block TNF-α binding to TNFR2 receptor. The activity of such antibodies was shown to be dependent on FcγR-interactions, and in particular binding to activatory FcγR, for in vivo therapeutic activity. This group or category of powerful anti-TNFR2 therapeutic reagents was found to be characterized by 1) pronounced block and inhibition of TNF-α-induced TNFR2-signalling, and 2) an activity dependent on FcγR-engagement, benefitting most strongly from engaging activating over inhibitory FcγRs.

The inventors then identified a distinct group of anti-TNFR2 antibodies with equally powerful therapeutic activity in vivo, but whose characteristics in many respects are opposite to those of the antagonistic, blocking type of TNFR2 antibodies constituting the first group. The anti-TNFR antibodies of this second group do not depend on TNF-α blockade or inhibition of TNFR2-signalling for therapeutic activity, but rather is characterized by strong activation of TNFR2-signalling. Further contrasting with the blocking antibodies of the first group, the agonistic antibodies of the second group do not show obligate dependence on antibody:FcγR-engagement, even though their activity is improved with FcγR:engaging antibody variants. In further contrast to the antagonistic blocking antibodies of the first group, the agonistic antibodies of the second group show greatest activity in antibody variants with improved binding to inhibitory vs activating FcγR.

The present invention relates to the second group of anti-TNFR2 antibodies, i.e. to agonistic antibody molecules that specifically bind to TNFR2 but that do not block the ligand TNF-α from binding to TNFR2. Such antibodies are powerful therapeutic reagents and useful in medicine.

Antagonistic blocking antibodies belonging to the first group are used in the Examples below for comparison with the agonistic, non-blocking TNFR2 antibody molecules of the present invention. In the examples, also other antibodies with some characteristics similar to either those of the first or second group, or both, are used for comparison, as further explained below.

Thus, the present invention relates to agonistic antibody molecules that specifically bind to TNFR2 on a target cell and that do not block TNF-α ligand binding to TNFR2.

The present invention also relates to specific examples of such novel agonistic TNFR2 antibody molecules.

The present invention also relates to isolated nucleotide sequences encoding at least one of the above antibody molecules.

The present invention also relates to plasmids comprising at least one of the above nucleotide sequences.

The present invention also relates to viruses comprising at least one of the above nucleotide sequences or plasmids.

The present invention also relates to cells comprising at least one of the above nucleotide sequences, or at least one of the above plasmids, or at least one of the above viruses.

The present invention also relates to the above antibody molecules, nucleotide sequences, plasmids, viruses and/or cells for use in medicine.

The present invention also relates to the above antibody molecules, nucleotide sequences, plasmids, a viruses and/or cells for use in the treatment of cancer or a chronic inflammatory disease.

The present invention also relates to the use of the above antibody molecules, nucleotide sequences, plasmids, viruses and/or cells for use in the treatment of cancer or a chronic inflammatory disease.

The present invention also relates to pharmaceutical compositions comprising or consisting of at least one of the above antibody molecules, nucleotide sequences, plasmids, viruses and/or cells, and optionally a pharmaceutically acceptable diluent, carrier, vehicle and/or excipient. Such a pharmaceutical composition may be used in the treatment of cancer or a chronic inflammatory disease.

The present invention also relates to methods for treatment of cancer or a chronic inflammatory disease in a subject comprising administering to the subject a therapeutically effective amount of at least one of the above antibody molecules, nucleotide sequences, plasmids, viruses and/or cells.

The present invention also relates to antibody molecules, antibody molecules for use, isolated nucleotide sequences, isolated nucleotide sequences for use, plasmids, plasmids for use, viruses, viruses for use, cells, cells for use, uses, pharmaceutical compositions and methods of treatment as described herein with reference to the accompanying description, examples and/or figures.

DETAILED DESCRIPTION OF THE INVENTION

Thus, the present invention concerns agonistic TNFR2 antibody molecules that specifically bind to TNFR2, but that do not block the ligand TNF-α from binding to the same TNFR2. Preferably, the antibody molecules have intrinsic agonistic activity.

The agonistic antibody molecules disclosed herein do not block TNF-α from binding to TNFR2 and further they do not block TNFR2 signaling. It has been clearly demonstrated that TNF-α mediated signaling through TNFR2 starts a signaling cascade that ends in activation of the nuclear transcription factor NFκB (Thommesen et al, "Distinct differences between TNF receptor 1- and TNF receptor 2-mediated activation of NFkappaB". J Biochem Mol Biol. 2005 May 31; 38(3):281-9; Yang et al. "Role of TNF-TNF Receptor 2 Signal in Regulatory T Cells and Its Therapeutic Implications". Front Immunol. 2018 Apr. 19; 9:784). This in turn results in activation of the cell and synthesis of several pro-inflammatory factors, one of them being IFN-γ in NK cells (Liu et al. "NF-κB signaling in inflammation". Signal Transduct Target Ther. 2017; 2. pii: 17023; Tato et al. "Opposing roles of NF-kappaB family members in the regulation of NK cell proliferation and production of IFN-gamma". Int Immunol. 2006 April; 18(4):505-13). Herein the terms TNFR2 signaling and TNFR2 activation are used interchangeably. The antibody molecules bind specifically to TNFR2. It is well known that an antibody specifically binds to or interacts with a defined target molecule or antigen, and that this means that the antibody preferentially and selectively binds its target and not a molecule which is not a target. By "antibody molecule that specifically binds TNFR2" or "TNFR2 specific antibody molecule" we mean an antibody that binds TNFR2 protein in a dose-dependent manner but not to an unrelated protein. In addition, the same antibody binds cells that endogenously express TNFR2, and this binding can be blocked out by pre-incubation of the same cells with a commercially available polyclonal TNFR2 antibody reagent, showing that no non-specific binding can be detected when TNFR2 is masked by a polyclonal reagent. This is shown in Example 2.

The antibody molecule that specifically binds TNFR2 (or the anti-TNFR2 antibody molecule) refers to an antibody molecule that specifically binds to at least one epitope in the extracellular domain of TNFR2. Cell surface antigen and epitope are terms that would be readily understood by one skilled in immunology or cell biology.

Methods of assessing protein binding are known to the person skilled in biochemistry and immunology. It would be appreciated by the skilled person that those methods could be used to assess binding of an antibody to a target and/or binding of the Fc region of an antibody to an Fc receptor; as well as the relative strength, or the specificity, or the inhibition, or prevention, or reduction in those interactions. Examples of methods that may be used to assess protein binding are, for example, immunoassays, BIAcore, western blots, radioimmunoassay (RIA) and enzyme-linked immunosorbent assays (ELISAs) and Flow cytometry (FACS). See Fundamental Immunology Second Edition, Raven Press, New York at pages 332-336 (1989) for a discussion regarding antibody specificity.

The target cells expressing the TNFR2 to which the agonistic antibody binds in accordance with the present invention can be any TNFR2 expressing immune cells, such as CD8 positive cells and myeloid cells.

The effect of the binding of the agonistic antibody molecules according to the invention to TNFR2 may be activation of T-cells and/or myeloid cells; and/or infiltration of T-cells and/or myeloid cells into diseased tissue; and/or a change in composition of T-cells and/or myeloid cells in diseased tissue. Change in composition of T-cells and/or myeloid cells means herein different absolute or relative counts of various cells subpopulations, such as Tregs, CD8 positive cells, tumor associated macrophages (TAMs) (including different sub-populations thereof), myeloid-derived suppressor cells (MDSCs) and/or proinfammatory macrophages.

Diseased tissue means in this context either tumor tissue (i.e. all cells in the tumor microenvironment, including tumor cells, immune cells, endothelial cells and stromal cells) or tissue affected by a chronic inflammatory disease.

To decide whether or not an antibody molecule blocks— or rather in the context of the present invention does not block—ligand binding to TNFR2, it is possible to use an ELISA assay determining the amount of bound TNF-α ligand to immobilized TNFR2 receptor in the presence of TNFR2 specific antibodies. A non-blocking antibody will not prevent the ligand, TNF-α, from binding to the immobilized receptor TNFR2. This is demonstrated and explained in more detail in Example 3 below. More specifically, a non-blocking TNFR2 antibody molecule according to the present invention is an antibody molecule that reduces the TNF-α binding to TNFR2 by less than 50% compared to TNF-α binding in the presence of only an isotype control antibody molecule. In some embodiments, this is determined in high-dose, one-point ELISA as or a dose-titration ELISA as shown in Example 3 and FIGS. 6 and 7.

On the contrary, a blocking antagonistic antibody molecule is a complete blocker, which additionally is capable of antagonizing TNFR2 signaling. Such antibody molecules are used for comparison in the examples below. A complete blocker is defined herein as an antibody molecule that reduces the TNF-α binding to TNFR2 by more than 98%, i.e. up to 100%, compared to TNF-α binding in the presence of only an isotype control antibody molecule. An isotype control antibody is an antibody raised towards a protein or other structure that is not present in any form in the assay under study. The isotype control ideally has the same framework but at least the same Fc part as the comparing antibodies. This is well known to the skilled person. In the examples described herein, the isotype control had the same framework, the same Fc part, and was specific for Fluorescein isothiocyanate (FITC). In some embodiments the complete blocker reduces the TNF-α binding with more than 99.5%. Other types of blockers are partial blockers and weak blockers. As used herein, a partial blocker is an antibody molecule that reduces the TNF-α binding to TNFR2 by 60-98% compared to TNF-α binding in the presence of only an isotype control antibody molecule, and a weak blacker is an antibody molecule that reduces the TNF-α binding to TNFR2 by less than 60%, such as 50-59.9%, compared to TNF-α binding in the presence of only an isotype control antibody molecule.

Complete blocking, antagonistic antibody molecules, partially blocking antibody molecules and weak blocking antibody molecules are used in the examples for comparison with the agonistic non-blocking antibody molecules of the present invention.

Several properties and features can underlie and (co-)determine the biological activity of antibodies. Besides ability to block or not block ligand from binding to the receptor, important such properties include antibody molecules ability to modulate receptor signaling i.e. agonize or antagonize receptor signaling, and antibody dependence on FcγR interactions to confer therapeutic activity.

We first characterized the ability of complete blocking, partial blocking and non-blocking antibodies to modulate TNFR2 signaling. Two extremes were identified.

On the first extreme, we identified antibodies that completely blocked ligand-binding to TNFR2, which blocked TNF-α induced TNFR2 signaling, and which did not themselves induce signaling upon binding to cell-endogenously expressed TNFR2. This group of ligand-blocking, antagonistic, antibodies constitute a separate invention and are included herein for comparison.

On the other extreme, we identified antibodies that do not block ligand-binding to TNFR2, but upon binding to TNFR2 endogenously expressing cells agonized the receptor. This second group of antibodies forms the basis for the present invention.

As used herein, a non-blocking antibody is an antibody molecule that reduces the TNF-α binding to TNFR2 0-50% (such as 5, 10, 15, 20, 25, 30, 35, 40, 45 or 50%, including all integers and all decimal numbers in between) compared to TNF-α binding in the presence of only an isotype control antibody molecule.

Antibodies and categories defined by partial blocking agonistic, partial blocking non-agonistic, and complete blocking non-antagonistic, were additionally identified demonstrating the complex biology and great heterogeneity of anti-TNFR2 antibodies clearly demonstrating that the antibodies of the present invention form a unique group.

To determine whether an antibody has agonist or antagonistic activity it is possible to use a Natural Killer (NK) cell assay as described in Example 4. Briefly, NK cells have been described to respond to IL-2 and IL-12 stimuli with secretion of IFN-γ. Soluble TNF-α is endogenously produced and present at robust but suboptimal concentrations (~100 pg/ml), for TNFR2 signaling, meaning that IFN-γ can be both increased and decreased through modulation of TNFR2 signaling. Consequently, exogenous addition of TNF-α at TNFR2 signaling optimal concentration enhances IFN-γ concentrations in this assay, as does incubation with agonist anti-TNFR2 antibody. Contrarily, co-incubation with anti-TNF-α antibody or ligand-blocking antagonist antibodies described herein for comparison, decreases IFN-γ release in this assay. Thus, this assay can be used to identify agonist or antagonist activity, or lack thereof, of anti-TNFR2 antibodies. (INFα Augments Cytokine-Induced NK Cell IFNγ Production through TNFR2. Almishri W. et al. *J Innate Immun*, 2016; 8:617-629)

Consequently, the ability of antibodies to agonize i.e. induce TNFR2 signaling can be monitored using this experimental set-up. The ability of antibodies to induce signaling themselves upon binding to TNFR2 in the same Natural Killer (NK) cell assay, can be evaluated by monitoring and comparing increases in IFN-γ release to those observed following culture in the presence or absence of exogenous TNF-α added at signaling optimal concentrations as described in Example 4. Hence an agonistic TNFR2 antibody can be defined as an antibody that enhances the IFN-γ release by NK cells in this assay. An antibody with intrinsic agonistic capacity enhances the IFN-γ release by NK cells in a manner which is neither dependent on antibody cross-linking or interactions with Fc gamma receptors, nor dependent on presence of soluble TNF-α ligand. Intrinsic agonist activity can consequently be assessed using antibody formats which do not productively engage with FcγR e.g. aglycosylated antibodies carrying a N297A mutation in the Fc-domain, or in assay systems/cells lacking FcγRs. NK cells are well known to the skilled person (Binyamin, L., et al (2008). Journal of immunology 180, 6392-6401; Blocking NK cell inhibitory self-recognition promotes antibody-dependent cellular cytotoxicity in a model of anti-lymphoma therapy). Using this assay, an agonistic antibody is defined as an antibody resulting in >100% (>2-fold) increase in IFN-γ release. Since this assay uses primary cells from PBMC donors, at least 4 donors need to be included and the mean values should be calculated from all donors. Cells from each donor to be included in calculation of means must have responded to the positive control (soluble TNF-α) treatment with >100% (>2-fold) increased IFN-γ levels relative to treatment with isotype control.

The agonistic antibody molecules described herein have an intrinsic agonistic activity, as explained above.

In some embodiments of the present invention, it is preferred that the antibody enhances IFN-γ release by NK cells in the above described assay by at least 100%.

In some embodiments, the agonistic activity may be improved by the antibody molecule binding to an Fcγ receptor in addition to binding to TNFR2. In some such embodiments, the agonistic non-blocking TNFR2 antibody molecules bind with higher affinity to inhibitory Fcγ receptors than to activating Fcγ receptors. With higher affinity to inhibitory Fcγ receptors than to activating Fcγ receptors, we include the meaning of variants that bind with higher affinity to inhibitory Fcγ receptors compared with individual activating Fcγ receptors, e.g. compared with either of FcγRIIA, FcγRIIIA and FcγRI.

The relatively high homology between mouse and human FcγR systems accounts for many of the general aspects of conserved FcγR mediated mechanisms between the species. However, mouse and human IgG subclasses differ in their affinities for their cognate FcγRs, making it important when translating FcγR-mediated observations in the mouse system into human IgG-based therapeutics to choose an antibody, antibody subclass and/or engineered subclass variant, that shows appropriate binding to human activating vs inhibitory FcγRs. The affinity and/or avidity of human antibody molecules for individual human FcγRs can be determined using surface plasmon resonance (SPR).

In some embodiments, the binding to an Fc receptor occurs through normal interaction between the Fc region of the agonistic antibody molecule and the Fc receptor. In some such embodiments the antibody molecule is an IgG, which has an Fc region binding to an Fcγ receptor. In some such embodiments, the anti-TNFRII antibody is of human IgG2 isotype, which has similar intermediate affinity for human inhibitory FcγRIIB and human activating FcγRIIA and FcγRIIIA, but does not productively engage with human activating FcγRI. In some embodiments the anti-TNFRII antibody is of human IgG1 isotype, which binds FcγRIIB with higher affinity compared with IgG2, but also binds activating human activating FcγRIIA, FcγRIIIA with higher affinity, and additionally binds activating FcγRI with high affinity. In other embodiments, the anti-TNFRII antibody is a human IgG engineered for enhanced binding to FcγRIIB e.g. the "SELF" mutation (Chu et al. "Inhibition of B cell receptor-mediated activation of primary human B cells by co-engagement of CD19 and FcgammaRIIb with Fc-engineered antibodies." Mol Immunol. 2008 September; 45(15): 3926-33), and/or engineered for relative enhanced binding to FcγRIIB compared to activating FcγRs e.g. V9 or V11 mutations (Mimoto et al. "Engineered antibody Fc variant with selectively enhanced FcγRIIb binding over both FcγRIIa' and FcγRIIa$^{H131}$". Protein Eng Des Sel. 2013 October; 26(10): 589-598.1. Such IgG variants engineered for enhanced binding to inhibitory FcγRIIB, or specifically enhanced binding affinity specifically to inhibitory FcγRIIB but not activating FcγRIIA, have been shown to increase in vivo agonist activity, and therapeutic activity, of the CD40 agonist antibody CP870,893 in animals humanized for activating and inhibitory FcγRs (Dahan et al. 2016. 'Therapeutic Activity of Agonistic, Human Anti-CD40 Monoclonal Antibodies Requires Selective FcgammaR Engagement', Cancer Cell, 29: 820-31).

The Fc receptor to which agonistic antibody molecule may bind in addition to TNFR2 is a receptor found on the surface of cells of myeloid origin, such as macrophages, monocytes, MDCSs, neutrophils, mast cells, basophils, or dendritic cells, or on the surface of lymphocytes such as NK cells, B cells, or certain T cells.

As mentioned above, antibody molecules often bind to Fc receptors via their Fc regions. Since the agonistic antibody molecules disclosed herein have intrinsic agonistic activity, they do not need to bind to Fc receptors to agonize TNFR2. This means that in some embodiments of the present invention it is possible to use antibody molecules that do not depend on Fc receptor binding through its Fc region, and it is in fact possible to use antibody molecules that do not have an Fc region. In some such embodiments, the antibody molecule may be a Fab'$_2$ or a PEGYLATED version thereof.

In some embodiments, the antibody molecules may be a divalent or multivalent antibody molecule corns prising single chain antibodies, Fabs, Fvs, scFvs, Fab's, and/or (Fab')$_2$. In other embodiments, the antibody molecules may comprise a modified Fc region, such as an aglycosylated variant of an IgG1 antibody molecule, Such aglycosylation may for example be achieved by an amino acid substitution of the asparagine in position 297 (N297X) in the antibody chain. The substation may be with a glutamine (N297Q), or with an alanine (N297A), or with a glycine (N297G), or with an asparagine (N297D), or by a serine (N297S), Other substitutions have e.g. been described by Jacobsen F W et al, JBC 2017, 292, 1865-1875, (see e.g. Table 1); such additional substitutions include L242C, V259C, A287C, R292C, V302C, L306C, V323C, I332C, and/or K334C.

In some embodiments, the agonistic TNFR2 antibody molecule is an IgG1, IgG3 or IgG4 antibody molecule.

In some embodiments, the agonistic TNFR2 antibody molecule is an IgG antibody molecule showing improved binding to one or several activatory Fc receptors and/or being engineered for improved binding to one or several activatory Fcγ receptors and/or being engineered for improved relative binding to activatory over inhibitory Fcγ receptors. In some embodiments, the anti-TNFR2 antibody is an Fc-engineered human IgG1 antibody. Examples of such engineered antibody variants include afucosylated antibodies with selective improved antibody binding to FcγRIIIA, and antibodies engineered by directed, mutational, or by other means, amino acid substitution resulting in improved binding to one or several activating Fcγ receptors compared to inhibitory FcγRIIB (Richards et al. 2008. 'Optimization of antibody binding to FcgammaRIIa enhances macrophage phagocytosis of tumor cells', Mol Cancer Ther, 7: 2517-27; Lazar et al. 2006. 'Engineered antibody Fc variants with enhanced effector function', Proc Natl Acad Sci USA, 103: 4005-10)

In some embodiments, the human IgG antibody that is engineered for improved binding to activating Fc gamma receptors may be a human IgG antibody carrying the two mutations S239D and I332E, or the three mutations S239D, I332E andA330L, and/or G236A mutations in its Fc portion. In some embodiments, the human IgG antibody that is engineered for improved binding to activating Fc gamma receptors may be an afucosylated human IgG antibody.

As explained above, that the antibody molecules are intrinsic agonists means that they are agonistic both in the absence and in the presence of TNF-α. In some embodiments the antibody is agonistic in the absence of TNF-α. In some embodiment the antibody is agonistic in the presence of TNF-α.

The target cell expressing the TNFR2 to which the agonistic antibody binds in accordance with the present invention can be selected from the group consisting of TNFR2 expressing immune cells or cancer cells.

Antibodies are well known to those skilled in the art of immunology and molecular biology. Typically, an antibody comprises two heavy (H) chains and two light (L) chains. Herein, we sometimes refer to this complete antibody molecule as a full-size or full-length antibody. The antibody's heavy chain comprises one variable domain (VH) and three constant domains (CH1, CH2 and CH3), and the antibody's molecule light chain comprises one variable domain (VL) and one constant domain (CL). The variable domains (sometimes collectively referred to as the Fv region) bind to the antibody's target, or antigen. Each variable domain comprises three loops, referred to as complementary determining regions (CDRs), which are responsible for target binding.

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and in humans several of these are further divided into subclasses (isotypes), e.g., IgG1, IgG2, IgG3, and IgG4; IgA1 and IgA2.

Another part of an antibody is the Fc region (otherwise known as the fragment crystallizable domain), which comprises two of the constant domains of each of the antibody's heavy chains. As mentioned above, the Fc region is responsible for interactions between the antibody and Fc receptor.

The term antibody molecule, as used herein, encompasses full-length or full-size antibodies as well as functional fragments of full length antibodies and derivatives of such antibody molecules.

Functional fragments of a full-size antibody have the same antigen binding characteristics as the corresponding full-size antibody and include either the same variable domains (i.e. the VH and VL sequences) and/or the same CDR sequences as the corresponding full-size antibody. A functional fragment does not always contain all six CDRs of a corresponding full-size antibody. It is appreciated that molecules containing three or fewer CDR regions (in some cases, even just a single CDR or a part thereof) are capable of retaining the antigen-binding activity of the antibody from which the CDR(s) are derived. For example, in Gao et al., 1994, J. Biol. Chem., 269: 32389-93 it is described that a whole VL chain (including all three CDRs) has a high affinity for its substrate.

Molecules containing two CDR regions are described, for example, by Vaughan & Sollazzo 2001, Combinatorial Chemistry & High Throughput Screening, 4: 417-430. On page 418 (right column—3 Our Strategy for Design) a minibody including only the H1 and H2 CDR hypervariable regions interspersed within framework regions is described. The minibody is described as being capable of binding to a target. Pessi et al., 1993, Nature, 362: 367-9 and Bianchi et al., 1994, J. Mol. Biol., 236: 649-59 are referenced by Vaughan & Sollazzo and describe the H1 and H2 minibody and its properties in more detail. In Qiu et al., 2007, Nature Biotechnology, 25:921-9 it is demonstrated that a molecule consisting of two linked CDRs are capable of binding antigen. Quiocho 1993, Nature, 362: 293-4 provides a summary of "minibody" technology. Ladner 2007, Nature Biotechnology, 25:875-7 comments that molecules containing two CDRs are capable of retaining antigen-binding activity.

Antibody molecules containing a single CDR region are described, for example, in Laune et al., 1997, JBC, 272: 30937-44, in which it is demonstrated that a range of hexapeptides derived from a CDR display antigen-binding activity and it is noted that synthetic peptides of a complete, single, CDR display strong binding activity. In Monnet et al., 1999, JBC, 274: 3789-96 it is shown that a range of 12-mer peptides and associated framework regions have antigen-binding activity and it is commented on that a CDR3-like peptide alone is capable of binding antigen. In Heap et al., 2005, J. Gen. Virol., 86: 1791-1800 it is reported that a "micro-antibody" (a molecule containing a single CDR) is capable of binding antigen and it is shown that a cyclic peptide from an anti-HIV antibody has antigen-binding activity and function. In Nicaise et al., 2004, Protein Science, 13:1882-91 it is shown that a single CDR can confer antigen-binding activity and affinity for its lysozyme antigen.

Thus, antibody molecules having five, four, three or fewer CDRs are capable of retaining the antigen binding properties of the full-length antibodies from which they are derived.

The antibody molecule may also be a derivative of a full-length antibody or a fragment of such an antibody. When a derivative is used it should have the same antigen binding characteristics as the corresponding full-length antibody in the sense that it binds to the same epitope on the target as the full-length antibody.

Thus, by the term "antibody molecule", as used herein, we include all types of antibody molecules and functional fragments thereof and derivatives thereof, including: monoclonal antibodies, polyclonal antibodies, synthetic antibodies, recombinantly produced antibodies, multi-specific antibodies, bi-specific antibodies, human antibodies, antibodies of human origin, humanized antibodies, chimeric antibodies, single-chain Fvs (scFv), Fab fragments, F(ab')$_2$ fragments, F(ab') fragments, disulfide-linked Fvs (sdFv), antibody heavy chains, antibody light chains, homo-dimers of antibody heavy chains, homo-dimers of antibody light chains, heterodimers of antibody heavy chains, heterodimers of antibody light chains, antigen binding functional fragments of such homo- and heterodimers.

Further, the term "antibody molecule", as used herein, includes all classes of antibody molecules and functional fragments, including: IgG, IgG1, IgG2, IgG3, IgG4, IgA, IgM, IgD, and IgE, unless otherwise specified.

In some embodiments, the antibody molecule is a human antibody molecule, a humanized antibody molecule or an antibody molecule of human origin. In some such embodiments, the antibody molecule is an IgG antibody. It is known that optimal costimulation of TNFR superfamily agonist receptors, such as TNFR2, depends on antibody engagement of the inhibitory FcγRII. In the mouse, the IgG1 isotype, which binds preferentially to inhibitory Fc gamma receptor (FcγRIIB) and only weakly to activatory Fc gamma receptors, is known to be optimal for costimulatory activity of monoclonal antibodies targeting the TNFR-superfamily. While no direct equivalent of the mouse IgG1 isotype has been described in man, antibodies may be engineered to show a similarly enhanced binding to inhibitory over activatory human Fc gamma receptors. Such engineered TNFR-superfamily targeting antibodies also have improved costimulatory activity in vivo in transgenic mice engineered to express human activatory and inhibitory Fc gamma receptors (Dahan et al, 2016, Therapeutic Activity of Agonistic, Human Anti-CD40 Monoclonal Antibodies Requires Selective FcγR Engagement. Cancer Cell. 29(6):820-31). In some embodiments, the antibody molecule is therefore of an isotype that engages inhibitory Fc receptors in an optimal way. In some embodiments the antibody molecule is an IgG2 antibody.

In some embodiments, the agonistic antibody molecule that specifically binds TNFR2 may be a lama antibody, and in particular a lama hcIgG. Like all mammals, camelids produce conventional antibodies made of two heavy chains and two light chains bound together with disulphide bonds in a Y shape (IgG$_1$). However, they also produce two unique subclasses of immunoglobulin G, IgG2 and IgG$_3$, also known as heavy chain IgG (hcIgG). These antibodies are made of only two heavy chains that lack the CH1 region but still bear an antigen binding domain at their N-terminus called V$_H$H. Conventional Ig requires the association of variable regions from both heavy and light chains to allow a high diversity of antigen-antibody interactions. Although isolated heavy and light chains still show this capacity, they exhibit very low affinity when compared to paired heavy and light chains. The unique feature of hcIgG is the capacity of their monomeric antigen binding regions to bind antigens with specificity, affinity and especially diversity that are comparable to conventional antibodies without the need of pairing with another region.

As outlined above, different types and forms of antibody molecules are encompassed by the invention, and would be known to the person skilled in immunology. It is well known that antibodies used for therapeutic purposes are often modified with additional components which modify the properties of the antibody molecule.

Accordingly, we include that an antibody molecule described herein or an antibody molecule used as described herein (for example, a monoclonal antibody molecule, and/or polyclonal antibody molecule, and/or bi-specific antibody molecule) comprises a detectable moiety and/or a cytotoxic moiety.

By "detectable moiety", we include one or more from the group comprising of: an enzyme; a radioactive atom; a fluorescent moiety; a chemiluminescent moiety; a bioluminescent moiety. The detectable moiety allows the antibody molecule to be visualized in vitro, and/or in vivo, and/or ex vivo.

By "cytotoxic moiety", we include a radioactive moiety, and/or enzyme, for example wherein the enzyme is a caspase, and/or toxin, for example wherein the toxin is a bacterial toxin or a venom; wherein the cytotoxic moiety is capable of inducing cell lysis.

We further include that the antibody molecule may be in an isolated form and/or purified form, and/or may be PEGylated. PEGylation is a method by which polyethylene glycol polymers are added to a molecule such as an antibody molecule or derivative to modify its behavior, for example to extend its half-life by increasing its hydrodynamic size, preventing renal clearance.

As discussed above, the CDRs of an antibody bind to the antibody target. The assignment of amino acids to each CDR described herein is in accordance with the definitions according to Kabat E A et al. 1991, In "Sequences of Proteins of Immunological Interest" Fifth Edition, NIH Publication No. 91-3242, pp xv-xvii.

As the skilled person would be aware, other methods also exist for assigning amino acids to each CDR. For example, the International ImMunoGeneTics information system (IMGT®) (http://www.imgt.org/ and Lefranc and Lefranc "The Immunoglobulin FactsBook" published by Academic Press, 2001).

In some embodiments the antibody molecule that specifically binds TNFR2 is a human antibody.

In some embodiments, the antibody molecule that specifically binds TNFR2 is an antibody of human origin, i.e. an originally human antibody that has been modified as described herein.

In some embodiments, the antibody molecule that specifically binds TNFR2 is a humanized antibody, i.e. an originally non-human antibody that has been modified to increase its similarity to a human antibody. The humanized antibodies may, for example, be of murine antibodies or lama antibodies.

In some embodiments, the antibody molecule that specifically binds TNFR2 is a human IgG2 antibody molecule.

In some embodiments, the anti-TNFR2 antibody is an antibody in the form of a human IgG2 antibody showing improved binding to one or several inhibitory Fc receptors and/or being engineered for improved binding to one or several inhibitory Fc receptors; accordingly, in some embodiments, the anti-TNFR2 antibody is an Fc-engineered human IgG2 antibody.

In some embodiments, the anti-TNFR2 antibody is a murine or a humanized murine IgG3 antibody.

In some embodiments, the anti-TNFR2 antibody is a monoclonal antibody.

In some embodiments, the anti-TNFR2 antibody is a polyclonal antibody.

In some embodiments, the antibody molecule that specifically binds TNFR2 is human IgG1 antibody molecule, which corresponds to or a murine IgG2a.

In some embodiments, the antibody molecule that specifically binds TNFR2 comprises one of the VH-CDR1 sequences listed in Table 1 below.

In some embodiments, the antibody molecule that specifically binds TNFR2 comprises one of the VH-CDR2 sequences listed in Table 1 below.

In some embodiments, the antibody molecule that specifically binds TNFR2 comprises one of the VH-CDR3 sequences listed in Table 1 below.

In some embodiments, the antibody molecule that specifically binds TNFR2 comprises one of the VL-CDR1 sequences listed in Table 1 below In some embodiments, the antibody molecule that specifically binds TNFR2 cornprises one of the VL-CDR2 sequences listed in Table 1 below.

In some embodiments, the antibody molecule that specifically binds TNFR2 comprises one of the VL-CDR3 sequences listed in Table 1 below.

In some embodiments, the anti-TNFR2 antibody molecule is an antibody molecule selected from the group consisting of antibody molecules comprising 6 CDRs selected from the group consisting of:
SEQ. ID. NOs: 1, 2, 3, 4, 5 and 6;
SEQ. ID. NOs: 9, 10, 11, 12, 13 and 14;
SEQ. ID. NOs: 17, 18, 19, 20, 21 and 22;
SEQ. ID. NOs: 25, 26, 27, 28, 29 and 30;
SEQ. ID. NOs: 33, 34, 35, 36, 37 and 38;
SEQ. ID. NOs: 41, 42, 43, 44, 45 and 46;
SEQ. ID. NOs: 49, 50, 51, 52, 53 and 54;
SEQ. ID. NOs: 57, 58, 59, 60, 61 and 62;
SEQ. ID. NOs: 65, 66, 67, 68, 69 and 70;
SEQ. ID. NOs: 73, 74, 75, 76, 77 and 78;
SEQ. ID, NOs: 81, 82, 83, 84, 85 and 86;
SEQ. ID. NOs: 89, 90, 91, 92, 93 and 94; and
SEQ. ID. NOs: 97, 98, 99, 100, 101 and 102.

In some embodiments the anti-TNFR2 antibody molecule is an antibody molecule comprising the 6 CDRs having SEQ. ID. NOs: 1, 2, 3, 4, 5 and 6; or an antibody molecule comprising the 6 CDRs having SEQ. ID, NOs: 9, 10, 11, 12, 13 and 14; or an antibody molecule comprising the 6 CDRs having SEQ. ID. NOs: 17, 18, 19, 20, 21 and 22; or an antibody molecule comprising the 6 CDRs having SEQ. ID. NOs: 25, 26, 27, 28, 29 and 30; or an antibody molecule comprising the 6 CDRs having SEQ. ID. NOs: 33, 34, 35, 36, 37 and 38; or an antibody molecule comprising the 6 CDRs having SEQ. ID. NOs: 41, 42, 43, 44, 45 and 46.

In some embodiments the anti-TNFR2 antibody molecule is an antibody molecule comprising the 6 CDRs having SEQ. ID. NOs: 1, 2, 3, 4, 5 and 6.

In some embodiments, the anti-TNFR2 antibody molecule is an antibody molecule selected from the group consisting of antibody molecules comprising a VH selected from the group consisting of SEQ. ID, NOs: 7, 15, 23, 31, 39, 47, 55, 63, 71, 79, 87, 95 and 103.

In some embodiments, the anti-TNFR2 antibody molecule is an antibody molecule selected from the group consisting of antibody molecules comprising a VL selected from the group consisting of SEQ. ID. NOs: 8, 16, 24, 32, 40, 48, 56, 64, 72, 80, 88, 96 and 104.

In some embodiments the anti-TNFR2 antibody molecule is an antibody molecule comprising a VH having SEQ. ID. NO: 7, 15, 23, 31, 39 or 47.

In some embodiments the anti-TNFR2 antibody molecule is an antibody molecule comprising a VH having SEQ. ID. NO: 7.

In some embodiments it is preferred that the anti-TNFR2 antibody molecule is an antibody molecule comprising a VL having SEQ, ID. NO: 8, 16, 24, 32, 40 or 48.

In some embodiments, it is more preferred that the anti-TNFR2 antibody molecule is an antibody molecule comprising a VL having SEQ. ID. NO: 8.

In some embodiments, it is preferable that the anti-TNFR2 antibody molecule comprises a VH having SEQ. ID. NO: 7 and a VH having SEQ. ID, NO; 8.

In some embodiments the anti-TNFR2 antibody molecule comprises a CH having SEQ. ID, NO: 217.

In some embodiments the anti-TNFR2 antibody molecule comprises a CL having SEQ. ID. NO: 218.

In some embodiments the anti-TNFR2 antibody molecule comprises a VH having SEQ. ID. NO: 7, a VH having SEQ. ID. NO: 8, a CH having SEQ. ID. NO: 217 and a CL having SEQ. ID. NO: 218.

TABLE 1

Specific sequences of agonistic TNFR2 antibody molecules that do not block TNF-α binding to TNFR2 as described herein (in the VH and VL sequences, the CDR seuences are marked in bold text)

| Antibody clone | Region | Sequence | SEQ. ID. NO: |
|---|---|---|---|
| 001-F02 | VH-CDR1 | FSDYYMSWVRQAPG | 1 |
| | VH-CDR2 | ANINTDGSEKYYLDSVKGR | 2 |
| | VH-CDR3 | AREEYGAFDI | 3 |
| | VL-CDR1 | CSGSSSNIGSNTVN | 4 |
| | VL-CDR2 | DNNKRPS | 5 |
| | VL-CDR3 | CQSFDRGLSGSIV | 6 |
| | VH | EVQLLESGGGLVQPGGSLRLSCAASGFTFSDYYMSWVR-QAPGKGLEWVANINTDGSEKYYLDSVKGRFTISRD-NSKNTLYLQMNSLRAEDTAVYYCAREEYGAFD-IWGQGTLVTVSS | 7 |
| | VL | QSVLTQPPSASGTPGQRVTISCCSGSSS-NIGSNTVNWYQQLPGTAPKLLIYDNNKRPSGVPDRFSG-SKSGTSASLAISGLRSEDEADYYCQSFDR-GLSGSIVFGGGTKLTVLG | |
| 001-F06 | VH-CDR1 | FSSYAMHWVRQAPG | 9 |
| | VH-CDR2 | SAISGGATTTYYADSVKGR | 10 |
| | VH-CDR3 | AKGGTGDPYYFDY | 11 |
| | VL-CDR1 | CTGSSSNIGAGYDVH | 12 |
| | VL-CDR2 | RNNQRPS | 13 |
| | VL-CDR3 | CAARDDGLSGPV | 14 |
| | VH | EVQLLESGGGLVQPGGSLRLSCAASGFTFSSYAMHWVR-QAPGKGLEWVSAISGGATTTYYADSVKGRFTISRD-NSKNTLYLQMNSLRAEDTAVYYCAKGGTGDPYYFDYWGQGTLVTVSS | 15 |
| | VL | QSVLTQPPSASGTPGQRVTISCCTGSSSNI-GAGYDVHWYQQLPGTAPKLLIYRNNQRPSGVPDRFSG-SKSGTSASLAISGLR-SEDEADYYCAARDDGLSGPVFGGGTKLTVLG | 16 |
| 001-B05 | VH-CDR1 | FSNAWMSWVRQAPG | 17 |
| | VH-CDR2 | SSISSASGYIYYGDSVKGR | 18 |
| | VH-CDR3 | ARGTLYGDFDEF | 19 |
| | VL-CDR1 | CSGSSSNIGNNAVN | 20 |
| | VL-CDR2 | GNTNRPS | 21 |
| | VL-CDR3 | CQSYDSSLSGYVV | 22 |
| | VH | EVQLLESGGGLVQPGGSLRLS-CAASGFTFSNAWMSWVRQAPGKGLEWVSSISSASGYIY-YGDSVKGRFTISRD-NSKNTLYLQMNNLRAEDTAVYYCARGTLYGDFDEF-WGQGTLVTVSS | 23 |
| | VL | QSVLTQPPSASGTPGQRVTISCCSGSSS-NIGNNAVNWYQQLPGTAPKWYGNTNRPSGVPDRFSG-SKSGTSASLAISGLR-SEDEADYYCQSYDSSLSGYVVFGGGTKLTVLG | 24 |
| 001-C05 | VH-CDR1 | FSSNEMSWIRQAPG | 25 |
| | VH-CDR2 | SVIYSGGSTYYADSVKGR | 26 |
| | VH-CDR3 | ARREGWLVPFDY | 27 |
| | VL-CDR1 | CSGSSSNIGSNTVN | 28 |

TABLE 1-continued

Specific sequences of agonistic TNFR2 antibody molecules that do not block TNF-α binding to TNFR2 as described herein (in the VH and VL sequences, the CDR sequences are marked in bold text)

| Antibody clone | Region | Sequence | SEQ. ID. NO: |
|---|---|---|---|
| | VL-CDR2 | GNIIRPS | 29 |
| | VL-CDR3 | CQSFDTTLSGSIV | 30 |
| | VH | EVQLLESGGGLVQPGGSLRLSCAASGFTFSSNEMS-WIRQAPGKGLEWVSVIYSGGSTYYADSVKGRFTISRD-NSKNTLYLQMNSLRAEDTAVYYCARREG-WLVPFDYWGQGTLVTVSS | 31 |
| | VL | QSVLTQPPSASGTPGQRVTISCSGSSS-NIGSNTVNWYQQLPGTAPKWYGNIIRPSGVPDRFSG-SKSGTSASLAISGLR-SEDEADYYCQSFDTTLSGSVFGGGTKTVG | 32 |
| 004-E08 | VH-CDR1 | FSRYWMHWVRQVPG | 33 |
| | VH-CDR2 | SGISDSGVVTYYADSVKGR | 34 |
| | VH-CDR3 | ARAQSVAFDI | 35 |
| | VL-CDR1 | CSGSSSNIGAGHDVH | 36 |
| | VL-CDR2 | YDDLLPS | 37 |
| | VL-CDR3 | CAAWDDSLSGWV | 38 |
| | VH | EVQLLESGGGLVQPGGSLRLSCAASGFTFSRY-WMHWVRQVPGKGLEWVSGISDSGVVTY-YADSVKGRFTISRDNSKNTLYLQMNSLRAEDTAVYYCAR-AQSVAFDIWGQGTLVTVSS | 39 |
| | VL | QSVLTQPPSASGTPGQRVTISCSGSSSNIGAGH-DVHWYQQLPGTAPKLLIYYDDLLPSGVPDRFSG-SKSGTSASLAISGLR-SEDEADYYCAAWDDSLSGWVFGGGTKLTVLG | 40 |
| 001-G05 | VH-CDR1 | FSSYAMSWVRQAPG | 41 |
| | VH-CDR2 | SVISGSGGSTYYADAVKGR | 42 |
| | VH-CDR3 | TTDSGSGSYL | 43 |
| | VL-CDR1 | CTGSSSNIGAGYDVH | 44 |
| | VL-CDR2 | SNNQRPS | 45 |
| | VL-CDR3 | CAAWDDSLNGPV | 46 |
| | VH | EVQLLESGGGLVQPGGSLRLSCAASGFTFSSYAMSWVR-QAPGKGLEWVSVISGSGGSTYYADAVKGRFTISRD-NSKNTLYLQMNSLRAEDTAVYYCTT-DSGSGSYLWGQGTLVTVSS | 47 |
| | VL | QSVLTQPPSASGTPGQRVTISCTGSSSNI-GAGYDVHWYQQLPGTAPKLLIYSNNQRPSGVPDRFSG-SKSGTSASLAISGLR-SEDEADYYCAAWDDSLNGPVFGGGTKLTVLG | 48 |
| 001-A09 | VH-CDR1 | FSSNYMSWVRQAPG | 49 |
| | VH-CDR2 | SVISGSGGSTYYADSVKGR | 50 |
| | VH-CDR3 | ARDRGWFDP | 51 |
| | VL-CDR1 | CSGSRSNIDNSYVS | 52 |
| | VL-CDR2 | RNNQRPS | 53 |
| | VL-CDR3 | CATWDDSLSGPV | 54 |
| | VH | EVQLLESGGGLVQPGGSLRLSCAASGFTFSSNYMSWVR-QAPGKGLEWVSVISGSGGSTYYADSVKGRFTISRD-NSKNTLYLQMNSLRAEDTAVYYCARDRGWFDPWGQGTLVTVSS | 55 |
| | VL | QSVLTQPPSASGTPGQRVTISCSGSRSNIDNSYV-SWYQQLPGTAPKLLIYRNNQRPSGVPDRFSG-SKSGTSASLAISGLRSEDEADYY-CATWDDSLSGPVFGGGTKLTVLG | 56 |
| 001-B09 | VH-CDR1 | FSRHAMNWVRQAPG | 57 |
| | VH-CDR2 | SSISTGSSYIDYADSVKGR | 58 |
| | VH-CDR3 | AREKGHYYYGMDV | 59 |
| | VL-CDR1 | CTGSSSNIGAGYDVH | 60 |
| | VL-CDR2 | GNSYRPS | 61 |
| | VL-CDR3 | CQSYDTSLSAYVV | 62 |
| | VH | EVQLLESGGGLVQPGGSLRLSCAASGFTFSRHAMNWVR-QAPGKGLEWVSSISTGSSYIDYADSVKGRFTISRD-NSKNTLYLQMNSLRAEDTAVYYCAREKGHYYYG-MDVWGQGTLVTVSS | 63 |
| | VL | QSVLTQPPSASGTPGQRVTISCTGSSSNI-GAGYDVHWYQQLPGTAPKLLIYGNSYRPSGVPDRFSG-SKSGTSASLAISGLR-SEDEADYYCQSYDTSLSAYVVFGGGTKLTVLG | 64 |
| 001-O03 | VH-CDR1 | FSNAWMSWVRQAPG | 64 |
| | VH-CDR2 | SAISVSGINTYYADSVKGR | 66 |

TABLE 1-continued

Specific sequences of agonistic TNFR2 antibody molecules that do not block TNF-α binding to TNFR2 as described herein (in the VH and VL sequences, the CDR seuences are marked in bold text)

| Antibody clone | Region | Sequence | SEQ. ID. NO: |
|---|---|---|---|
| | VH-CDR3 | ARDTGSLGVDY | 67 |
| | VL-CDR1 | CSGSSSNIGSNTVN | 68 |
| | VL-CDR2 | RNNQRPS | 69 |
| | VL-CDR3 | CQSYDSSLSISV | 70 |
| | VH | EVQLLESGGGLVQPGGSLRLS-CAASGFTFSNAWMSWVRQAPGKGLEWVSAISVSGINTY-YADSVKGRFTISRD-NSKNTLYLQMNSLRAEDTAVYYCARDTGSLGVDYWGQGTLVTVSS | 71 |
| | VL | QSVLTQPPSASGTPGQRVTISCSGSSS-NIGSNTVNWYQQLPGTAPKLLIYRNNQRPSGVPDRFSG-SKSGTSASLAISGLR-SEDEADYYCQSYDSSSISVFGGGTKLTVLG | 72 |
| 001-A10 | VH-CDR1 | FSDYYMTWIRQAPG | 73 |
| | VH-CDR2 | SSISGGSTYYADSRKGR | 74 |
| | VH-CDR3 | AREPGYSYGFFDY | 75 |
| | VL-CDR1 | CTGSSSNIGAGYDVH | 76 |
| | VL-CDR2 | SNNQRPS | 77 |
| | VL-CDR3 | CQSYDRSLSGSIV | 78 |
| | VH | EVQLLESGGGLVQPGGSLRLS-CAASGFTFSDYYMIRQAPGKGLEWVSSISGGSTY-YADSRKGRFTISRD-NSKNTLYLQMNSLRAEDTAVYYCAREPGY-SYGFFDYWGQGTLVTVSS | 79 |
| | VL | QSVLTQPPSASGTPGQRVTISCTGSSSNI-GAGYDVHWYQQLPGTAPKLLIYSNNQRPSGVPDRFSG-SKSGTSASLAISGLR-SEDEADYYCQSYDRSSGSIVFGGGTKLTVLG | 80 |
| 001-C06 | VH-CDR1 | SSSYWMSWVRQAPG | 81 |
| | VH-CDR2 | SAISGSGGSTYYADSVKGR | 82 |
| | VH-CDR3 | AREYSGYEFDF | 83 |
| | VL-CDR1 | CTGSSSNIGARSDVH | 84 |
| | VL-CDR2 | GNRNRPS | 85 |
| | VL-CDR3 | CQSFDRGLSGSIV | 86 |
| | VH | EVQLLESGGGLVQPGGSLRLSCAASGFTSSSYWMSWVR-QAPGKGLEWVSAISGSGGSTYYADSVKGRFTISRD-NSKNTLYLQMNSLRAEDTAVYYCAR-EYSGYEFDFWGQGTLVTVSS | 87 |
| | VL | QSVLTQPPSASGTPGQRVTISCTGSSSNI-GARSDVHWYQQLPGTAPKLLIYGNRNRPSGVPDRFSG-SKSGTSASLAISGLRSEDEADYYCQSFDR-GLSGSIVFGGGTKLTVLG | 88 |
| 001-H03 | VH-CDR1 | FSSNYMSWVRQAPG | 89 |
| | VH-CDR2 | SSISSSSSYIYYADSVKGR | 90 |
| | VH-CDR3 | ARDRGRTGTDY | 91 |
| | VL-CDR1 | CSGTTSNIGSYAVN | 92 |
| | VL-CDR2 | GNINRPS | 93 |
| | VL-CDR3 | CQSYDSSLSASL | 94 |
| | VH | EVQLLESGGGLVQPGGSLRLSCAASGFTFSSNYMSWVR-QAPGKGLEWVSSISSSSSYIYYADSVKGRFTISRD-NSKNTLYLQMNSLRAEDTAVYYCARDRGRT-GTDYWGQGTLVTVSS | 95 |
| | VL | QSVLTQPPSASGTPGQRVTISCSGTTSNIGSYAVNWYQQLPGTAPKLLIYGNINRPSGVPDRFSGSKSGTSASLAISGLR-SEDEADYYCQSYDSSLSASLFGGGTKLTVLG | 96 |
| 005-A05 | VH-CDR1 | FSSYAMSWVRQAPG | 97 |
| | VH-CDR2 | STIIGSGANTWYADSVKGR | 98 |
| | VH-CDR3 | ARHEGYYYYGMDV | 99 |
| | VL-CDR1 | CTGSSSNIGAGYVVH | 100 |
| | VL-CDR2 | GNSNRPS | 101 |
| | VL-CDR3 | CAAWDDSLNGRV | 102 |
| | VH | EVQLLESGGGLVQPGGSLRLSCAASGFTFSSYAMSWVR-QAPGKGLEWVSTIIGSGANTADSVKGRFTISRD-NSKNTLYLQMNSLRAEDTAVYYCARHEGYYYYG-MDVWGQGTLVTVSS | 103 |

TABLE 1-continued

Specific sequences of agonistic TNFR2 antibody molecules that do not block TNF-α binding to TNFR2 as described herein (in the VH and VL sequences, the CDR seuences are marked in bold text)

| Antibody clone | Region | Sequence | SEQ. ID. NO: |
|---|---|---|---|
| | VL | QSVLTQPPSASGTPGQRVTISCTGSSSNI-GAGYVVHWYQQLPGTAPKLLIYGNSNRPSGVPDRFSG-SKSGTSASLAISGLR-SEDEADYYCAAWDDSLNGRVFGGGTKLTVLG | 104 |

In order to determine or demonstrate the features of the antibody molecules of the present invention, they were compared to antibody molecules that block TNF-α, from binding to TNFR2. Such antibodies are shown in Table 2.

TABLE 2

Specific sequences of blocking TNFR2 antibody molecules mentioned herein as reference antibodies (in the VH and VL sequences, the CDR sequences are marked in bold text)

| Antibody clone | Region | Sequence | SEQ. ID. NO: |
|---|---|---|---|
| 001-H10 | VH-CDR1 | FDDYGMSWVRQAPG | 105 |
| | VH-CDR2 | SVIYSGGSTYYADSVKGR | 106 |
| | VH-CDR3 | CARDRSSSWYRDGMDV | 107 |
| | VL-CDR1 | CTGSSSNIGAGYDVH | 108 |
| | VL-CDR2 | GNSNRPS | 109 |
| | VL-CDR3 | CAAWDDSLSGWV | 110 |
| | VH | EVQLLESGGGLVQPGGSLRLSCAASGFTFDDYGMSWVR-QAPGKGLEWVSVIYSGGSTYYADSVKGRFTISRD-NSKNTLYLQMNSLRAEDTAVYYCARDRSSS-WYRDGMDVWGQGTLVTVSS | 111 |
| | VL | QSVLTQPPSASGTPGQRVTISCTGSSSNI-GAGYDVHWYQQLPGTAPKLLIYGNSNRPSGVPDRFSG-SKSGTSASLAISGLR-SEDEADYYCAAWDDSLSGWVFGGGTKLTVLG | 112 |
| 004-H02 | VH-CDR1 | FDDYGMSWVRQAPG | 113 |
| | VH-CDR2 | STIYSGDNAYYGASVRGR | 114 |
| | VH-CDR3 | ARVYSSSWRKRAFDI | 115 |
| | VL-CDR1 | CSGTSSNIESNTVN | 116 |
| | VL-CDR2 | SDNQRPS | 117 |
| | VL-CDR3 | CAAWDDSLSGWV | 118 |
| | VH | EVQLLESGGGLVQPGGSLRLSCAASGFTFDDYGMSWVR-QAPGKGLEWVSTIYSGDNAYYGASVRGRFTISRD-NSKNTLYLQMNSLRAEDTAVYYCARVYSSSWRKRAFD-IWGQGTLVTVSS | 119 |
| | VL | QSVLTQPPSASGTPGQRVTISCSGTSSNI-ESNTVNWYQQLPGTAPKLLIYSDNQRPSGVPDRFSG-SKSGTSASLAISGLR-SEDEADYYCAAWDDSLSGWVFGGGTKLTVLG | 120 |
| 005-B02 | VH-CDR1 | FSDYYMSWIRQAPG | 121 |
| | VH-CDR2 | ALIWYDGGNEYYADSVKGR | 122 |
| | VH-CDR3 | VRETGNYGMDV | 123 |
| | VL-CDR1 | CTGSSSNIGAGYDVH | 124 |
| | VL-CDR2 | RNNQRPS | 125 |
| | VL-CDR3 | CATWDDRVNGPV | 126 |
| | VH | EVQLLESGGGLVQPGGSLRLS-CAASGFTFSDYYMSWIRQAPGKGLEWVALIWYDGGNEY-YADSVKGRFTISRD-NSKNTLYLQMNSLRAEDTAVYYCVRETGNYGMDVWGQGTLVTVSS | 127 |
| | VL | QSVLTQPPSASGTPGQRVTISCTGSSSNI-GAGYDVHWYQQLPGTAPKLLIYRNNQRPSGVPDRFSG-SKSGTSASLAISGLRSEDEADYY-CATWDDRVNGPVFGGGTKLTVLG | 128 |
| 005-B08 | VH-CDR1 | FSDYYMSWIRQAPG | 129 |
| | VH-CDR2 | AIISYDGGGKYFADPVKGR | 130 |
| | VH-CDR3 | ARYYGDGGFDP | 131 |
| | VL-CDR1 | CTGSSSNIGAGYVVH | 132 |
| | VL-CDR2 | SNNQRPS | 133 |
| | VL-CDR3 | CAAWDDSLNGPV | 134 |
| | VH | EVQLLESGGGLVQPGGSLRLS- | 135 |

TABLE 2-continued

Specific sequences of blocking TNFR2 antibody molecules mentioned herein as reference antibodies (in the VH and VL sequences, the CDR sequences are marked in bold text)

| Antibody clone | Region | Sequence | SEQ. ID. NO: |
|---|---|---|---|
| | | CAASGFTFSDYYMSWIRQAPGKGLEWVAIISYDGGGKY-FADPVKGRFTISRD-NSKNTLYLQMNSLRAEDTAVYYCARYYG-DGGFDPWGQGTLVTVSS | |
| | VL | QSVLTQPPSASGTPGQRVTISCTGSSSNI-GAGYVVHWYQQLPGTAPKLLIYSNNQRPSGVPDRFSG-SKSGTSASLAISGLR-SEDEADYYCAAWDDSLNGPVFGGGTKLTVLG | 136 |
| 001-E06 | VH-CDR1 | FSSNYMSWVRQAPG | 137 |
| | VH-CDR2 | ALIWYDGSNKYYADSVKGR | 138 |
| | VH-CDR3 | AKDPLFDS | 139 |
| | VL-CDR1 | CTGRSSNIGAGYDVH | 140 |
| | VL-CDR2 | DNNKRPS | 141 |
| | VL-CDR3 | CAAWDDSLNGPV | 142 |
| | VH | EVQLLESGGGLVQPGGSLRLSCAASGFTFSSNYMSWVR-QAPGKGLEWVALIWYDGSNKYYADSVKGRFTISRD-NSKNTLYLQMNSLRAEDTAVYYCAKDPLFDSWGQGTLVTVSS | 143 |
| | VL | QSVLIQPPSASGTPGQRVTISCTGRSSNI-GAGYDVHWYQQLPGTAPKLLIYDNNKRPSGVPDRFSG-SKSGTSASLAISGLR-SEDEADYYCAAWDDSLNGPVFGGGTKLTVLG | 144 |
| 001-G04 | VH-CDR1 | FNTYSMNWVRQAPG | 145 |
| | VH-CDR2 | SVLYSDDDTHYADSVKGR | 146 |
| | VH-CDR3 | ARDCGGDCHSGDDAFDI | 147 |
| | VL-CDR1 | CSGSSSNIGSNTVN | 148 |
| | VL-CDR2 | DNDKRPS | 149 |
| | VL-CDR3 | CAAWHDSLNGWV | 150 |
| | VH | EVQLLESGGGLVQPGGSLRLSCAASGFTFNTYSMNWVR-QAPGKGLEWVSVLYSDDDTHYADSVKGRFTISRD-NSKNTLYLQMNSLRAEDTAVYYCARDCGG-DCHSGDDAFDIWGQGTLVTVSS | 151 |
| | VL | QSVLTQFPSASGTPGQRVTISCSGSSS-NIGSNTVNWYQQLPGTAPKLLIYDNDKRPSGVPDRFSG-SKSGTSASLAISGLR-SEDEADYYCAAWHDSLNGWVLGGGTKLTVLG | 152 |
| 001-G10 | VH-CDR1 | FSAYGMHWVRQAPG | 153 |
| | VH-CDR2 | AVVSYDGREKHYADSVKGR | 154 |
| | VH-CDR3 | ARSDGGYDSDSGYY | 155 |
| | VL-CDR1 | CSGSTSNIGSNFVY | 156 |
| | VL-CDR2 | DNNKRPS | 157 |
| | VL-CDR3 | CSSYAYSDNIL | 158 |
| | VH | EVQLLESGGGLVQPGGSLRLSCAASGFTFSAYGMHWVR-QAPGKGLEWVAVVSYDGREKHYADSVKGRFTISRD-NSKNTLYLQMNSLRAEDTAVYYCARSDG-GYDSDSGYYWGQGTLVTVSS | 159 |
| | VL | QSVLTQPPSASGTPGQRVTISCSGSTSNIGSNFVY-WYQQLPGTAPKLLIYDNNKRPSGVPDRFSG-SKSGTSASLAISGLRSEDEADYYCS-SYAYSDNILFGGGTKLTVLG | 160 |
| 001-C08 | VH-CDR1 | FSNAWMSWVRQAPG | 161 |
| | VH-CDR2 | SGISSSGSSAYYADSVKGR | 162 |
| | VH-CDR3 | ARHYYYHIAGYYYDTFDI | 163 |
| | VL-CDR1 | CSGSSSNIGGNTVN | 164 |
| | VL-CDR2 | GNTNRPS | 165 |
| | VL-CDR3 | CAAWDDSLSGVV | 166 |
| | VH | EVQLLESGGGLVQPGGSLRLS-CAASGFTFSNAWMSWVRQAPGKGLEWVSGISSSGS-SAYYADSVKGRFTISRD-NSKNTLYLQMNSLRAEDTAVYYCARHYYYHIAGYYYDTFD-IWGQGTLVTVSS | 167 |
| | VL | QSVLTQPPSASGTPGQRVTISCSGSSS-NIGGNTVNWYQQLPGTAPKLLIYGNTNRPSGVPDRFSG-SKSGTSASLAISGLR-SEDEADYYCAAWDDSLSGVVFGGGTKLTVLG | 168 |
| 001-H09 | VH-CDR1 | FSSYAMSWVRQAPG | 169 |
| | VH-CDR2 | ATISYHGSDKDYADSVKGR | 170 |
| | VH-CDR3 | ARDANYHSSGYYYDVFDI | 171 |

TABLE 2-continued

Specific sequences of blocking TNFR2 antibody molecules mentioned herein as reference antibodies (in the VH and VL sequences, the CDR sequences are marked in bold text)

| Antibody clone | Region | Sequence | SEQ. ID. NO: |
|---|---|---|---|
| | VL-CDR1 | CSGSSSNIGSNTVN | 172 |
| | VL-CDR2 | GNSNRPS | 173 |
| | VL-CDR3 | CAAWDDSLSTWV | 174 |
| | VH | EVQLLESGGGLVQPGGSLRLSCAASGFTFSSYAMSWVR-QAPGKGLEWVATISYHGSDKDYADSVKGRFTISRD-NSKNTLYLQMNSLRAEDTAVYYCARDANY-HSSGYYYDVFDIWGQGTLVTVSS | 175 |
| | VL | QSVLTQPPSASGTPGQRVTISCSGSSS-NIGSNTVNWYQQLPGTAPKLLIYGNSNRPSGVPDRFSG-SKSGTSASLAISGLR-SEDEADYYCAAWDDSLSTWVFGGGTKLTVLG | 176 |
| 005-F10 | VH-CDR1 | FSDYYMTWIRQAPG | 177 |
| | VH-CDR2 | SGISGSGGYIHYADSVKGR | 178 |
| | VH-CDR3 | AREGLLPDAFD | 179 |
| | VL-CDR1 | CSGSSSNIGNNYVS | 180 |
| | VL-CDR2 | RNNQRPS | 181 |
| | VL-CDR3 | CAAWDDSVSGWV | 182 |
| | VH | EVQLLESGGGLVQPGGSLRLS-CAASGFTFSDYYMTWIRQAPGKGLEWVSGISGSGGYIHY-ADSVKGRFTISRD-NSKNTLYLQMNSLRAEDTAVYYCAREGLLPDAFD-IWGQGTLVTVSS | 183 |
| | VL | QSVLTQPPSASGTPGQRVTISCSGSSS-NIGNNYVSWYQQLPGTAPKLLIYRNNQRPSGVPDRFSG-SKSGTSASLAISGLR-SEDEADYYCAAWDDSVSGWVFGGGTKLTVLG | 184 |
| 001-B11 | VH-CDR1 | FSSYSMNWVRQAPG | 185 |
| | VH-CDR2 | AVMSYDEYNTYYADSVKGR | 186 |
| | VH-CDR3 | AKGFYGDYPLWDY | 187 |
| | VL-CDR1 | CSGGNSNIGTNTVD | 188 |
| | VL-CDR2 | SNNQRPS | 189 |
| | VL-CDR3 | CAAWDDSVNGPV | 190 |
| | VH | EVQLLESGGGLVQPGGSLRLSCAASGFTFSSYSMNWVR QAPGKGLEWAVMSYDEYNTYYADSVKGRFTISRD-NSKNTLYLQMNSLRAEDTAVYYCAKGFYGDY-PLWDYWGQGTLVTVSS | 191 |
| | VL | QSVLTQPPSASGTPGQRVTISCSGGNSNIGTNTVDWYQQL PGTAPKWYSNNQRPSGVPDRFSGSKSGTSASLAISGLR-SEDEADYYCAAWDDSVNGPVFGGGTKLTVLG | 192 |
| 001-C07 | VH-CDR1 | FSSYEMNWVRQAPG | 193 |
| | VH-CDR2 | STITGGGSIYDANSVQGR | 194 |
| | VH-CDR3 | ARDSTYHSSGYYYDVFDI | 195 |
| | VL-CDR1 | CSGSSSNIGSNTVN | 196 |
| | VL-CDR2 | GNSNRPS | 197 |
| | VL-CDR3 | CAAWDDSLSGHWV | 198 |
| | VH | EVQLLESGGGLVQPGGSLRLSCAASGFTFSSYEMNWVR-QAPGKGLEWVSTITGGGSIYDANSVQGRFTISRD-NSKNTLYLQMNSLRAEDTAVYYCARDSTYHSSGYYYDVFD IWGQGTLVTVSS | 199 |
| | VL | QSVLTQPPSASGTPGQRVTISCSGSSS-NIGSNTVNWYQQLPGTAPKLLIYGNSNRPSGVPDRFSG-SKSGTSASLAISGLRSEDEADYYCAAWDDSLSGH-WVFGGGTKLTVLG | 200 |
| 001-D01 | VH-CDR1 | FSSYGMHWVRQAPG | 201 |
| | VH-CDR2 | SAVFGSGHGNTFYADAVKGR | 202 |
| | VH-CDR3 | AREQLWFGQDAFDI | 203 |
| | VL-CDR1 | CSGSSSNIGSNTVN | 204 |
| | VL-CDR2 | GNSNRPS | 205 |
| | VL-CDR3 | CQSYDSSLSASV | 206 |
| | VH | EVQLLESGGGLVQPGGPLRLSCAASGFTFSSYGMHWVR-QAPGKGLEWVSAVFGSGHGNTFYADAVKGRFTISRD-NSKNTLYLQMNSLRAEDTAVYYCAREQLWFGQDAFD-IWGQGTLVTVSS | 207 |
| | VL | QSVLTQPPSASGTPGQRVTISCSGSSS-NIGSNTVNWYQQLPGTAPKLLIYGNSNRPSGVPDRFSG-SKSGTSASLAISGLR-SEDEADYYCQSYDSSLSASVFGGGTKLTVLG | 208 |

TABLE 2-continued

Specific sequences of blocking TNFR2 antibody molecules mentioned herein as reference antibodies (in the VH and VL sequences, the CDR sequences are marked in bold text)

| Antibody clone | Region | Sequence | SEQ. ID. NO: |
|---|---|---|---|
| 003-F10 | VH-CDR1 | FSDAWMTWVRQAPG | 209 |
|  | VH-CDR2 | SDLSDSGGSTYYADSVKGR | 210 |
|  | VH-CDR3 | GRLAAGGPVDY | 211 |
|  | VL-CDR1 | CTGSSSNIGAGYDVH | 212 |
|  | VL-CDR2 | SNNQRPS | 213 |
|  | VL-CDR3 | CSVWDDSLNSWV | 214 |
|  | VH | EVQLLESGGGLVQPGGSLRLSCAASGFTFSDAWMTWVR-QAPGKGLEWVSDLSDSGGSTYYADSVKGRFTISRD-NSKNTLYLQMNSLRAEDTAVYYCGRLAAGGPVDYWGQGTLVTVSS | 215 |
|  | VL | QSVLTQPPSASGTPGQRVTISCTGSSSNI-GAGYDVHWYQQLPGTAPKLLIYSNNQRPSGVPDRFSG-SKSGTSASLAISGLR-SEDEADYYCSVWDDSLNSWVFGGGTKTVLG | 216 |

The sequences in Tables 1 and 2 above are all of human origin and derived from the n-CoDeR® library, as explained in detail in Example 1.

In some embodiments, the antibody molecules that specifically bind TNFR2 described herein may also comprise one or both of the constant regions (CH and/or CL) listed in Table 3 below.

The first CH (SEQ. ID. NO: 217) and the first CL (SEQ. ID. NO: 218) sequences in Table 3 above are of human origin. The second CH (SEQ. ID. NO: 219) and the third CH (SEQ. ID. NO: 220) in Table 3 are both from murine IgG2a, with that difference that the third CH sequence (SEQ. ID. NO: 220) contains an N297A mutation. The second CL sequence (SEQ. ID. NO: 221) is from murine lambda light

TABLE 3

| Region | Sequence | SEQ. ID. NO: |
|---|---|---|
| CH | ASTKGPSVFPLAPSSKSTSGG-TAALGCLVKDYFPEPVTVSWNSGALTSGVHTFPAVLQSSGLYS-LSSVVTVPSSSLGTQTYICNVNHKPSNTKVDKKVE-PKSCDKTHTCPPCPAPELLGGPSVFLFPPKPKDTLMIS-RTPEVTCVVVDVSHEDPEVKFNWYVDGVEVHNAK-TKPREEQYNSTYRVVSVLTVLHQDWLNGKEYKCKVSNKALPA-PIEK-TISKAKGQPREPQVYTLPPSRDELTKNQVSLTCLVKGFYPSDI-AVEWESNGQPENNYKTTPPVLDSDGS-FFLYSKLTVDKSRWQQGNVFSCSVMHEALHNHYTQKSLSL-SPGK | 217 |
| CL | QPKAAPSVTLFPPSSEELQANKATLVCLISDFYPGAVTVAW-KADSSPVKAGVETTTPSKQSNNKYAASSYLSLT-PEQWKSHRSYSCQVTHEGSTVEKTVAPTECS | 218 |
| CH | AKTTAPSVYPLAPVCGDTTGSSVTLGCLVKGYFPEPVTLT-WNSGSLSSGVHTFPAVLQSDLYTLSSSVTVTSSTWPSQSIT-CNVAHPASSTKVDKKIEPRGPTIKPCPPCKCPAPNLLGGPSVFIFPPKIK-DVLMISLSPIVTCVVVDVSEDDPDVQISWFVNNVEVHTAQ-TQTHREDYNSTLRVVSALPIQHQDWMSGKEFKCKVNNKDLPAPIERTI-SKPKGSVRAPQVYVLPPPEEEMTKKQVTLTCMVTDFMPEDIYVEWTN-NGKTELNYKNTEPVLDSDGSYFMYSKLRVEKKNWVERN-SYSCSVVHEGLHNHHTTKSFSRTPGK | 219 |
| CH | AKTTAPSVYPLAPVCGDTTGSSVTLGCLVKGYFPEPVTLT-WNSGSLSSGVHTFPAVLQSDLYTLSSSVTVTSSTWPSQSIT-CNVAHPASSTKVDKKIEPRGPTIKPCPPCKCPAPNLLGGPSVFIFPPKIK-DVLMISLSPIVTCVVVDVSEDDPDVQISWFVNNVEVHTAQ-TQTHREDYASTLRVVSALPIQHQDWMSGKEFKCKVNNKDLPAPIERTI-SKPKGSVRAPQVYVLPPPEEEMTKKQVTLTCMVTDFMPEDIYVEWTN-NGKTELNYKNTEPVLDSDGSYFMYSKLRVEKKNWVERN-SYSCSVVHEGLHNHHTTKSFSRTPGK | 220 |
| CL | QPKSSPSVTLFPPSSEELETNKA-TLVCTITDFYPGVVTVDWKVDGTPVTQGMETTQPSKQSNNKY-MASSYLTLTARAWERHSSYSCQVTHEGHTVEKSLSRADCS | 221 | chain constant region. These murine sequences are used in the examples for the surrogate antibodies.

In some embodiments, the antibody molecules bind human TNFR2 (hTNFR2), In some embodiments, it is preferred that the agonistic antibody molecules bind strongly to human TNFR2, i.e. that they have a low EC50 value. This is demonstrated further in Example 2.

In some embodiments, it is advantageous that the antibody molecule binds both to hTNFR2 and to cynomologus monkey TNFR2 (cmTNFR2 or cynoTNFR2). Cross-reactivity with TNFR2 expressed on cells in cynomolgus monkey, also called crab-eating macaque or *Macaca fascicularis*, may be advantageous since this enables animal testing of the antibody molecule without having to use a surrogate antibody, with particular focus on tolerability.

In some embodiments, it is necessary to use a surrogate antibody to test an anti-body molecule's functional activity in relevant in vivo models in mice. To ensure the comparability between the antibody molecule's effect in humans and the in vivo results for the surrogate antibody in mice, it is essential to select a functionally equivalent surro-gate antibody having the same in vitro characteristics as the human antibody molecule. In some embodiments, the antibody molecule does not bind specifically to an epitope of TNFR2 comprising or consisting of the sequence KCSPG (SEQ ID NO: 224).

In some embodiments, the antibody molecule of the present invention or used according to the invention is an antibody molecule that is capable of competing with the specific antibodies provided herein, for example capable of competing with antibody molecules comprising a VH selected from the group consisting of SEQ. ID. NOs; 7, 15, 23, 31, 39, 47, 55, 63, 71, 79, 87, 95 and 103; and/or a VL selected from the group consisting of SEQ. ID. NOs: 8, 16, 24, 32, 40, 48, 56, 64, 72, 80, 88, 96 and 104, for binding to TNFR2.

By "capable of competing for" we mean that the competing antibody is capable of inhibiting or otherwise interfering, at least in part, with the binding of an antibody molecule as defined herein to the specific target TNFR2.

For example, such a competing antibody molecule may be capable of inhibiting the binding of an antibody molecule described herein to TNRF2 by at least about 10%; for example at least about 20%, or at least about 30%, at least about 40%, at least about 50%, at least about 60%, at least about 70%, at least about 80%, at least about 90%, at least about 95%, or about 100%.

Competitive binding may be determined by methods well known to those skilled in the art, such as Enzyme-linked immunosorbent assay (ELISA).

ELISA assays can be used to evaluate epitope-modifying or blocking antibodies. Additional methods suitable for identifying competing antibodies are disclosed in Antibodies: A Laboratory Manual, Harlow & Lane, which is incorporated herein by reference (for example, see pages 567 to 569, 574 to 576, 583 and 590 to 612, 1988, CSHL, NY, ISBN 0-87969-314-2).

In some embodiments, it is of interest to use not the antibody molecule itself but a nucleotide sequence encoding such an antibody molecule. The present invention thus encompasses nucleotide sequences encoding the above agonistic, non-blocking TNFR-2 antibody molecules.

The above described agonistic, non-blocking antibody molecules and nucleotide sequences can be used in medicine, and then such an antibody molecule and/or nucleotide sequence can be included in a pharmaceutical composition, as discussed further below.

The above described agonistic, non-blocking antibody molecules, nucleotide sequences and/or pharmaceutical compositions can be used in the treatment of cancer, as discussed further below.

The above described agonistic, non-blocking antibody molecules, nucleotide sequences and/or pharmaceutical compositions can be used in the treatment of a chronic inflammatory disease, as discussed further below.

The above described agonistic, non-blocking antibody molecules and/or nucleotide sequences can be used in the manufacture of a pharmaceutical composition for use in the treatment of cancer.

The above described agonistic, non-blocking antibody molecules and/or nucleotide sequences can be used in the manufacture of a pharmaceutical composition for use in the treatment of a chronic inflammatory disease.

The above described agonistic, non-blocking antibody molecules and/or pharmaceutical compositions can be used in a method for treatment of cancer in a patient, wherein a therapeutically effective amount of an antibody molecule or pharmaceutical composition is administered to the subject.

The above described agonistic, non-blocking antibody molecules and/or pharmaceutical compositions can be used in a method for treatment of a chronic inflammatory disease in a patient, wherein a therapeutically effective amount of an antibody molecule or pharmaceutical composition is administered to the patient.

In some embodiments relating to treatment of cancer, the cancer is a solid cancer or a leukemic cancer. A solid tumor is an abnormal mass of tissue that usually does not contain cysts or liquid areas. Solid tumors may be benign (not cancer), or malignant (cancer). Malignant solid tumors are herein denoted solid cancer, Different types of solid tumors or cancer are named for the type of cells that form them. Examples of solid tumars are sarcomas, carcinomas, and lymphomas.

More specific examples of solid cancers are lung cancer, head and neck cancer, gastric cancer, breast cancer, colorectal cancer, prostate cancer, bladder cancer, ovarian cancer, endometrial cancer, kidney cancer, liver cancer, pancreatic cancer, thyroid cancer, brain cancer, central nervous system cancer, melanoma, neuroblastoma, lymphoma, Wilms tumor, rhabdomyosarcoma, retinoblastoma and bone cancer.

More specific examples of leukemic cancers are acute lymphocytic leukemia, Chronic myeloproliferative disease, acute non-lymphocytic leukemia, B cell acute lymphocytic leukemia, chronic lymphocytic leukemia, T cell acute lymphocytic leukemia, non-Hodgkin lymphomas and chronic lymphoproliferative diseases. In some embodiments, the above described agonistic, non-blocking antibody molecules can be used in combination with an antibody molecule that specifically binds to a check-point inhibitor. Alternatively, the above discussed nucleotide sequences encoding an agonistic, non-blocking TNFR2 antibody molecule can be used in combination with antibody molecule that specifically binds to a check-point inhibitor or a co-stimulatory agonistic antibody. Examples of antibodies to check-point inhibitors are antibodies targeting CTLA4, PD1, PD-L1, VISTA, TIGIT, CD200, CD200R, BTLA, LAGS, TIM3, B7-H3, B7-H4, B7-H7. Examples of co-stimulatory agonistic antibodies are antibodies targeting OX40, 41BB, OX40L, 41BBL, GITR, ICOS, DR3, DR4, DR5, CD40, CD27, RANK, HVEM, LIGHT and B7-H6. Alternatively, the above discussed agonistic, non-blocking TNFR2 antibody molecules can be used in combination with a nucleotide sequence encoding an antibody molecule that specifically binds to a check-point inhibitor or a co-stimulatory agonist.

Alternatively, the above discussed nucleotide sequences encoding an agonistic, non-blocking TNFR2 antibody molecule can be used in combination with a nucleotide sequence that encodes an antibody molecule that specifically binds to a check-point inhibitor or a costimulatory agonist. In some such embodiments, the antibody molecule that specifically binds to a check-point inhibitor is an anti-PD-1 antibody. PD1 antibodies are thought to block the inhibitory signal mediated through PD-L1, primarily in CD8$^+$ T cells; and thereby allowing an increased T cell mediated anti-tumor response. These treatments could synergize with each other. The same is true for other check-point inhibitors and agonistic costimulatory antibodies Additionally, the above discussed agonistic non-blocking TNFR2 antibody molecules can be used in combination with other anti-cancer treatments such as chemotherapy (e.g. but not limited to doxorubicin, paraplatin, cyclophosphamide, paclitaxel, gemcitabine, 5-fluorouracil, docetaxel, vincristine, Mitoxantrone, mutamycin, epirubicin and methotrexate), small molecule tyrosin kinase or serine/threonine kinase inhibitors (e.g. but not limited to ibrutinib, imatinib, suntinib, regorafenib, sorafenib, dasatinib, erlotinib, vandetanib, midostaurin, vemurafenib, dabrafenib, palbociclib, ribociclib, Trametinib or alectinib), inhibitors targeting growth factor receptors (e.g. but not limited to drugs targeting EGFR/HER1/ErbB1, EGFR2/HER2/ErbB2, EGFR3/HER3/ErbB3, VEGFR, PDGFR HGFR, RET, insulin-like growth factor receptor IGFR, FGFR), anti-angiogenic agents (e.g. but not limited to Bevacizumab, Everolimus, Lenalidomide, Thalidomide, Ziv-aflibercept) or irradiation. Typically, the above mentioned anti-cancer drugs all cause cancer cell death which will lead to exposure of neo-antigens and inflammation. At a time where neo-antigens are exposed, and there is an influx of inflammatory cells in the tumor, there can occur synergistic effects of the anti-cancer drug.

It would be known to the person skilled in medicine, that medicines can be modified with different additives, for example to change the rate in which the medicine is absorbed by the body; and can be modified in different forms, for example to allow for a particular administration route to the body.

Accordingly, we include that the agonistic, non-blocking antibody molecules, nucleotide sequences, plasmids, viruses and/or cells described herein may be combined with a pharmaceutically acceptable excipient, carrier, diluent, vehicle and/or adjuvant into a pharmaceutical composition. In this context, the term pharmaceutical composition can be used interchangeably with the terms pharmaceutical preparation, pharmaceutical formulation, therapeutic composition, therapeutic preparation, therapeutic formulation and therapeutic entity.

The pharmaceutical compositions described herein may comprise, or in some embodiments consist of, antibody molecules, nucleotide sequences, plasmids, viruses or cells.

The pharmaceutical compositions described herein may in some embodiments consist of or comprise plasmids comprising nucleotide sequences encoding the above described antibody molecules or comprising the above described nucleotide sequences.

In some embodiments, the pharmaceutical compositions may comprise nucleotide sequences encoding parts of or a complete antibody molecule described herein integrated in a cell or viral genome or in a viriome. The pharmaceutical composition may then comprise a cell or a virus as a delivery vehicle for an antibody of the invention (or a delivery vehicle for a nucleotide sequence encoding an antibody of the invention). For example, in an embodiment, the virus may be in the form of a therapeutic oncolytic virus comprising nucleotide sequences encoding at least one of the antibody molecules described herein. In some embodiments, such an oncolytic virus comprises nucleotide sequences encoding a full-length human IgG antibody. In some embodiments, such an oncolytic virus comprises nucleotide sequences encoding an scFv, Fab or F(ab')$_2$ antibody molecule.

As described in the accompanying claims, in some embodiments the invention relates to a virus comprising a nucleotide sequence of the invention or a plasmid of the invention. Preferably, the virus is an oncolytic virus, such as a therapeutic oncolytic virus. Such viruses are known to those skilled in the arts of medicine and virology.

In some embodiments, such an oncolytic virus comprises nucleotide sequences encoding amino acid sequence having at least 80% identity with a sequence set out in table 1 above. In some embodiments, such an oncolytic virus comprises an amino acid sequence having at least 85% identity with a sequence set out in table 1 above. In some embodiments, such an oncolytic virus comprises an amino acid sequence having at least 90% identity with a sequence set out in table 1 above. In some embodiments, such an oncolytic virus comprises an amino acid sequence having at least 95% identity with a sequence set out in table 1 above.

In some embodiments, such an oncolytic virus comprises nucleotide sequences encoding SEQ. ID. NO: 7 and ID. NO: 8. In some embodiments, such an oncolytic virus comprises nucleotide sequences encoding SEQ. ID. NO: 15 and ID. NO: 16. In some embodiments, such an oncolytic virus comprises nucleotide sequences encoding SEQ. ID. NO: 23 and ID. NO: 24. In some embodiments, such an oncolytic virus comprises nucleotide sequences encoding SEQ. ID. NO: 31 and ID. NO: 32. In some embodiments, such an oncolytic virus comprises nucleotide sequences encoding SEQ. ID. NO: 39 and ID. NO: 40. In some embodiments, such a oncolytic virus comprises nucleotide sequences encoding SEQ. ID. NO: 47 and ID. NO: 48. In some embodiments, such an oncolytic virus comprises nucleotide sequences encoding SEQ. ID. NO: 55 and ID. NO: 56. In some embodiments, such an oncolytic virus comprises nucleotide sequences encoding SEQ. ID. NO: 63 and ID. NO: 64. In some embodiments, such a oncolytic virus comprises nucleotide sequences encoding SEQ. ID. NO: 71 and ID. NO: 72. In some embodiments, such an oncolytic virus comprises nucleotide sequences encoding SEQ. ID, NO: 79 and ID. NO: 80. In some embodiments, such an oncolytic virus comprises nucleotide sequences encoding SEQ. ID. NO: 87 and ID. NO: 88. In some embodiments, such an oncolytic virus comprises nucleotide sequences encoding SEQ. ID. NO: 95 and ID. NO: 96. In some embodiments, such a oncolytic virus comprises nucleotide sequences encoding SEQ. ID. NO: 103 and ID. NO: 104.

In some embodiments, such an oncolytic virus comprises nucleotide sequences encoding amino acid sequences having at least 80% identity with a sequence set out in table 1 above. In some embodiments, such an oncolytic virus comprises nucleotide sequences encoding amino acid sequences having at least 85% identity with a sequence set out in table 1 above. In some embodiments, such an oncolytic virus comprises nucleotide sequences encoding amino acid sequences having at least 90% identity with a sequence set out in table 1 above. In some embodiments, such an oncolytic virus comprises nucleotide sequences encoding amino acid sequences having at least 95% identity with a sequence set out in table 1 above.

As an example, a nucleotide sequence encoding the antibody 001-F02 could be as presented in Table 4.

TABLE 4

Example of nucleotide sequences encoding the antibody 001-F02 - the parts of the sequences that are underlined in the table encodes the VH and VL sequences, respectively, of 001-F02

| Encoding | Sequence | SEQ. ID. NO: |
|---|---|---|
| 001-F02 VH | GAGGTGCAGCTGTTGGAGTCTGGGGGAGGCTTGG-TACAGCCTGGGGGGTCCCTGAGACTCTCCTGTGCAGCCTCTGGAT-TCACCTTCAGTGACTACTACATGAGCTGGGTCCGCCAGGCTCCCGG-GAAGGGGCTGGAGTGGGTGGCCAACATAAACACAGACGGTAG-TGAAAAATACTATCTGGACTCTGTGAAGGGCCGATTCAC-CATCTCCAGAGACAATTCCAAGAACACGCTGTATCTG-CAAATGAACAGCCTGAGAGCCGAGGACACTGCCGTG-TATTACTGTGCGAGAGAGGAGTACGGIGCTTTTGA-TATCTGGGGCCAAGGTACACTGGTCACCGTGAGCTCAGCCTCCAC-CAAGGGCCCATCGGTCTTCCCCCTGGCACCCTCCTCCAAGAGCAC-CTCTGGGGGCACAGCGGCCCTGGGCTGCCTGGTCAAGGAC-TACTTCCCCGAACCGGTGACGGTGTCGTG-GAACTCAGGCGCCCTGACCAGCGGCGTGCACAC-CTTCCCGGCTGTCCTACAGTCCTCAGGACTCTACTCCCTCAG-CAGCGTGGTGACCGTGCCCTCCAGCAGCTTGGGCACCCAGAC-CTACATCTGCAACGTGAATCACAAGCCCAGCAACACCAAGGTG-GACAAGAAAGTTGAGCCCAAATCTT-GTGACAAAACTCACACATGCCCACCGTGCCCAGCAC-CTGAACTCCTGGGGGGACCGTCAG-TCTTCCTCTTCCCCCCAAAACCCAAGGACACCCTCATGATCTCCCG-GACCCCTGAGGTCACATGCGTGGTGGTGGACGTGAGCCACGAA-GACCCTGAGGTCAAGTTCAACTGGTACGTGGACGGCGTGGAGGTG-CATAATGCCAAGACAAAGCCGCGGGAGGAGCAGTACAACAGCAC-GTACCGTGTGGTCAGCGTCCTCACCGTCCTGCACCAG-GACTGGCTGAATGGCAAGGAGTACAAGTGCAAGGTCTCCAACAAA-GCCCTCCCAGCCCCCATCGAGAAAACCATCTCCAAAGCCAAAGGG-CAGCCCCGAGAACCACAGGTGTACACCCTGCCCCCATCCCGG-GATGAGCTGACCAAGAACCAGGTCAGCCTGAC-CTGCCTGGTCAAAGGCTTCTATCCCAGCGACATCGCCGTGGAGTGG-GAGAGCAATGGGCAGCCGGAGAACAACTACAAGACCAC-GCCTCCCGTGCTGGACTCCGACGGCTCCTTCTTCCTCTACAGCAA-GCTCACCGTGGACAAGAGCAGGTGGCAGCAGGGGAAC-GTCTTCTCATGCTCCGTGATGCATGAGGCTCTGCACAACCACTACAC-GCAGAAGAGCCTCTCCCTGTCTCCGGGTAAATGA | 222 |
| 001-F02 VL | CAGTCTGTGCTGACTCAGCCACCCTCAGCGTCTGGGACCCCCGGG-CAGAGGGTCACCATCTCTTGTTCTGGAAGCAGCTCCAACATCG-GAAGTAATACTGTAAACTGGTATCAGCAGCTCCCAGGAAC-GGCCCCCAAACTCCTCATCTATGACAATAATAA-GCGACCCTCAGGGGTCCCTGACCGATTCTCTGGCTCCAAGTCTGG-CACCTCAGCCTCCCTGGCCATCAGTGGGCTCCGGTCCGAG-GATGAGGCTGATTATTACTGCCAGTCCTTTGACAGAGGGCTGAG-TGGCTCGATTGTATTCGGCGGAGGAACCAAGCTGAC-GGTCCTAGGTCAGCCCAAGGCTGCCCCCTCGGTCAC-TCTGTTCCCGCCCTCCTCTGAGGAGCTTCAAGCCAACAAGGCCACAC-TGGTGTGTCTCATAAGTGACTTCTACCCGGGAGCCGTGACAG-TGGCCTGGAAGGCAGATAGCAGCCCCGTCAAGGCGGGAGTGGA-GACCACCACACCCTCCAAACAAAGCAACAACAAGTACGCGGCCAG-CAGCTATCTGAGCCTGACGCCTGAGCAGTGGAAGTCCCACAGAAGC-TACAGCTGCCAGGTCACGCATGAAGGGAGCACCGTGGAGAAGACAG-TGGCCCCTACAGAATGTTCATGA | 223 |

Some oncolytic viruses have capacity to host large enough DNA insertions to accommodate integration of full-length human antibody sequences. Attenuated Vaccinia viruses and Herpes Simplex Viruses are examples of therapeutic oncolytic viruses whose genome is sufficiently large to permit integration of full-length IgG antibody sequences (Chan, W. M. et al 2014 Annu Rev Virol 1(1): 119-141; Bommareddy, P. K., et al. 2018 Nat Rev Immunol 18(8): 498-513). Full-length IgG antibodies have successfully been integrated into oncolytic Vaccinia virus, resulting in expression and extracellular release (production) of full-length IgG antibodies upon infection of virus-susceptible host cells e.g. cancer cells (Kleinpeter, P., et al. 2016, Oncoimmunology 5(10): e1220467). Adenoviruses can also be engineered to encode full-length IgG antibodies that are functionally produced and secreted upon cellular infection (Marino, N., et al. 2017 J Olin Invest 123(6): 2447-2463).

The invention also encompasses pharmaceutical compositions comprising a virus, such as an oncolytic virus, as discussed above, and a pharmaceutically acceptable diluent, vehicle and/or an adjuvant.

The pharmaceutical composition may in some embodiments be in the form of a CAR-T cell, carrying parts or the complete antibody sequences described herein as part of the sequence coding for its chimeric antigen T cell receptor.

The invention also encompasses pharmaceutical compositions comprising a CAR-T cell as discussed above and a pharmaceutically acceptable diluent, vehicle and/or an adjuvant.

The invention also comprises other therapeutic modalities, or "shapes" of drugs, such as antibody drug conjugates, fusion proteins etc., and pharmaceutical composition comprising such therapeutic modalities.

The antibody molecules, nucleotide sequences, plasmids, viruses, cells and/or pharmaceutical compositions described herein may be suitable for parenteral administration including aqueous and/or non-aqueous sterile injection solutions which may contain anti-oxidants, and/or buffers, and/or bacteriostats, and/or solutes which render the formulation isotonic with the blood of the intended recipient; and/or aqueous and/or non-aqueous sterile suspensions which may include suspending agents and/or thickening agents. The antibody molecules, nucleotide sequences, plasmids, cells and/or pharmaceutical compositions described herein may be presented in unit-dose or multi-dose containers, for example sealed ampoules and vials, and may be stored in a freeze-dried (i.e, lyophilized) condition requiring only the addition of the sterile liquid carrier, for example water for injections, immediately prior to use.

Extemporaneous injection solutions and suspensions may be prepared from sterile powders, and/or granules, and/or tablets of the kind previously described.

For parenteral administration to human patients, the daily dosage level of the anti-TNFR2 antibody molecule will usually be from 1 mg/kg bodyweight of the patient to 20 mg/kg, or in some cases even up to 100 mg/kg administered in single or divided doses. Lower doses may be used in special circumstances, for example in combination with prolonged administration. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited, and such are within the scope of this invention.

Typically, a pharmaceutical composition (or medicament) described herein comprising an antibody molecule will contain the anti-TNFR2 antibody molecule at a concentration of between approximately 2 mg/ml and 150 mg/ml or between approximately 2 mg/ml and 200 mg/ml.

Generally, in humans, oral or parenteral administration of the antibody molecules, nucleotide sequences, plasmids, viruses, cells and/or pharmaceutical compositions described herein is the preferred route, being the most convenient. For veterinary use, the antibody molecules, nucleotide sequences, plasmids, viruses, cells and/or pharmaceutical compositions described herein are administered as a suitably acceptable formulation in accordance with normal veterinary practice and the veterinary surgeon will determine the dosing regimen and route of administration which will be most appropriate for a particular animal. Thus, the present invention provides a pharmaceutical formulation comprising an amount of an antibody molecule, nucleotide sequence, plasmid, virus and/or cell of the invention effective to treat various conditions (as described above and further below). Preferably, the antibody molecules, nucleotide sequences, plasmids, viruses, cells and/or pharmaceutical compositions described herein is adapted for delivery by a route selected from the group comprising: intravenous (IV or i.v.); intramuscular (IM or i.m.); subcutaneous (SC or s.c.) or intratumoral.

The present invention also includes antibody molecules, nucleotide sequences, plasmids, viruses, cells and/or pharmaceutical compositions described herein comprising pharmaceutically acceptable acid or base addition salts of the target binding molecules or parts of the present invention. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others. Pharmaceutically acceptable base addition salts may also be used to produce pharmaceutically acceptable salt forms of the agents according to the present invention. The chemical bases that may be used as reagents to prepare pharmaceutically acceptable base salts of the present agents that are acidic in nature are those that form non-toxic base salts with such compounds. Such non-toxic base salts include, but are not limited to, those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others. The antibody molecules, nucleotide sequences, plasmids, viruses and/or cells described herein may be lyophilized for storage and reconstituted in a suitable carrier prior to use. Any suitable lyophilization method (e.g. spray drying, cake drying) and/or reconstitution techniques can be employed. It will be appreciated by those skilled in the art that lyophilization and reconstitution can lead to varying degrees of antibody activity loss (e.g. with conventional immunoglobulins, IgM antibodies tend to have greater activity loss than IgG antibodies) and that use levels may have to be adjusted upward to compensate. In one embodiment, the lyophilized (freeze dried) polypeptide binding moiety loses no more than about 20%, or no more than about 25%, or no more than about 30%, or no more than about 35%, or no more than about 40%, or no more than about 45%, or no more than about 50% of its activity (prior to lyophilization) when re-hydrated.

The anti-TNFR2 antibody molecules, nucleotide sequences and pharmaceutical compositions described herein can be used use in the treatment of cancer in a subject or patient. Herein, the terms subject and patient are used interchangeably "Patient" (or subject) as the term is used herein refers to an animal, including hula that has been diagnosed as having cancer and/or that exhibits symptoms of a specific disease.

In some embodiments, the patient (or subject) is an animal, including human, that has been diagnosed as having cancer.

In some embodiments, the patient (or subject) is an animal, including human, that has been diagnosed as having a chronic inflammatory disease and/or that exhibits symptoms of a chronic inflammatory disease, Chronic inflammatory diseases as used herein include autoimmune diseases. As described above, several different immune cells can express TNFR2 and depending on the disease and context, the relative levels of expression can vary. It is well known that e.g. regulatory T cells can express high levels of TNFR2, and that these can be expanded by TNFR2 agonists. Regulatory T cells constitute a subpopulation of T cells capable of suppressing other immune cells in normal and pathological immune settings and are considered instrumental in preventing autoimmune attacks on self tissues. Hence, stimulating regulatory T cell activity could be very important in treating autoimmune disorders (Sharabi et al. "Regulatory T cells in the treatment of disease". Nat Rev Drug Discov. 2018 Oct. 12). Examples of chronic inflammatory diseases besides autoimmune disorders are osteoarthritis and celiac disease. Examples of autoimmune disorders are rheumatoid arthritis (RA), multiple sclerosis (MS), diabetes mellitus type I, systemic lupus erythematosus (SLE), psoriasis, inflammatory bowel disease (IBD) or Myasthenia gravis (MG).

In some embodiments, the patient (or subject) is a patient having high TNFR2 expression in diseased tissue. In this context, high expression means a higher level of TNFR2 expression compared to corresponding healthy tissue. Normally the healthy tissue used for such a comparison is a reference tissue (or standard reference) collected from healthy tissue from one or several healthy individuals. The level of expression can be measured by standard techniques such as immunohistochemistry (IHC), fluorescence-activated cell sorting (FACS) or mRNA expression measurements.

We include that the patient could be mammalian or non-mammalian. Preferably, the mammalian patient is a human, a horse, a cow, a sheep, a pig, a camel, a dog or a cat. Most preferably, the mammalian patient is a human.

By exhibit symptoms of cancer, we include that the patient displays a cancer symptom and/or a cancer diagnostic marker, and/or the cancer symptom and/or a cancer diagnostic marker can be measured, and/or assessed, and/or quantified.

It would be readily apparent to the person skilled in medicine what the cancer symptoms and cancer diagnostic markers would be and how to measure and/or assess and/or quantify whether there is a reduction or increase in the severity of the cancer symptoms, or a reduction or increase in the cancer diagnostic markers; as well as how those cancer symptoms and/or cancer diagnostic markers could be used to form a prognosis for the cancer.

Cancer treatments are often administered as a course of treatment, which is to say that the therapeutic agent is administered over a period of time. The length of time of the course of treatment will depend on a number of factors, which could include the type of therapeutic agent being administered, the type of cancer being treated, the severity of the cancer being treated, and the age and health of the patient, amongst other reasons.

By "during the treatment", we include that the patient is currently receiving a course of treatment, and/or receiving a therapeutic agent, and/or receiving a course of a therapeutic agent.

In some embodiments the cancer to be treated in accordance with the present invention is a solid tumor.

Each one of the above described cancers is well-known, and the symptoms and cancer diagnostic markers are well described, as are the therapeutic agents used to treat those cancers. Accordingly, the symptoms, cancer diagnostic markers, and therapeutic agents used to treat the above mentioned cancer types would be known to those skilled in medicine.

Clinical definitions of the diagnosis, prognosis and progression of a large number of cancers rely on certain classifications known as staging. Those staging systems act to collate a number of different cancer diagnostic markers and cancer symptoms to provide a summary of the diagnosis, and/or prognosis, and/or progression of the cancer. It would be known to the person skilled in oncology how to assess the diagnosis, and/or prognosis, and/or progression of the cancer using a staging system, and which cancer diagnostic markers and cancer symptoms should be used to do so.

By "cancer staging", we include the Rai staging, which includes stage 0, stage I, stage II, stage III and stage IV, and/or the Binet staging, which includes stage A, stage B and stage C, and/or the Ann Arbour staging, which includes stage I, stage II, stage III and stage IV.

It is known that cancer can cause abnormalities in the morphology of cells. These abnormalities often reproducibly occur in certain cancers, which means that examining these changes in morphology (otherwise known as histological examination) can be used in the diagnosis or prognosis of cancer. Techniques for visualizing samples to examine the morphology of cells, and preparing samples for visualization, are well known in the art; for example, light microscopy or confocal microscopy.

By "histological examination", we include the presence of small, mature lymphocyte, and/or the presence of small, mature lymphocytes with a narrow border of cytoplasm, the presence of small, mature lymphocytes with a dense nucleus lacking discernible nucleoli, and/or the presence of small, mature lymphocytes with a narrow border of cytoplasm, and with a dense nucleus lacking discernible nucleoli, and/or the presence of atypical cells, and/or cleaved cells, and/or prolymphocytes.

It is well known that cancer is a result of mutations in the DNA of the cell, which can lead to the cell avoiding cell death or uncontrollably proliferating, Therefore, examining these mutations (also known as cytogenetic examination) can be a useful tool for assessing the diagnosis and/or prognosis of a cancer. An example of this is the deletion of the chromosomal location 13q14.1 which is characteristic of chronic lymphocytic leukemia, Techniques for examining mutations in cells are well known in the art; for example, fluorescence in situ hybridization (FISH).

By "cytogenetic examination", we include the examination of the DNA in a cell, and, in particular the chromosomes. Cytogenetic examination can be used to identify changes in DNA which may be associated with the presence of a refractory cancer and/or relapsed cancer. Such may include: deletions in the long arm of chromosome 13, and/or the deletion of chromosomal location 13q14.1, and/or trisomy of chromosome 12, and/or deletions in the long arm of chromosome 12, and/or deletions in the long arm of chromosome 11, and/or the deletion of 11q, and/or deletions in the long arm of chromosome 6, and/or the deletion of 6q, and/or deletions in the short arm of chromosome 17, and/or the deletion of 17p, and/or the t(11:14) translocation, and/or the (q13:q32) translocation, and/or antigen gene receptor rearrangements, and/or BCL2 rearrangements, and/or BCL6 rearrangements, and/or t(14:18) translocations, and/or t(11:14) translocations, and/or (q13:q32) translocations, and/or (3:v) translocations, and/or (8:14) translocations, and/or (8:v) translocations, and/or t(11:14) and (q13:q32) translocations.

It is known that patients with cancer exhibit certain physical symptoms, which are often as a result of the burden of the cancer on the body. Those symptoms often reoccur in the same cancer, and so can be characteristic of the diagnosis, and/or prognosis, and/or progression of the disease. A person skilled in medicine would understand which physical symptoms are associated with which cancers, and how assessing those physical systems can correlate to the diagnosis, and/or prognosis, and/or progression of the disease. By "physical symptoms", we include hepatomegaly, and/or splenomegaly.

BRIEF DESCRIPTION OF THE DRAWINGS

In the examples below, reference is made to the following figures:

FIG. 1 A-D: Human antibodies were shown by ELISA to bind to human TNFR2 protein in a dose-dependent manner generating different EC50 values, FIG. 1 E: The murine antibodies 3-F10 and 5-A05 bind to mTNFR2 with a similar affinity.

While human TNFR2 antibodies bind with different affinities to in vitro activated CD4+ T cells (ranging EC50 values from 0.59 to 53 nM) the mouse TNFR2 antibodies bind with similar affinity (EC50 values ranging from 0.072 to 0.11 nM).

Figure 1A:
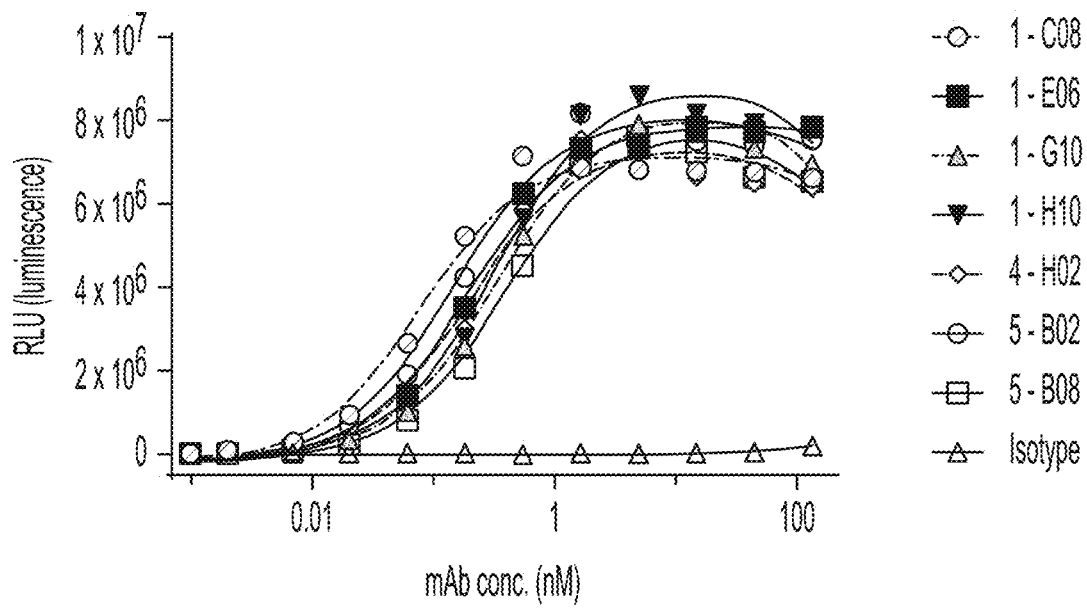
FIG. 1 demonstrates that antibodies of the invention bind TNFR2.
Figure 1B:
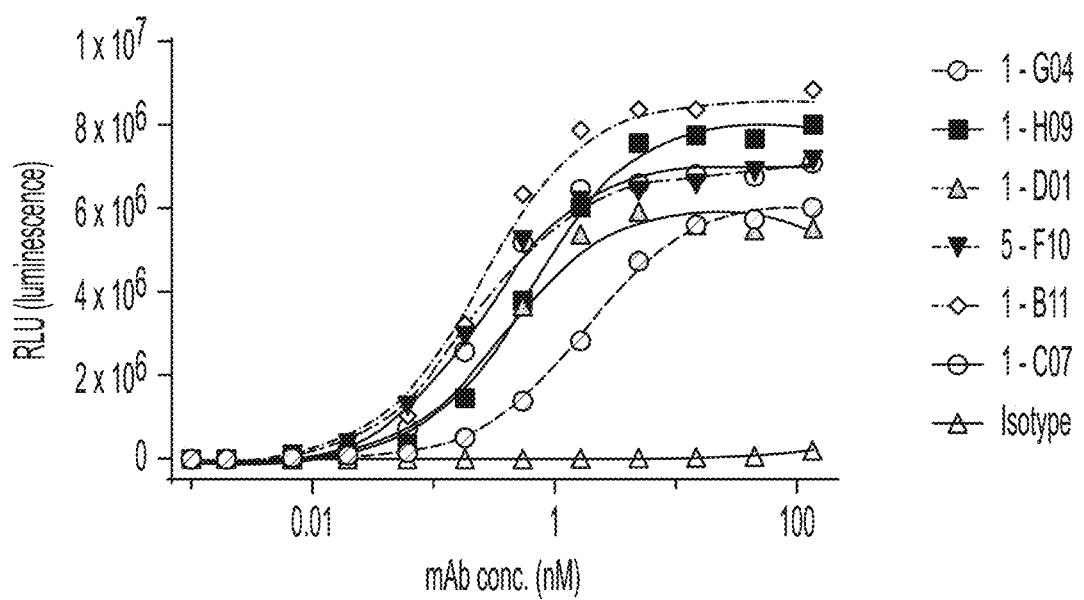
Figure 1C:
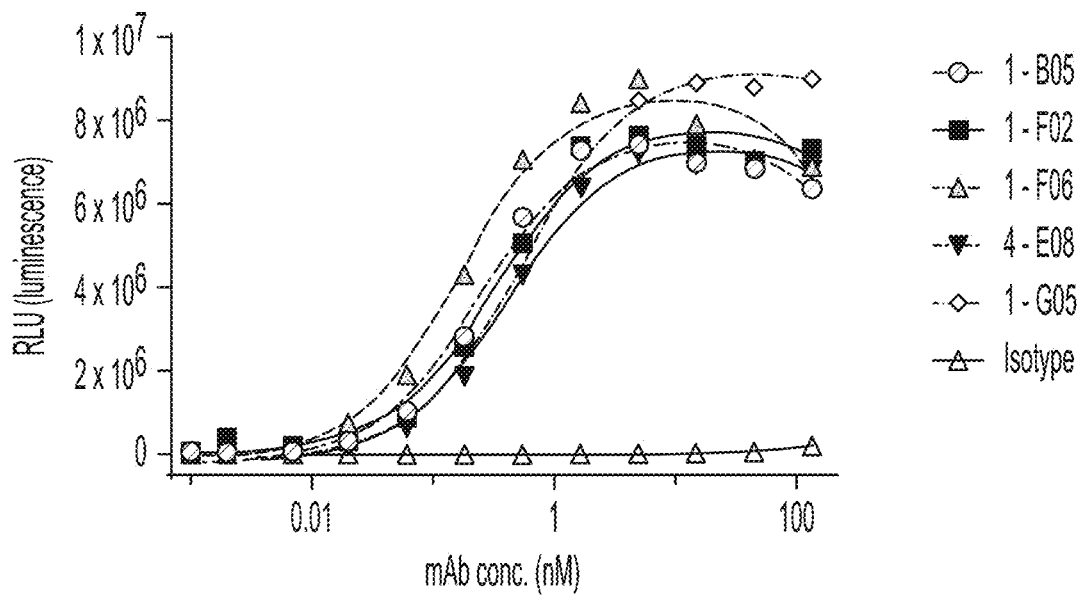
Figure 1D:
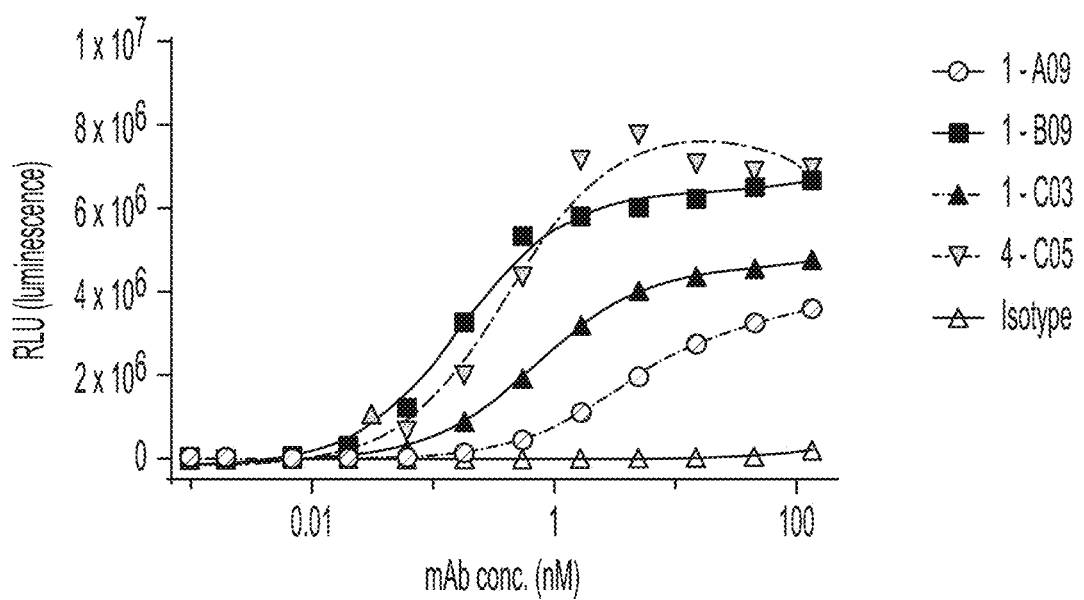
Figure 1E:
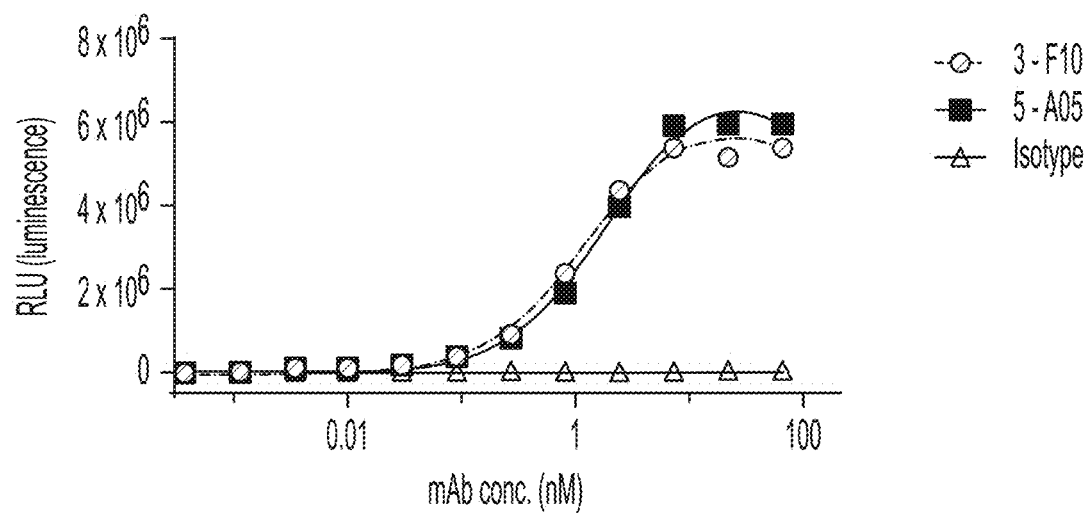
Figure 2A:
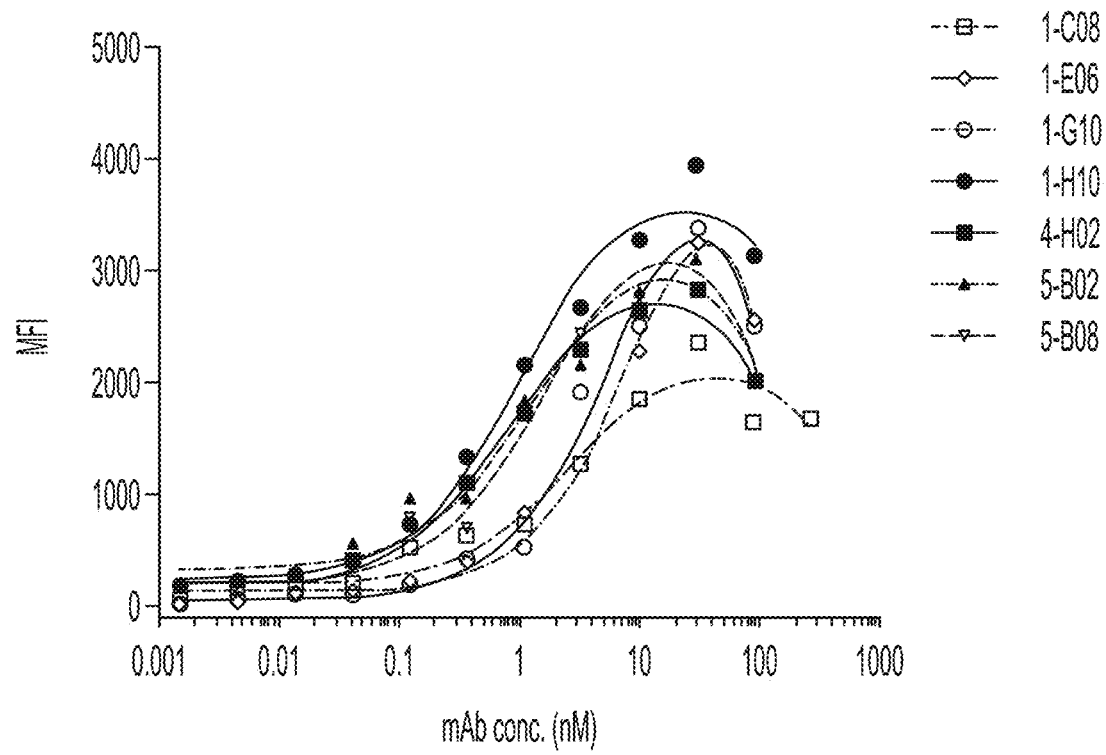
FIG. 2 shows binding of TNFR2 specific n-CoDeR® antibodies to in vitro activated CD4+ T cells. Human blood derived CD4+ T cells (FIGS. 2 A-D) and mouse splenic CD4+ T cells (FIG. 2 E) were activated with IL-2 and CD3/CD28 Dynabeads®. The affinity of TNFR2 specific n-CoDeR® antibodies to activated cells were analyzed by FACS at concentrations ranging from 0.002-267 nM (human) and 0.00003-133 nM (mouse). The curves show MFI after subtraction of isotype control background (FIG. 2 A (complete and partial blockers), FIG. 2 B (partial-blockers), FIGS. 2 C and D (non-blockers), FIG. 2 E (mouse surrogate complete blocker (3-F10) and non-blocker (5-A05)).
Figure 2B:
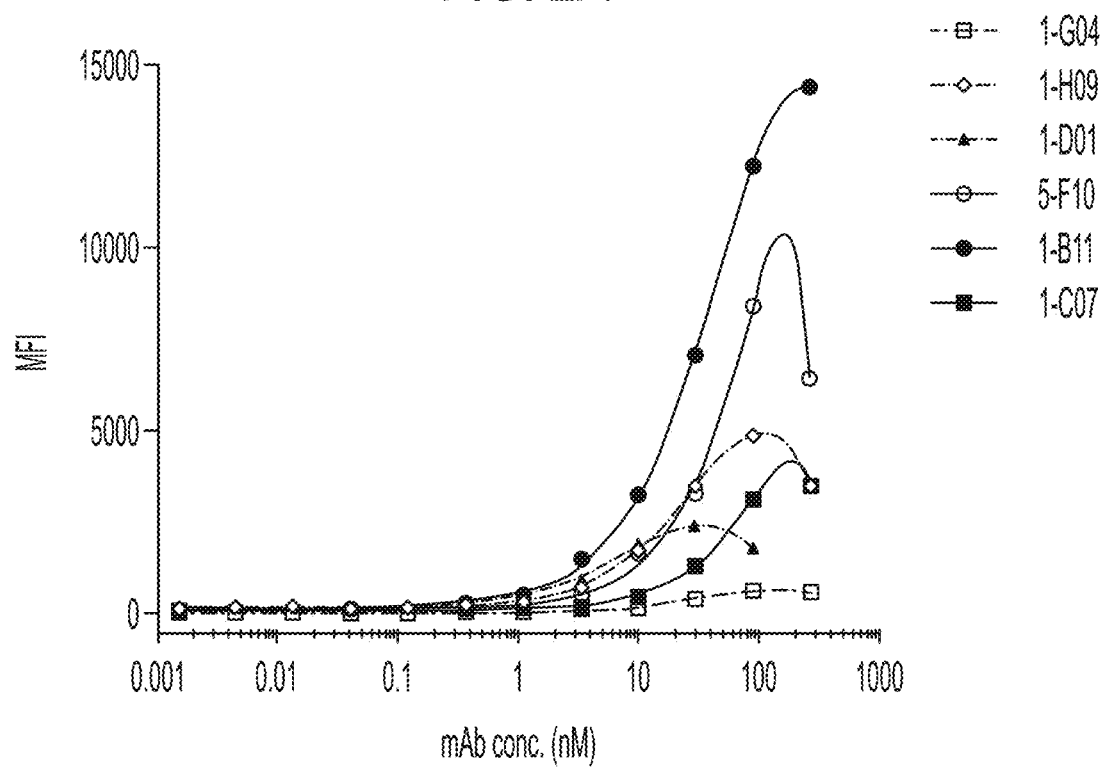
Figure 2C:
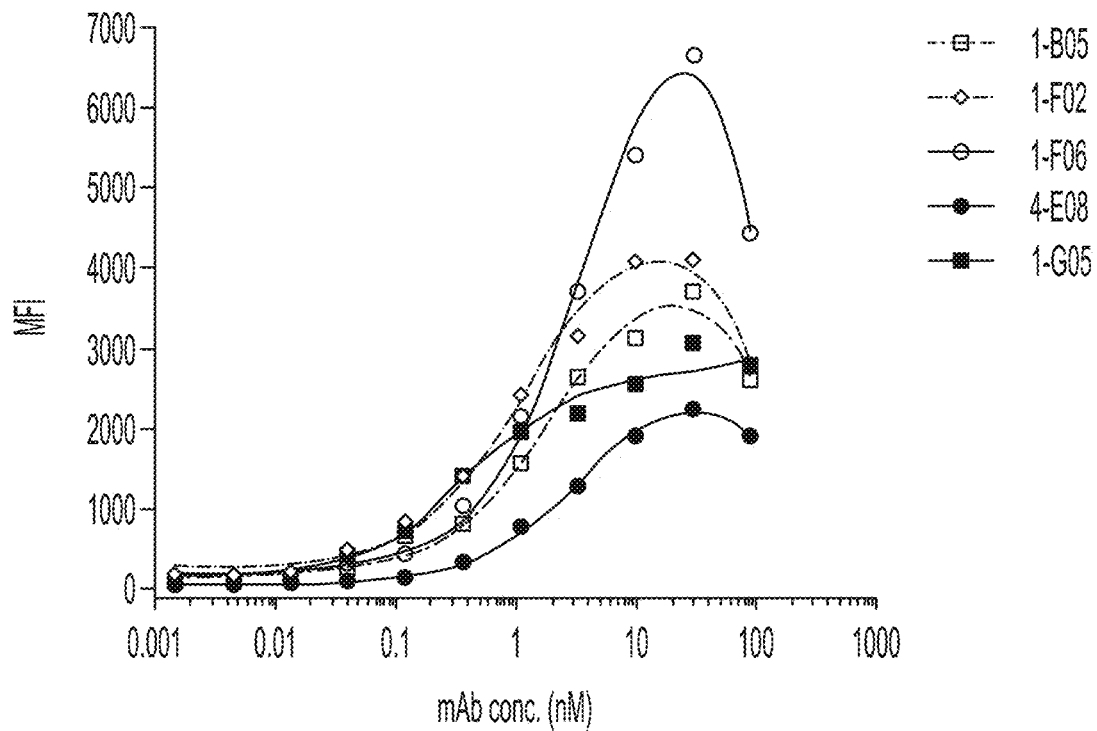
Figure 2D:
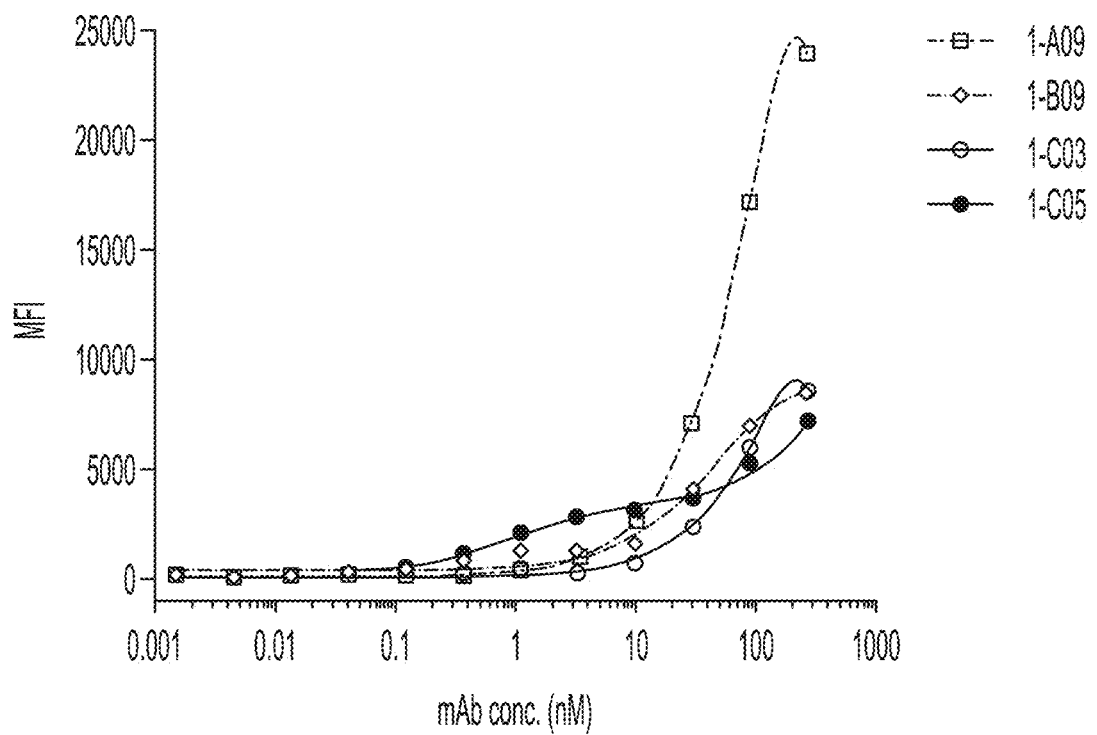
Figure 2E:
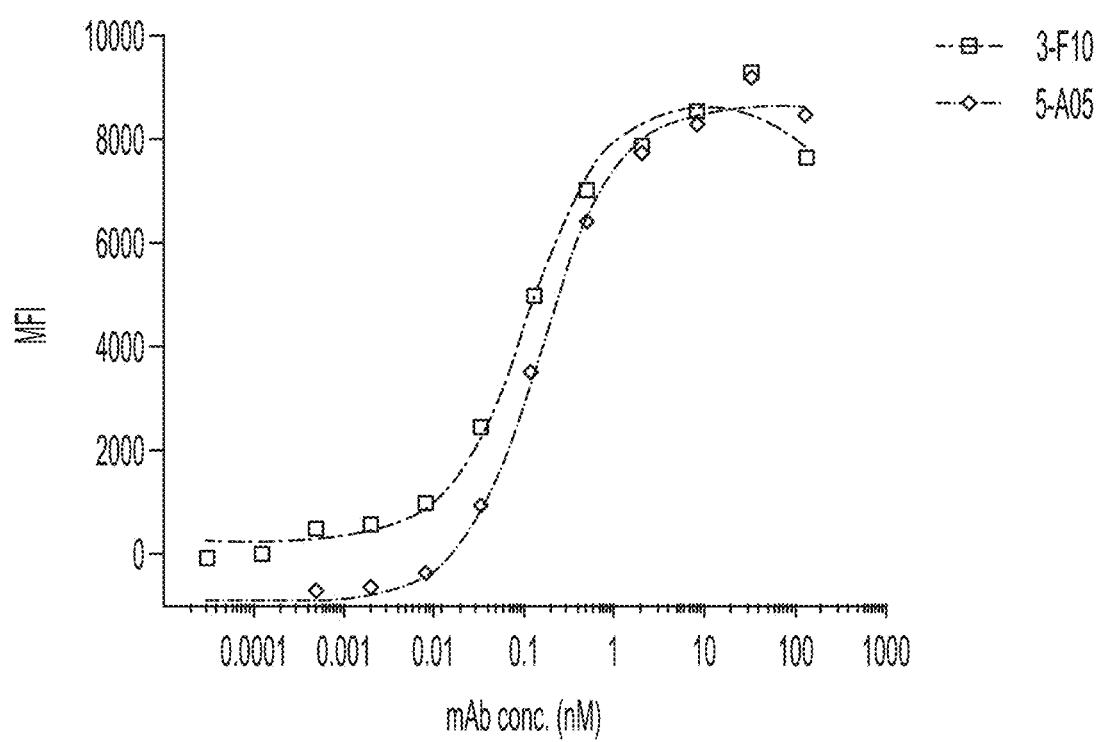
Figure 3:
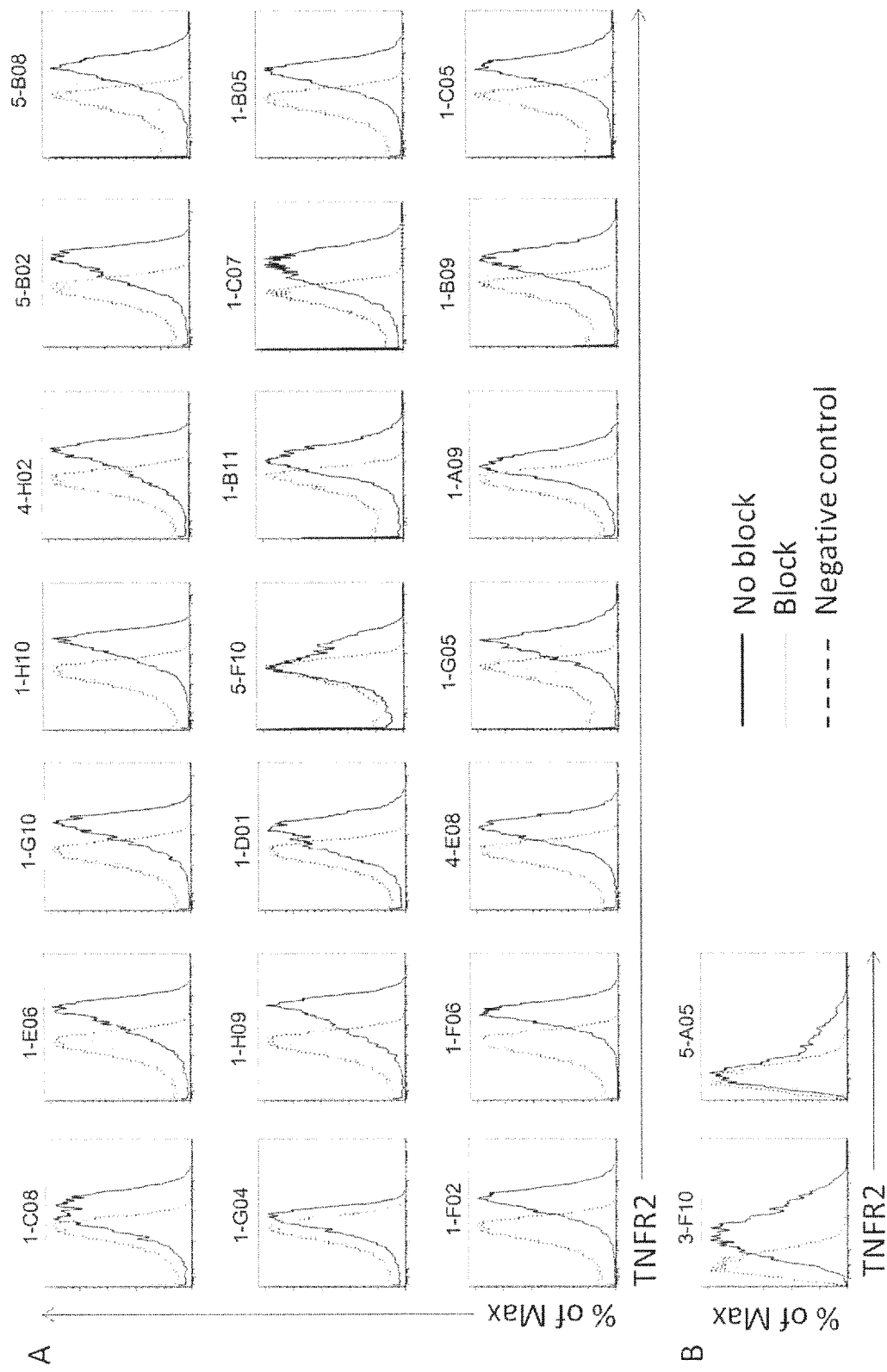

FIG. 3 shows that TNFR2 n-CoDeR® antibodies specifically bind to TNFR2. Human blood derived CD4+ T cells (FIG. 3 A) and mouse splenic CD4+ T cells (FIG. 3 B) were activated 3 days with recombinant IL-2 and CD3/CD28 activation beads. In vitro activated cells were blocked with a polyclonal TNFR2 antibody (grey line) or left in PBS (black line) for 30 min before stained with suboptimal concentration of the different TNFR2 n-CoDeR® antibodies or isotype control (dashed line) for 15 min. Cells were then washed and incubated with an APC conjugated secondary antibody for 30 min before analyzed by flow cytometry.

Binding of all antibodies could be blocked by the polyclonal TNFR2 antibody, hence show that the TNFR2 n-CoDeR® antibodies (human and mouse) are specific to TNFR2.

Figure 4:
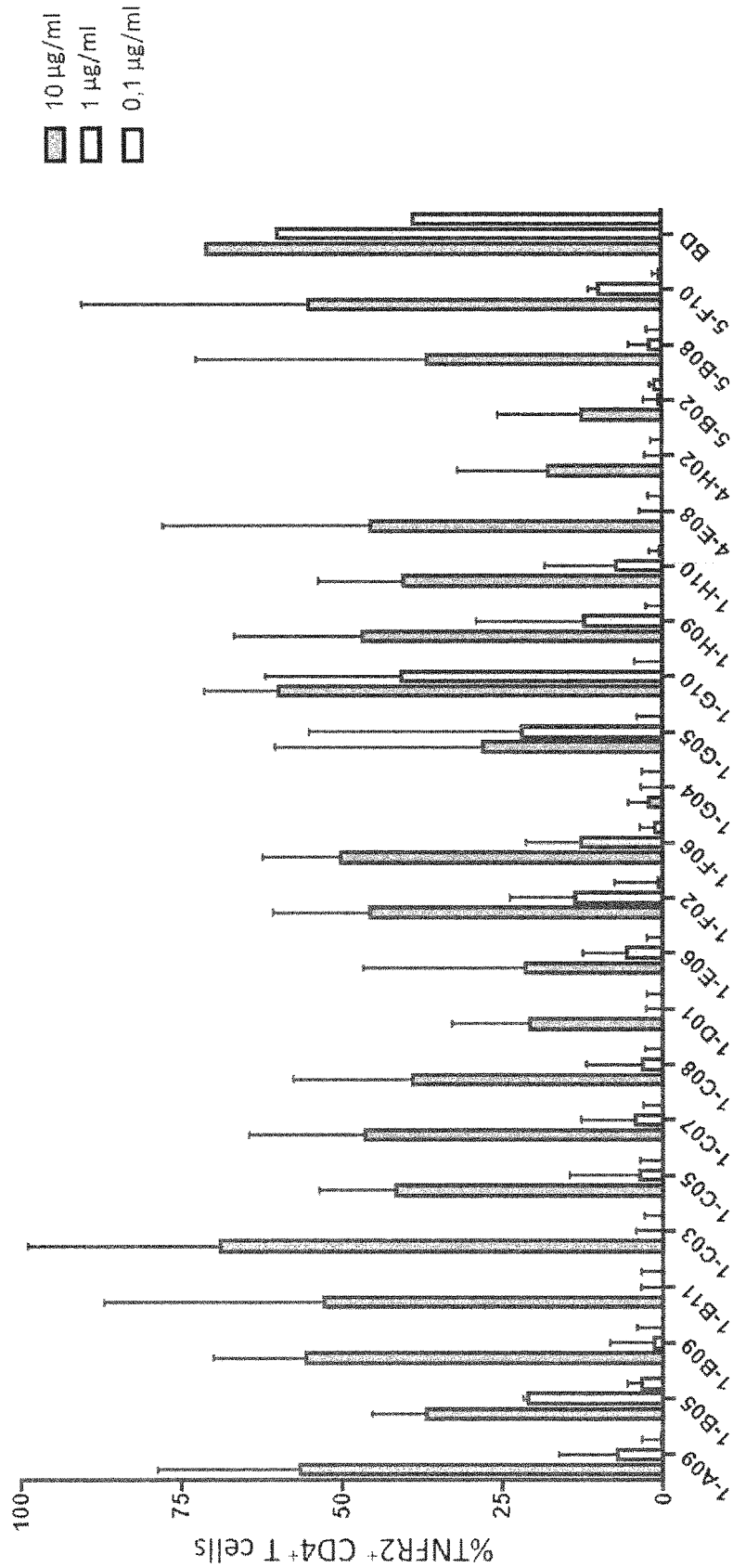

FIG. 4 shows cross-reactivity of human TNFR2 specific n-CoDeR® antibodies to Cynomolgus CD4+ T cells were isolated from cynomolgus blood and stimulated with PMA and Ionomycin. After 2 days the cells were labelled with 0.1, 1 or 10 µg/ml TNFR2 specific n-CoDeR® antibodies or isotype control followed by incubation with an APC conjugated secondary a-human antibody. Cells were analyzed by flow cytometry. The figure shows percentages of TNFR2+ T cells for the individual antibodies over the isotype control. The results are the mean value and SD from 2-3 individual experiments.

Most TNFR2 antibodies show cross-reactive binding to Cynomolgus cells.

Figure 5:
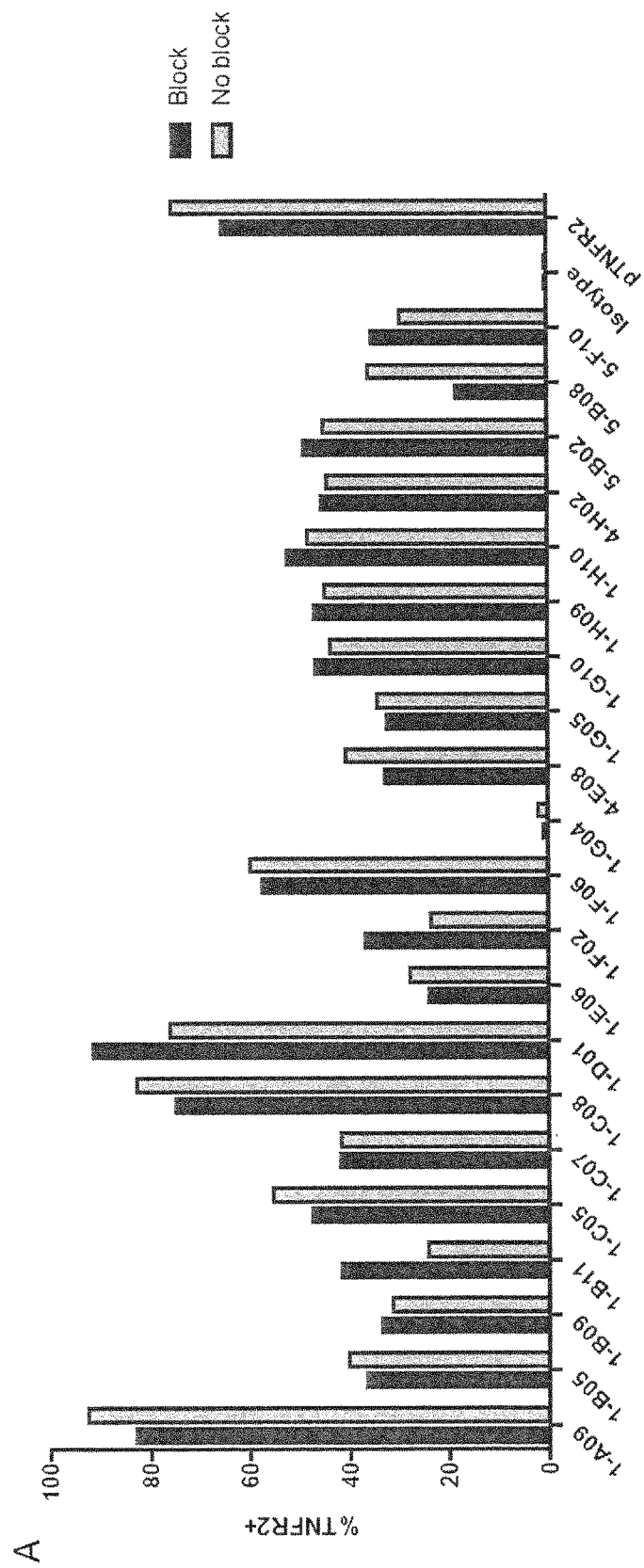
Figure 5:

FIG. 5 Activated cells were either blocked by 40 µg/ml MR2-1 antibody (FIG. 5 A, black bars) or left with PBS (FIG. 5 A, grey bars) 30 min, then TNFR2 specific n-CoDeR® antibodies/polyclonal TNFR2 (pTNFR2) were added and cells were incubated 15 min. Percent bound TNFR2 n-CoDeR® antibodies were analyzed by FACS after incubation with APC conjugated secondary antibodies. In FIG. 5 B, activated CD4+ T cells were blocked with 40 µg/ml TNFR2 specific n-CoDeR® antibodies/pTNFR2 (black bars) or left with PBS (grey bar) and then incubated 15 min with PE conjugated MR2-1 antibody. Cells were then analyzed by FACS.

MR2-1 antibody did not interfere with the binding of the TNFR2 specific n-CoDeR® antibodies and the n-CoDeR® antibodies did not affect the binding of MR2-1 to activated cells showing that the n-CoDeR® antibodies all bind other domains of the TNFR2 protein than the MR2-1 antibody. This shows that the TNFr2 specific n-CoDeR® antibodies all bind other epitopes on the TNFR2 protein than the TNFR2 clone MR2-1.

Human blood derived CD4+ T cells were stimulated with rhIL-2 and CD3/CD28 activation beads 2-3 days. Activated cells were either blocked by 40 µg/ml MR2-1 antibody (FIG. 5 A, black bars) or left with PBS (FIG. 5 A, grey bars) 30 min, then TNFR2 specific n-CoDeR® antibodies/polyclonal TNFR2 (pTNFR2) were added and cells were incubated 15 min. Percent bound TNFR2 n-CoDeR® antibodies were analyzed by FACS after incubation with APC conjugated secondary antibodies. In FIG. 5 B, activated CD4+ T cells were blocked with 40 µg/ml TNFR2 specific n-CoDeR® antibodies/pTNFR2 (black bars) or left with PBS (grey bar) and then incubated 15 min with PE conjugated MR2-1 antibody. Cells were then analyzed by FACS.

MR2-1 antibody did not interfere with the binding of the TNFR2 specific n-CoDeR® antibodies and the n-CoDeR® antibodies did not affect the binding of MR2-1 to activated cells showing that the n-CoDeR® antibodies all bind other domains of the TNFR2 protein than the MR2-1 antibody.

Figure 6:
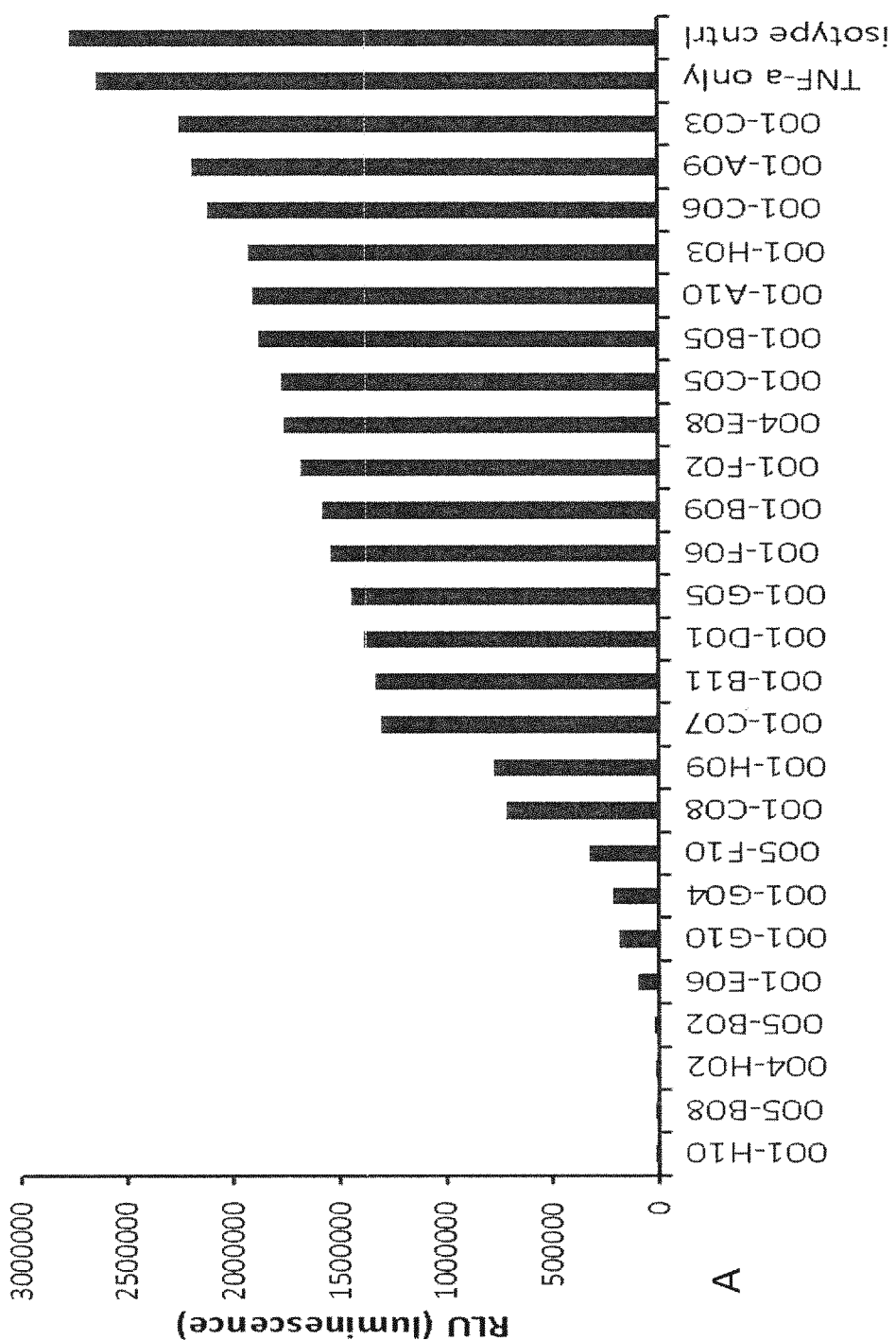

FIG. 6 shows data for ligand blocking antibodies. Blocking ELISAs were performed with n-CoDeR® mAbs specific for hTNFRII to evaluate ligand blocking characteristics. FIG. 6 A) All antibodies were incubated at 10 µg/ml. Subsequently, all antibodies reducing the signal achieved with the isotype control by more than 50% (indicated by the dotted line) were dosed to further explore the ligand blocking potential. FIG. 6 B) shows complete blocking mAbs, FIGS. 6 C) and D) show partially blocking mAbs and FIG. 6 E) shows weak blocking mAbs. All other mAbs are considered non-blocking mAbs FIG. 7 shows data for ligand blocking antibodies. Blocking ELISAs were performed with n-CoDeR® mAbs specific for mTNFRII to evaluate ligand blocking characteristics. FIG. 7 A) All antibodies were incubated at 10 µg/ml. Subsequently, all antibodies reducing the signal achieved with the isotype control by more than 50% (indicated by the dotted line) were dosed to further explore the ligand blocking potential. FIG. 7 B) shows complete blocking mAbs, FIGS. 7 C) and D) show partially blocking mAbs and FIG. 7E) shows weak blocking mAbs. All other mAbs are considered non-blocking mAbs.

Figure 8:
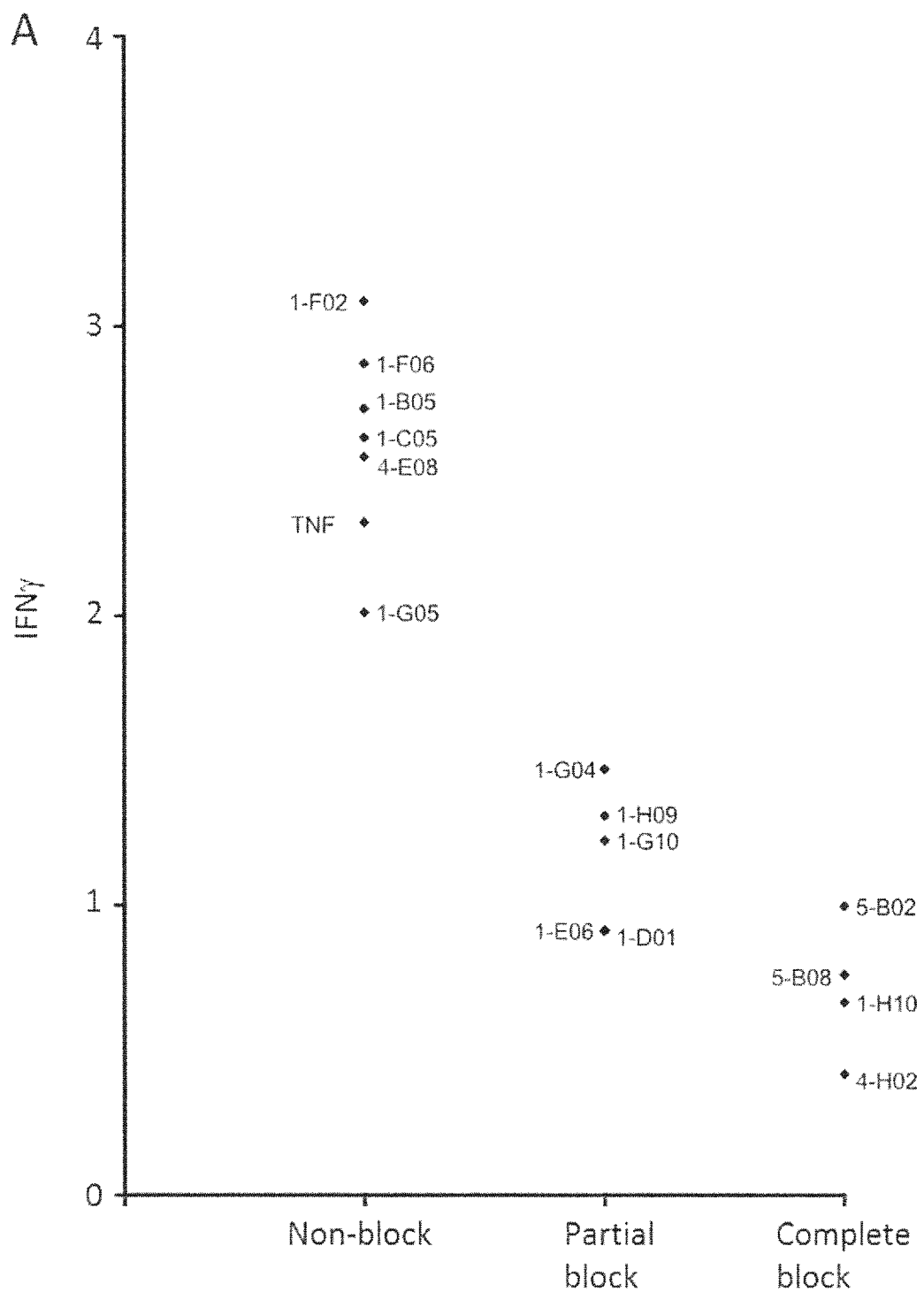

FIG. 8 show that agonistic non-blocking but not antagonistic blocking TNFR2 specific n-CoDeR® antibodies enhance the IFN-γ production in IL-2 and IL-12 stimulated NK cells. FIG. 8 A: Human blood derived NK cells were stimulated with 20 ng/ml rhIL-2 and 20 ng/ml rhIL-12 with the addition of 10 µg/ml TNFR2 specific n-CoDeR® antibodies, isotype control or 100 ng/ml rhTNF-α for 24 h. The amount of IFN-γ in the culture supernatants was measured using MSD. The quantity of IFN-γ are normalized to isotype control and shown in FIG. 8 A. Human antibodies that had a higher EC50 value than 25 nM to in vitro activated CD4+ T cells were not included in the analysis. Human NK cells also produce TNF-α in these cultures (see FIG. 80 below).

IFN-γ results are the mean value of 3 donors in 2 independent experiments. The results show that non-blocking TNFR2 antibodies are agonistic and enhance the IFN-γ production from cytokine stimulated NK cells while blocking antibodies are rather antagonistic and decrease the IFN-γ production by the NK cells. In addition, FIG. 8 B-D, show that the agonistic antibodies have an intrinsic agonistic activity, even in the absence of measurable TNF-α ligand. As shown in FIG. 8B, the Addition of blocking TNF-α antibody lowers the amount of IFN-γ release but the ratio over an isotype control (FIG. 8C) is still maintained even in complete absence of measurable TNF-α in the supernatant (FIG. 8D). FIG. 8D shows mean TNF-α levels in 2 donors in presence or absence of TNF-α neutralizing antibodies FIG. 9 show that agonistic non-blocking but not antagonistic blocking TNFR2 specific n-CoDeR® antibodies activate the memory CD4+ T cells population shown by increase in the proportion of CD25+ cells. Human blood derived CD4+ T cells (FIG. 9 A) and mouse splenic CD4+ T cells (FIG. 9 B) were activated with recombinant IL-2 and TNFR2 specific n-CoDeR® antibodies, isotype control or recombinant TNF-α. After 3 days of culture the cells were stained for CD25 and CD45RO (human)/CD44 and CD62L (mouse) and analyzed by flow cytometry. The results show the percentage of CD25 expressing cells on the memory (CD45RO+ cells (human)/CD44+CD62L− (mouse)) population over the percentage of CD25+ cells recovered in cultures with isotype control. The results are the mean value and SEM of 7 donors (FIG. 9 A, human) and 3 mice (in 2 independent experiments) (FIG. 9 B). In both human and mouse cultures non-blocking TNFR2 antibodies induced the percentage of CD25+ memory cells, while blocking antibodies had no such effect on the memory population. For both human cultures (FIG. 9 A) and murine (FIG. 9 B), the addition of exogenous TNF-α increase the CD25+ memory T cell population. *=p<0.05 as calculated by one-way ANOVA.

Figure 10:
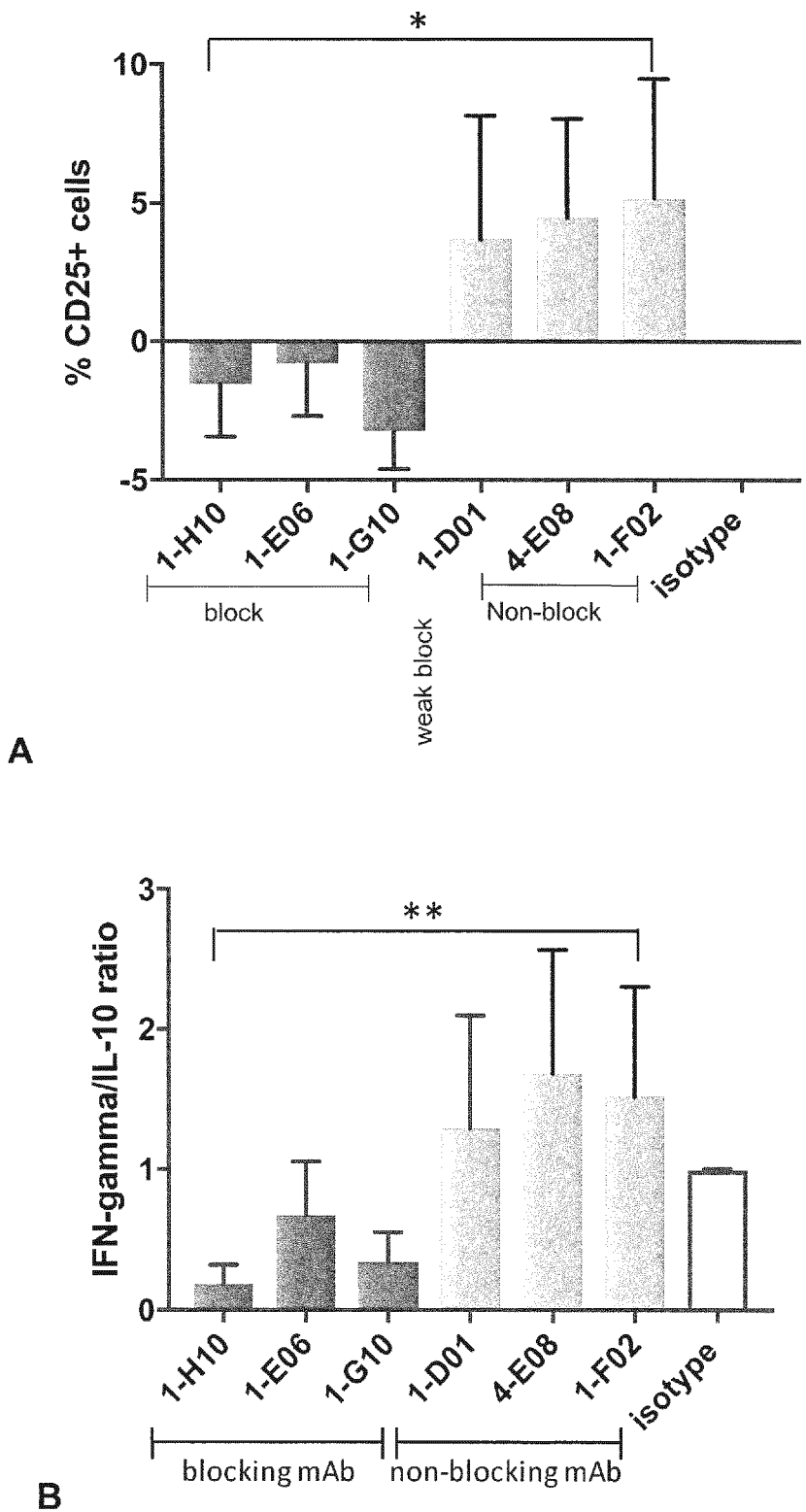

FIG. 10 show that anti-TNFR2 mAb modulate Myeloid-Derived Suppressive Cells' (MDSCs) suppressive function. For FIGS. 10 A and B MDSCs were pre-incubated with human anti-TNFR2 mAb for 30 min. Without washing the cells, titrating numbers of MDSCs were then incubated with CFSE-labelled CD3+ T cells in the presence of CD3/CD28 Dynabeads®. FIG. 10A: % activated CD25+ T cells were determined after 3 days by FACS. To normalize between different assays, isotype control background was subtracted from all data points. Figure shows a summary of 6 different donors in 3 independent experiments at a ratio of MDSCs to T cells of 1:4. FIG. 10 B: the amount of secreted cytokines in the supernatant was assessed by MSD and the ratio between IFN-γ and IL-10 release was calculated in relation to isotype control. Data were pooled from the analysis of culture supernatants obtained from experiments with 5 different donors.

For FIG. 10 C CD11b+ myeloid cells from a mouse CT26 tumor were isolated and pre-incubated with mouse anti-TNFR2 mAb for 30 min. Titrating numbers of myeloid cells were co-cultured with CFSE-labelled CD3+T cells which were purified from naïve Balb/C spleens. Cells were stimulated with CD3/CD28 Dynabeads® for 3 days and % proliferating CFSE$^{low}$ cells was then analyzed by FACS. (n=4 independent experiments). Only agonistic/non-blocking anti-TNFR2 mAb were shown to reverse MDSCs' suppressive function in T cell/MDSC co-culture assays.

For FIG. 10 D MDSCs were pre-incubated for 30 min with two different human anti-TNFR2 mAb (one blocking=1H10) and one non-blocking (=1F02) in 3 different isotypes, including the Fc defective format were amino acid position 297 has been switched resulting in loss of glycosylation and thereby diminished binding to FcγRs (here denominated N297Q). Without washing the cells, titrating numbers of MDSCs were then incubated with CFSE-labelled CD3+ T cells in the presence of CD3/CD28 Dynabeads® and % activated CD25+ T cells was determined after 3 days by FACS. To normalize between different assays, isotype control background was subtracted from all data points. The figure shows that the agonistic activity of the non-blocking 1-F02 antibody is independent of antibody isotype and FcγR binding. The figure shows a summary of 4 different donors in 2 independent experiments at a ratio of MDSCs to T cells of 1:4.

Figure 11:
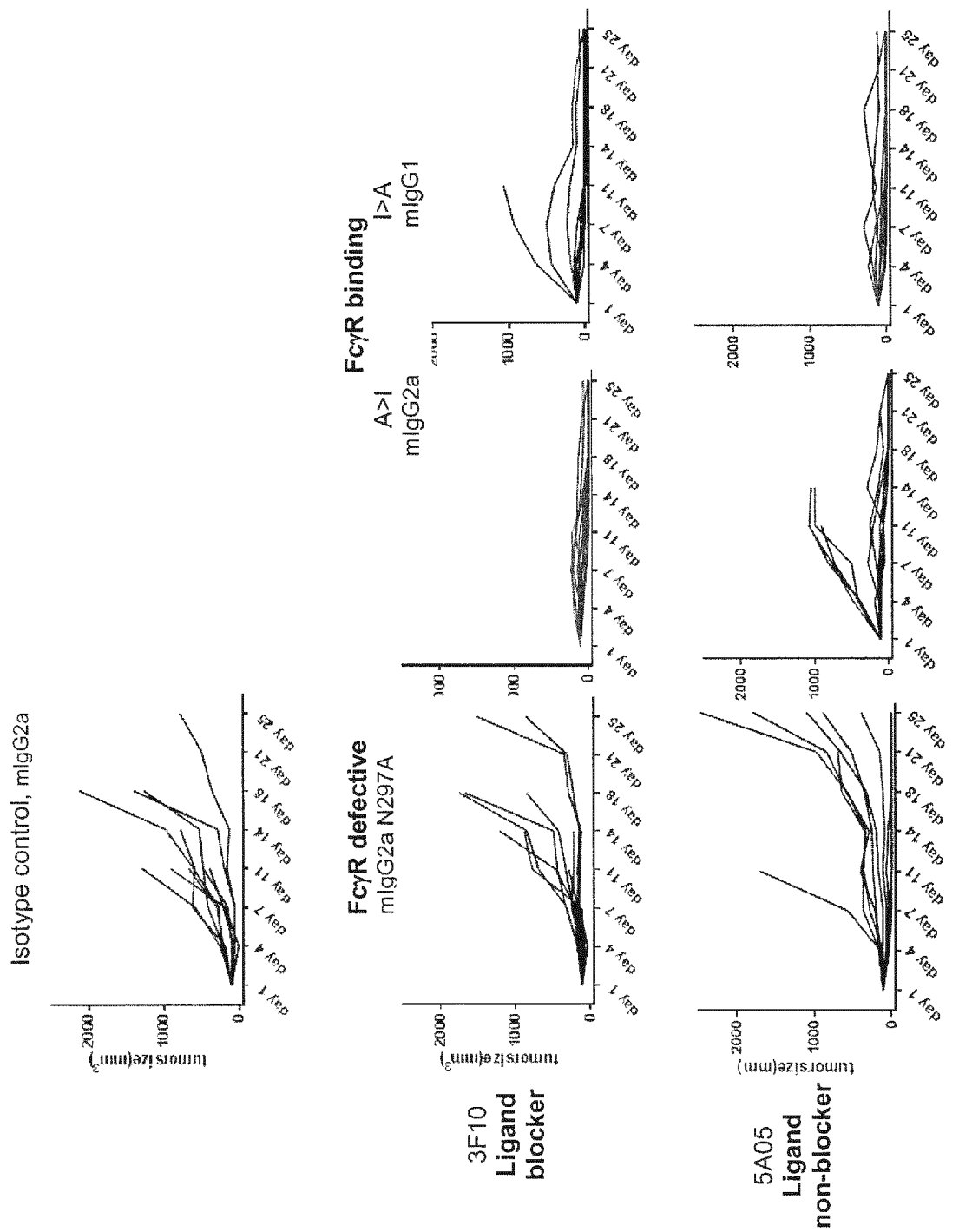

FIG. 11. For FIG. 11 A Balb/c mice were injected subcutaneously with 1×10$^6$ CT26 cells. After 8 days, at a mean tumor size of 3×3 mm mice were treated twice weekly with 10 mg/kg antibody i.p. as indicated in figures. Tumors were measured two times/week until they reached a diameter of 15 mm, where after the mice were terminated. The upper figure shows the tumor growth in isotype control treated mice, then the two figures below, in the left panel, show the antagonistic ligand-blocker antibody (middle figure) and the agonistic non-ligand blocking antibody (lower figure) in FcγR defective Ig format. The middle panel show the same antibodies in murine IgG2a format, engaging primarily activatory FcγRs and the right panel the antibodies in murine IgG1 format engaging primarily the inhibitory FcγRIIb. For FIG. 11 B surviving mice were followed for 70 days. As seen in the figures, the non-blocking agonistic antibody is most efficacious as tumor treatment in an IgG1 format engaging primarily the inhibitory FcγR. In addition, the agonistic antibody has FcγR independent anti-tumor effects as seen using the N297A format. On the other hand, the blocking antagonistic antibody is most efficacious as tumor treatment in an IgG2a format engaging primarily activatory FcγRs and has no effect in a format with defective FcγR binding. ***=p<0,001 compared to isotype control as calculated by Log-rank Mantel Cox test.

Figure 12:
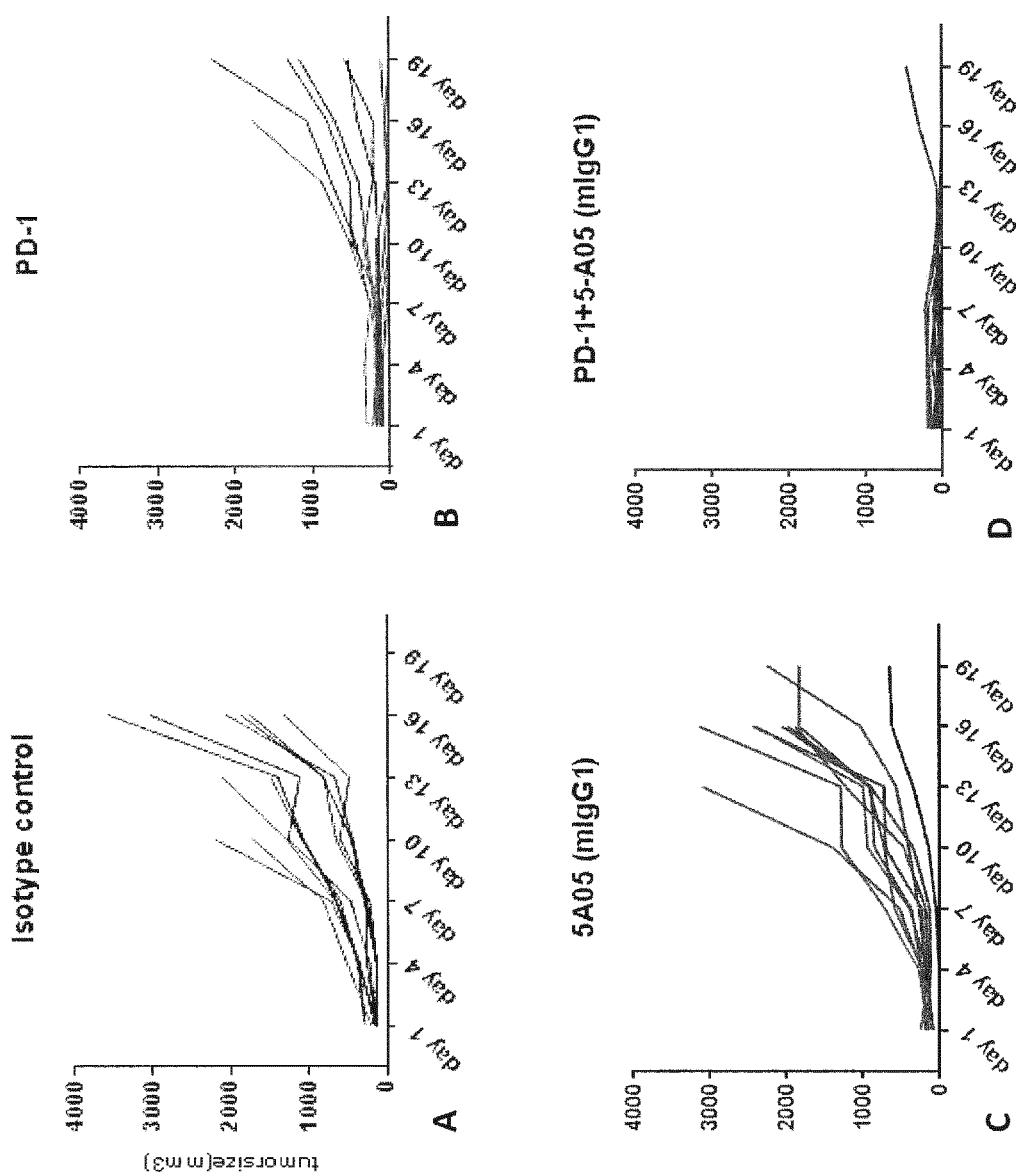

FIG. 12. C57/BL6 mice were injected subcutaneously with 1×10$^6$ MC38 cells. At a mean tumor size of 3×3 mm mice were treated twice weekly with 10 mg/kg antibody i.p. as indicated in figures. The figure shows tumor growth curves of individual mice. FIG. 12 A: isotype control, FIG. 12 B: PD-1 targeting antibody, FIG. 12 C: 5A05 antibody (surrogate antibody, ligand non-blocker, agonist), FIG. 12D: combination of 5A05 and PD1. Tumors were measured two times/week until they reached a diameter of 15 mm, where after the mice were terminated. FIG. 12 E shows survival curves of the four different treatment groups, *=p<0,05, ***=p<0,001 compared to isotype control as calculated by Log-rank Mantel Cox test.

Figure 13:
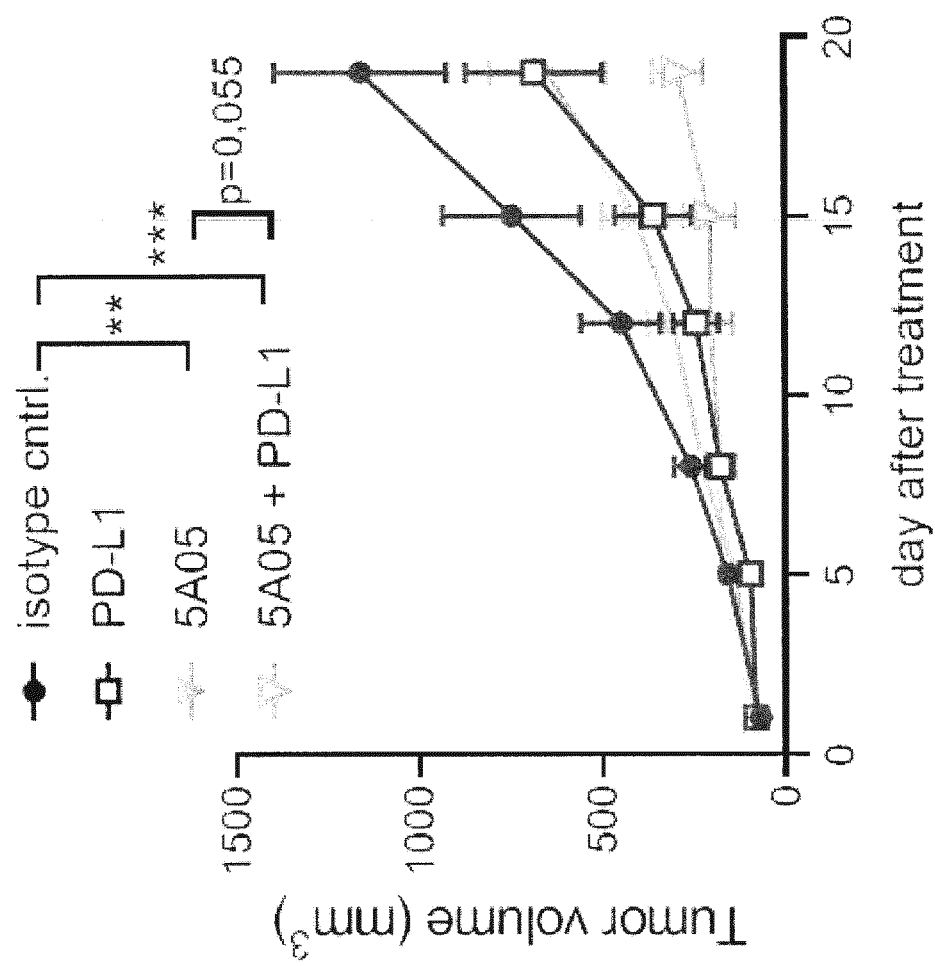

FIG. 13 shows that ligand blocking agonistic antibodies are effective as anti-tumor treatment in combination with anti-PD-L1. C57/BL6 mice were injected subcutaneously with 1×106 MC38 cells. At a mean tumor size of 5×5 mm, mice were treated twice with isotype control antibody or 5A05 (day 1 and 4), or four consecutive days with antiPD-L1 followed by a fifth injection two days later (in total five injections day 1,2,3,4 and 7), or a combination of both. All antibodies were administered at 10 mg/kg i.p. FIG. 13 show mean tumor growth+/−SEM, n=10/group. *=p<0,05, ***=p<0,001 as calculated using one-way ANOVA test.

Figure 14:
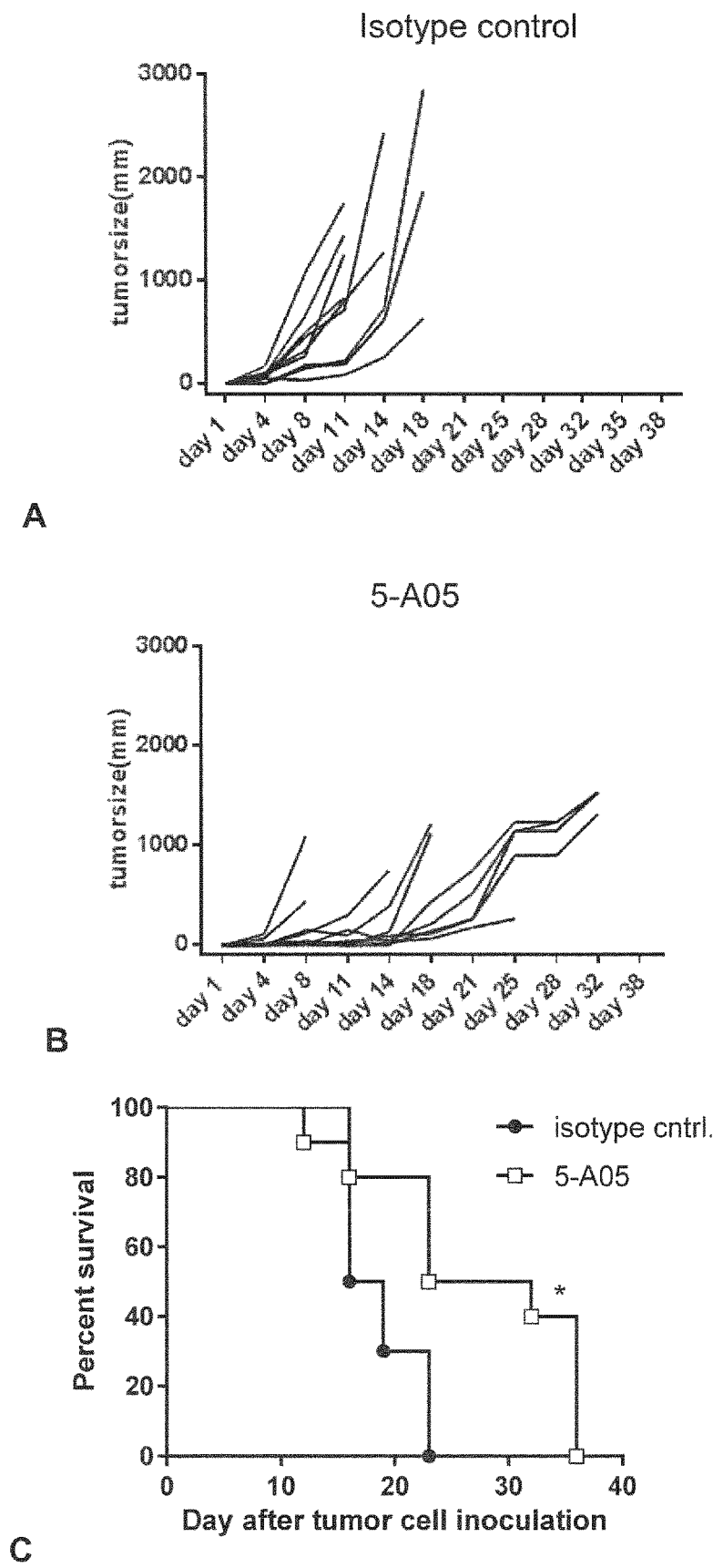

FIG. 14. C57/BL6 mice were injected subcutaneously with 1×10$^6$ B16 cells. After 3 days, mice were treated twice weekly with 10 mg/kg antibody i.p. Tumors were measured two times/week until they reached a diameter of 15 mm, where after the mice were terminated. FIG. 14 A: isotype control, FIG. 14 B: 5A05 antibody (surrogate antibody, ligand non-blocker, agonist). FIG. 14C shows survival curves for the two different treatment groups. *=p<0.05 compared to isotype control as calculated by Log-rank Mantel Cox test.

Figure 15:
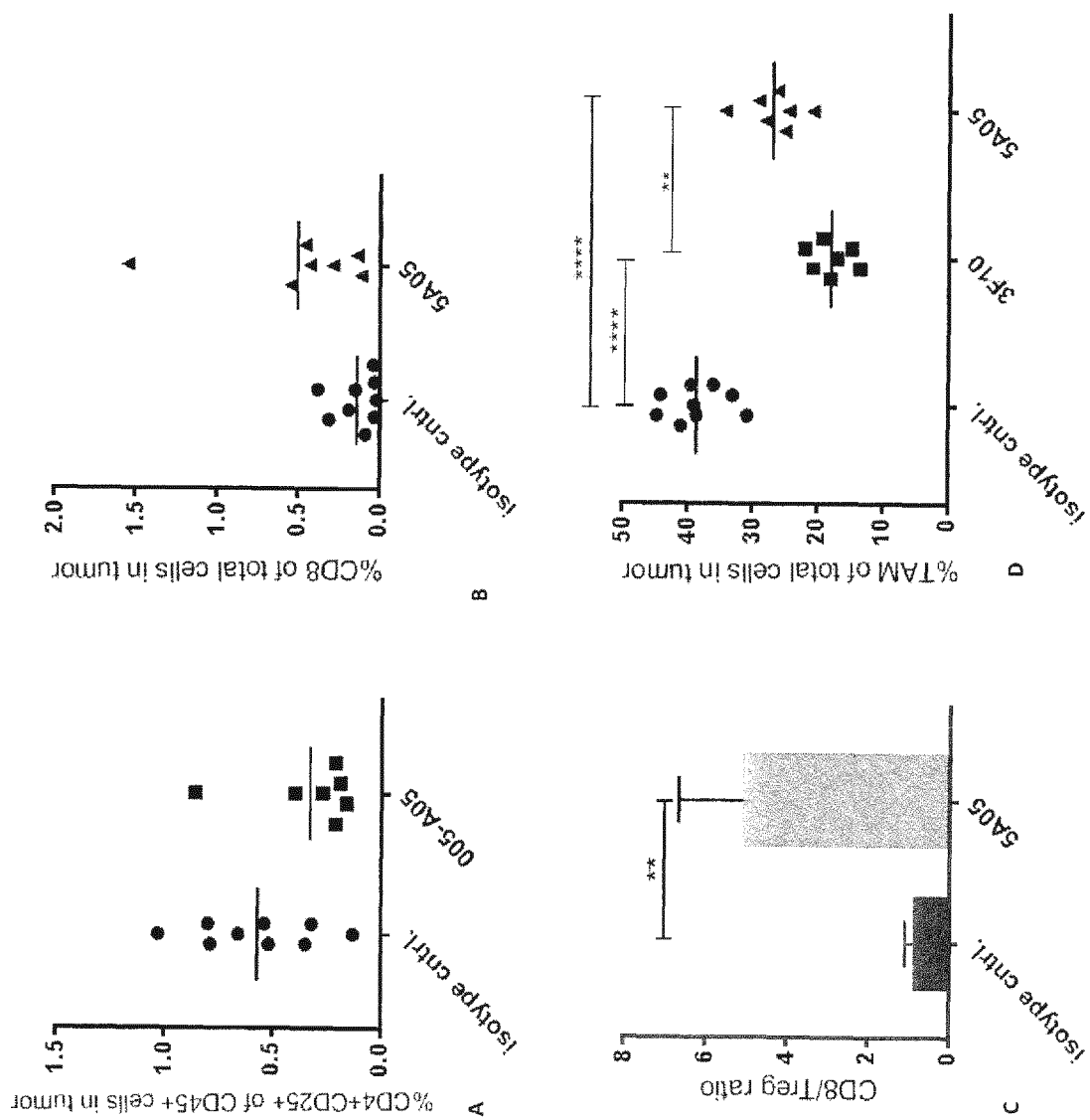

FIG. 15. Ligand non-blocking agonistic surrogate antibody 5A05 alters immune cell composition in tumors. Mice were inoculated with CT26 tumor cells as described and injected with antibodies as indicated once the tumors reached a size of approximately 7×7 mm. after 3 injections, at day 8 after treatment start, mice were sacrificed and tumors harvested. Tumor single cell suspensions were analyzed for immune cell content by FACS. A) Ligand non-blocking agonistic surrogate antibody 5A05 causes Treg depletion and B) $CD8^+$ T cell influx or expansion. This causes a shift in $Treg/CD8^+$ T cell ratio as depicted in C) Figure D) shows that not only T cells but also myeloid cells, here numbers of tumor associated macrophages (TAMs, defined as being $CD11b^+$ but negative for both Ly6G and Ly6C) are very significantly reduced. The ligand blocking antagonistic surrogate antibody 3F10 also modulates TAM numbers but is still significantly different from 5A05.

Figure 16:
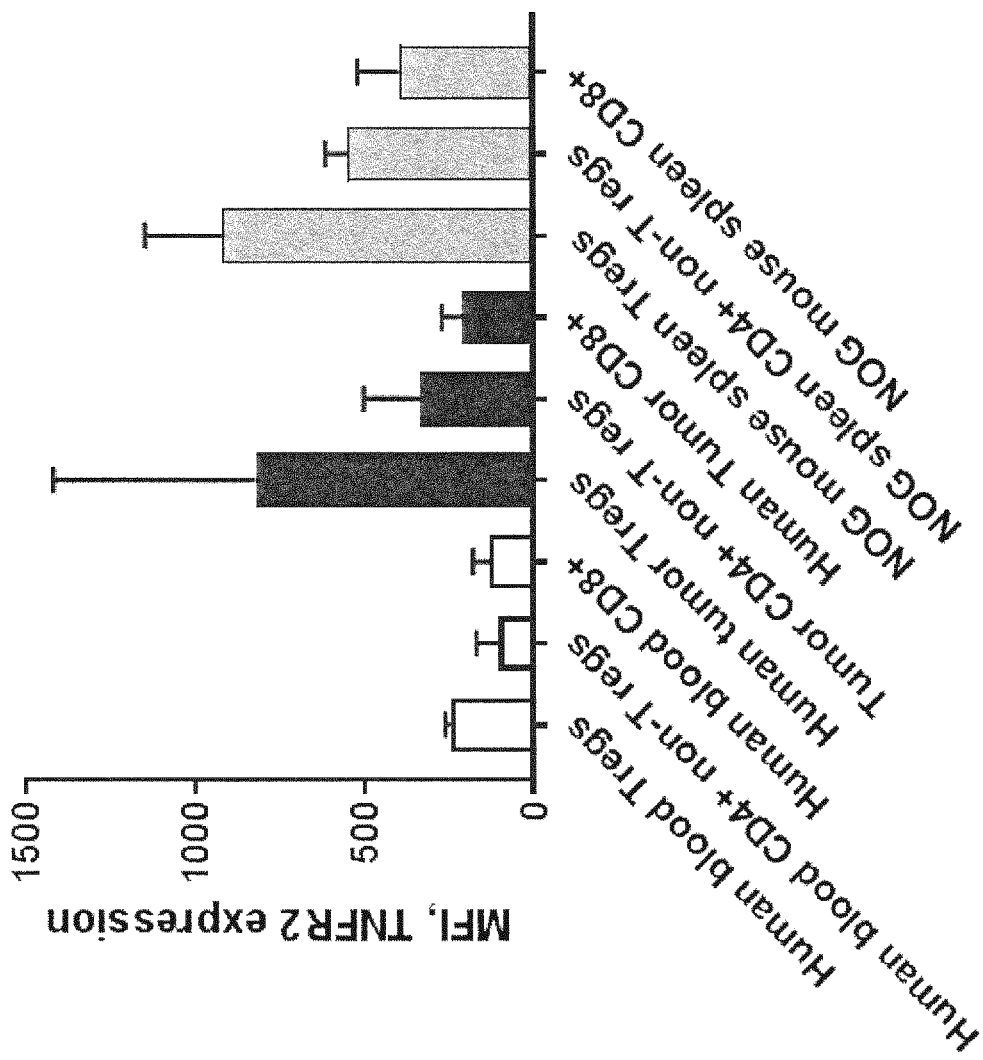

FIG. 16. NOG mice were injected i.v. with $15\text{-}20 \times 10^6$ PBMC cells. After 10-12 days, the spleens were removed from mice, single cell suspension prepared and TNFR2 expression was assessed by FACS. Previously, TNFR2 expression had been assessed on T cells retrieved from blood and tumor samples from 3 or 9 cancer patients respectively. As shown in the figure, the TNFR2 expression on Tregs and $CD8^+$ T cells are very comparable between the human T cells grown and activated in vivo in the NOG mice, and T cells from human tumors.

Figure 17:
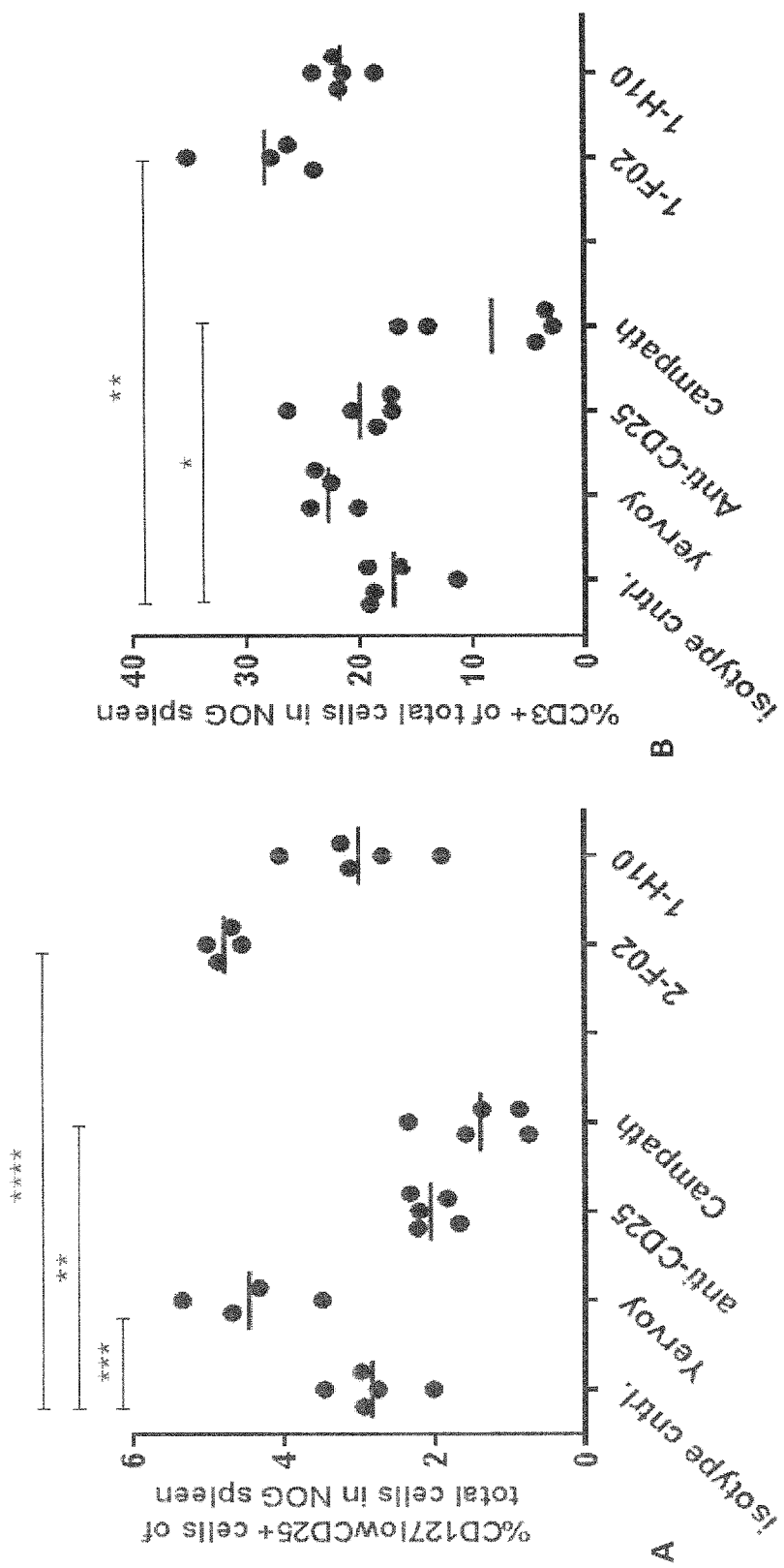

FIG. 17. NOG mice were injected i.v. with $15\text{-}20 \times 10^6$ PBMC cells. After 10-12 days, the spleens were removed from mice, single cell suspension prepared and cells in were analyzed using FACS. FIG. 17 A shows the mean percentage of stained Tregs defined as $CD45^+CD3^+CD4^+CD25^+CD127^{low/neg}$ out of the total numbers of cells in the spleen. FIG. 17 B shows the mean percentage of T cells ($CD3^+$) of the total numbers of cells in the spleen. As shown in FIG. 17, the ligand non-blocking agonistic antibody 1F02 increases the number of Tregs (expressing the highest levels of TNFR2) as well as total number of T cells in this model. As comparison, the ligand blocker antagonistic antibody 1H10 does not have this effect.

Figure 18:
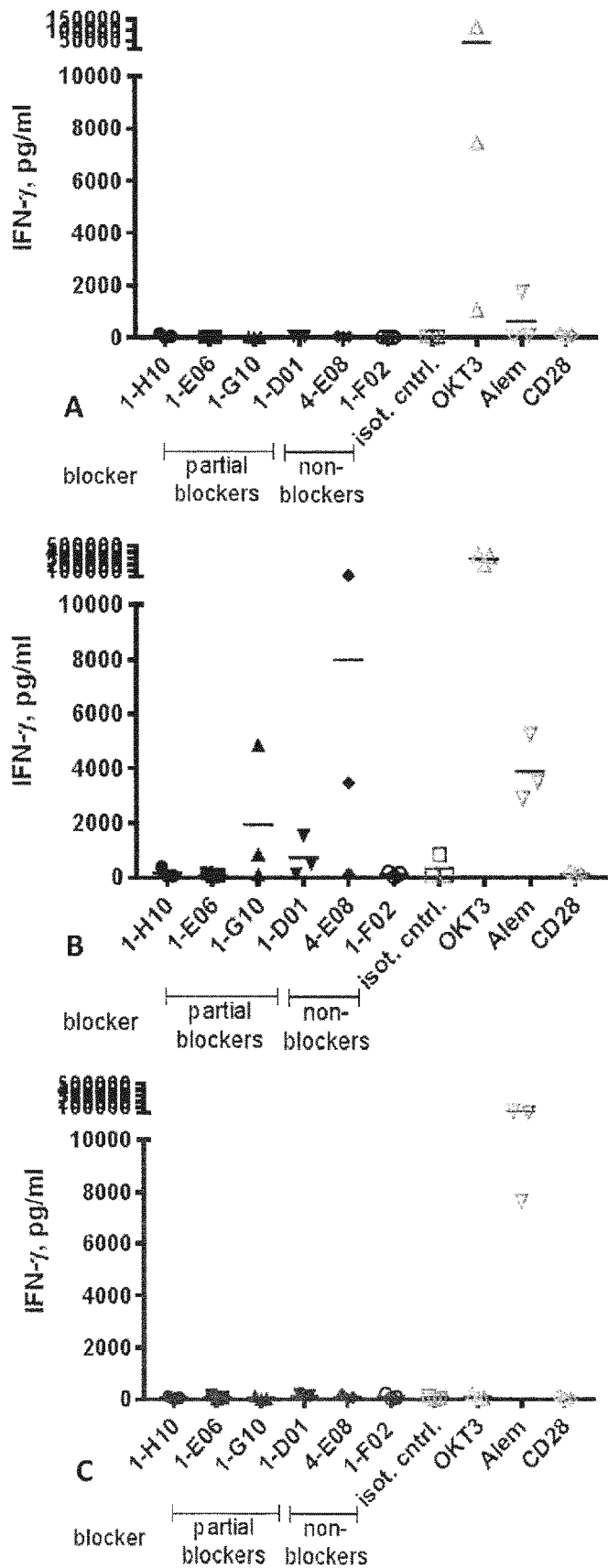

FIG. 18. IFN-γ release induced by various TNFR2 specific antibodies was measured in three different in vitro systems. As positive controls, an anti-CD3 antibody—OKT3 or Muromonab-CD3, an anti-CD52 antibody—Alemtuzumab, and an anti-CD28 antibody were used. Isotype control was used as a negative control. Each dot represents PBMC from one human donor. FIG. 18 A shows results from high density cell cultures were PBMCs were cultured at $1\times10^7$ cells/ml. After 48 h, 10 µg/ml antibody was added and incubated for 24 h. As seen in the figure, both Alemtuzumab and OKT3 induced significant IFN-γ release but not any of the TNFR2 specific antibodies. FIG. 18 B shows Solid Phase in vitro cultures performed by coating wells of a 96-well plate with antibodies before adding PBMCs. Again, both Alemtuzumab and OKT3 induced significant IFN-γ release along with some of the TNFR2 specific antibodies, particularly in one of the donors. FIG. 18 C shows stimulation of whole blood with antibody and here Alemtuzumab induced significant IFN-γ release but not any of the TNFR2 specific antibodies.

Figure 19:
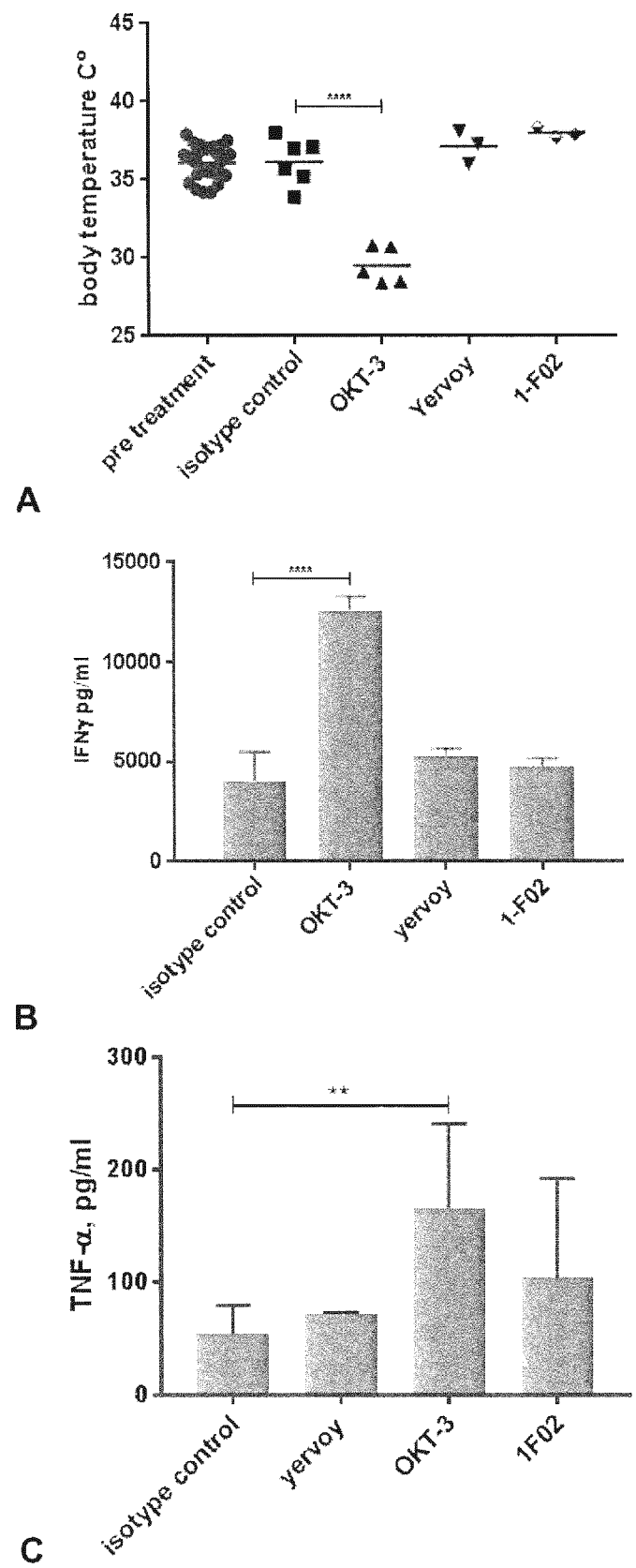
Figure 20:
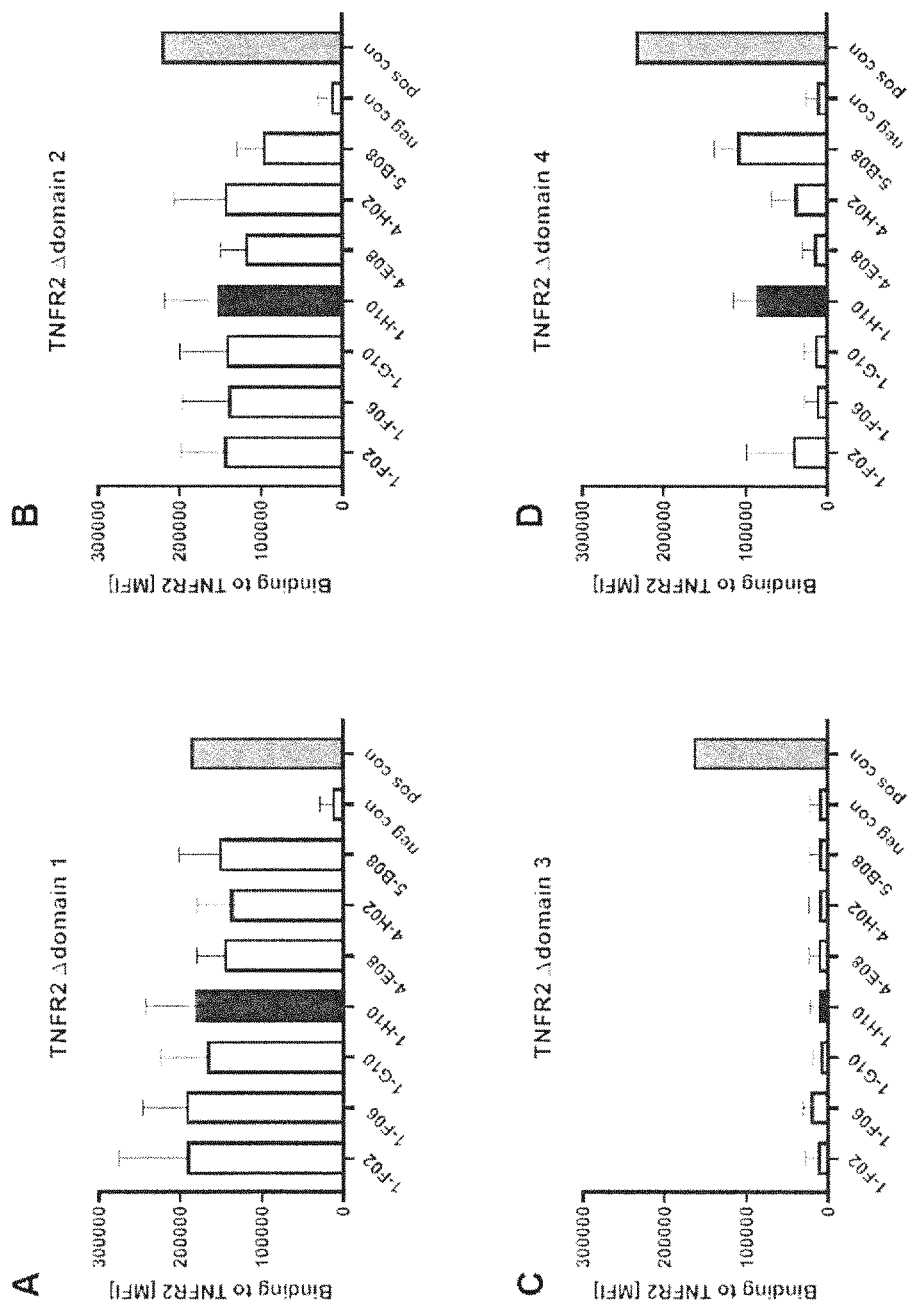

FIG. 19: NOG mice were injected i.v. with $25\text{-}\times10^6$ PBMC cells. After 14 days, when the blood of the mice was shown to consist of approximately 40% human T-cells, mice were treated with 10 µg antibody. Body temperature was measured 1 h post injection (FIG. 19 A). The experiment was terminated 5 h post injection and blood was analyzed for IFN-γ (FIG. 19 B) or TNF-α. (FIG. 19 C) content. **=p<0,0001 and =p<0.01 as calculated with one-way ANOVA FIG. 20 shows binding to TNFR2 variants lacking individual domains. Antibody binding to TNFR2 variants expressed on HEK cells were tested in a flow cytometry approach. Lack of domain 1 and 2 does not significantly affect binding (FIGS. 20 A and B), while 3 and partially 4 completely abrogates interaction between the antibody and TNFR2 (FIGS. 20 C and D). Similarly lack of domain 1+3 prevents binding of all antibodies (except 1F06), completely (FIG. 20 E), while the lack of domain 2+4 abrogate binding completely for the agonistic antibodies (1F02, 1F06, 4E08) and significantly reduces binding also for the antagonists (1H10, 4H02, 5B08) (FIG. 20 F). Dark grey indicates positive control and white indicates negative control antibody.

Figure 21:
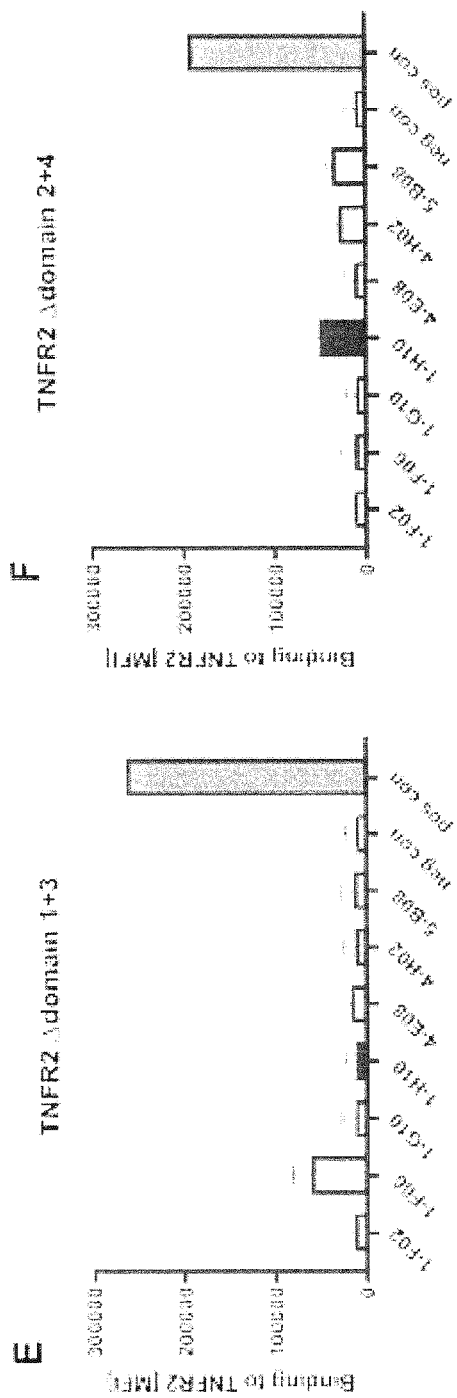

FIG. 21 shows comparison of amino acid sequence of human (H-D3) and mouse (M-D3) domain 3 of TNFR2. Similar amino acids are marked in white, while differences are marked in grey. The five sequences below represent the 5 different constructs the antibodies are tested against. Exchanges of human-to-mouse sequence are underlined, while the non-marked sequence is completely human. Domains 1, 2 and 4 are human and do not contain any substitutions or mutations.

Figure 22:
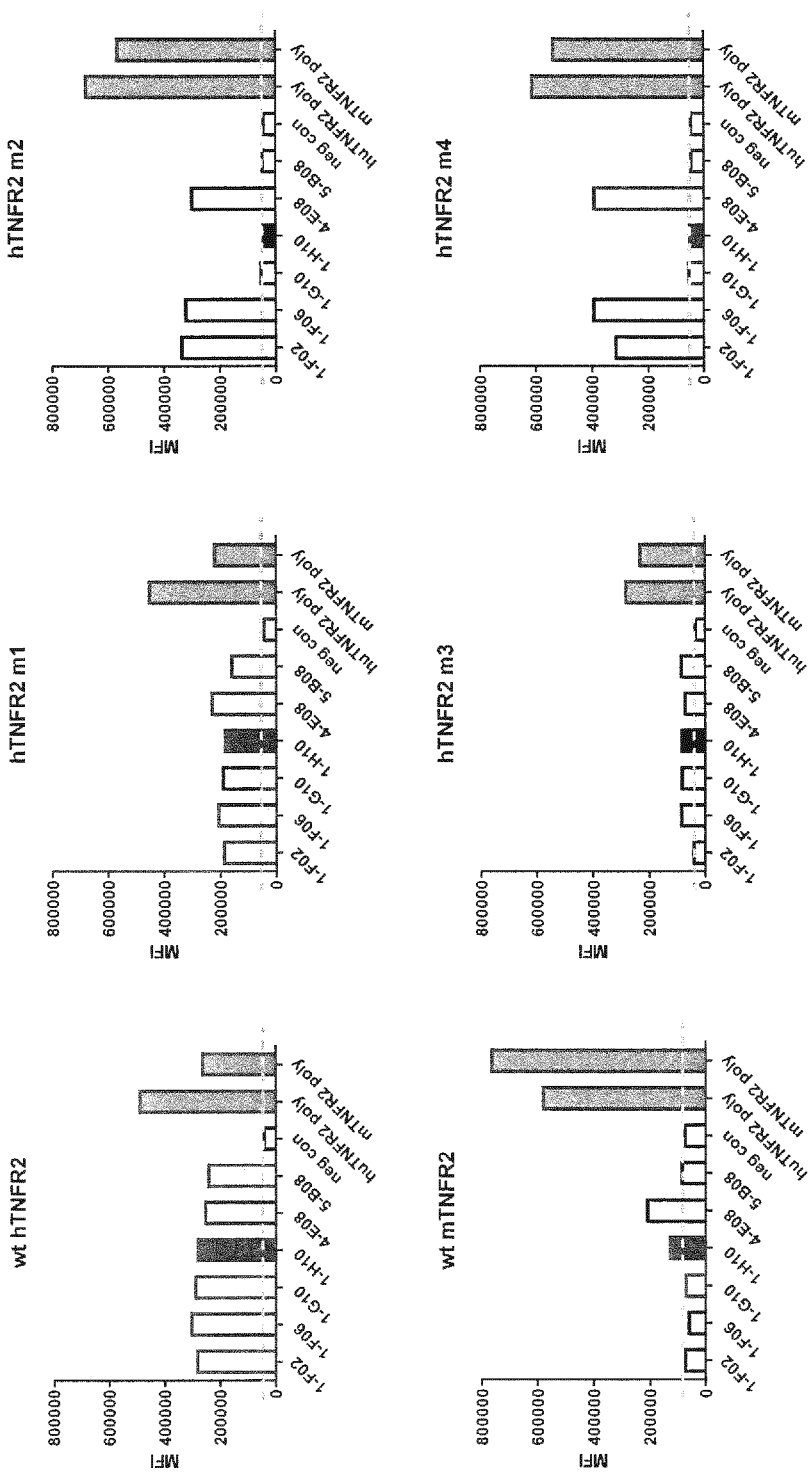

FIG. 22. binding to the wild type human and mouse TNFR2 is shown in the left panels. Mutated hTNFR2 constructs (m1, m2, m3 and m4) were used to narrow down the binding site for different anti hTNFR2 antibodies. Flow cytometry analysis revealed that mutations in aa 119-132 do not affect antibody binding, but in aa 151-160 completely abrogate binding of all antibodies. Mutations in 134-144 disrupt binding for blocking and antagonistic antibodies only but does not significantly affect the agonistic antibodies. Dark grey bars indicate positive control and white negative control antibody. Dashed line is the level of the negative control antibody.

EXAMPLES

Specific, non-limiting examples which embody certain aspects of the invention will now be described.

In many of the examples, in particular the in vivo examples, the antibody 5-A05 has been used. This is a mouse antibody, which is a surrogate antibody to the human antibodies disclosed herein. It has been selected as a surrogate antibody based on its similar characteristics as a ligand non-blocking agonistic antibody with good EC50 value.

In some of the examples and figures a slightly different naming of the antibody clones is used, for example, clone 001-F02 is sometimes shortened to 1-F02 or 1F02, 005-B08 is sometimes shortened to 5-B08 or 5B08 etc.

Example 1—Generation of TNFR2 Specific Antibodies (See Also FIG. 1 and the Above Description of this Figure.)
Isolation of scFv Antibody Fragments
The n-CoDeR® scFv library (BioInvent, Söderlind E, et al Nat Biotechnol. 2000; 18(8):852-6) was used to isolate scFv antibody fragments recognizing human or mouse TNFR2.

The phage library was used in three consecutive pannings against recombinant human or mouse protein (Sino Biological). After phage incubation, the cells were washed to remove unbound phages. Binding phages were eluted with trypsin and amplified in *E. coli*. The resulting phage stock was converted to scFv format. *E. coli* was transformed with scFv bearing plasmids and individual scFv clones were expressed.

Identification of Unique TNFR2 Binding scFv

Converted scFv from the third panning were assayed using a homogeneous FMAT analysis (Applied Biosystems, Carlsbad, CA, USA) for binding to 293 FT cells transfected to express human or mouse TNFR2 or a non-related protein.

Briefly, transfected cells were added to clear-bottom plates, together with the scFv-containing supernatant from expression plates (diluted 1:7), mouse anti-His Tag antibody (0.4 µg/ml; R&D Systems) and an APC-conjugated goat anti-mouse antibody (0.2 µg/ml; cat. no. 115-136-146, Jackson Immunoresearch). FMAT plates were incubated at room temperature for 9 h prior to reading. Bacterial clones binding TNFR2 transfected cells but non cells transfected with a non-related protein were classified as actives and cherry picked into 96-well plate.

IgG Binding to TNFR2 in ELISA 96-well plates (Lumitrac 600 LIA plate, Greiner) were coated overnight at 4° C. with recombinant human or mouse TNFR2-Fc protein (Sino Biological) at 1 pmol/well. After washing, titrated doses of anti-TNFR2 mAbs from 20 µg/ml to 0.1 ng/ml (133 nM to 1 pM) were allowed to bind for 1 hour. Plates were then washed again, and bound antibodies were detected with an anti-human-F(ab)-HRP secondary antibody (Jackson ImmunoResearch) diluted in 50 ng/ml. Super Signal ELISA Pico (Thermo Scientific) was used as substrate and the plates were analyzed using Tecan Ultra Microplate reader.

The data, which are shown in Table 5 and in FIG. 1 A-D, show that the human anti-TNFR2 antibodies all bind to human TNFR2 protein. The EC50 values are ranging from 0.082 nM for 1-008 to 4.4 nM for 1-A09.

In addition, the mouse antibody surrogate clones 3-F10 and 5-A05 also bind to mTNFR2 protein. These two clones bind with a very similar affinity (Table 5 and FIG. 1E).

TABLE 5

EC50 values of antibodies binding to TNFR2 protein (human protein except for clone 3F10 and 5A05)

| Clone | $EC_{50}$ (nM) |
| --- | --- |
| 1-C08 | 0.082 |
| 1-E06 | 0.20 |
| 1-G10 | 0.29 |
| 1-H10 | 0.29 |
| 4-H02 | 0.20 |
| 5-B02 | 0.15 |
| 5-B08 | 0.17 |
| 1-G04 | 1.7 |
| 1-H09 | 0.30 |
| 1-D01 | 0.37 |
| 5-F10 | 0.22 |
| 1-B11 | 0.25 |
| 1-C07 | 0.26 |
| 1-B05 | 0.23 |
| 1-F02 | 0.31 |
| 1-F06 | 0.15 |

TABLE 5-continued

EC50 values of antibodies binding to TNFR2 protein (human protein except for clone 3F10 and 5A05)

| Clone | $EC_{50}$ (nM) |
| --- | --- |
| 4-E08 | 0.38 |
| 1-G05 | 0.54 |
| 1-A09 | 4.4 |
| 1-B09 | 0.18 |
| 1-C03 | 0.75 |
| 1-C05 | 0.38 |
| 3-F10 (mouse) | 0.97 |
| 5-A05 (mouse) | 1.4 |

Example 2—Specificity of Antibodies (See Also FIGS. 2-5 and the Above Description of these Figures.)

Isolation of CD4+ T Cells

PBMCs from human buffy coats and Cynomolgus macaques (*M. fascicularis*) whole blood were isolated using Ficoll-Paque PLUS (GE Healthcare) gradients. CD4+ T cells were isolated from PBMCs by magnetic cell sorting using CD4+ T cell isolation kit (human) or CD4 MicroBeads, non-human primate (Cynomolgus) both from Miltenyi. Mouse CD4+ T cells were isolated from spleen using CD4+ T cell isolation kit (mouse) from Miltenyi.

Titration of TNFR2 Specific n-CoDeR® Antibodies

The ability and affinity of TNFR2 n-CoDeR® antibodies to bind TNFR2 expressed on cells were obtained using in vitro activated CD4+ T cells. Human CD4+ T cells were stimulated with 50 ng/ml rhIL-2 (R&D systems) and Dynabeads® T-Activator CD3/CD28 for T-Cell Expansion and Activation (Gibco) 2-3 days at 37 degrees. In vitro activated cells were labelled with increasing amount of n-CoDeR® antibodies specific for TNFR2 or isotype control, ranging from 0.002-267 nM. Cells were then incubated with an APC conjugated a-human IgG secondary ab (Jackson) followed by analysis by flow cytometry (FACSVerse, BD). The resulting titration curves are shown in FIG. 3 A-D, Mouse CD4+ T cells were stimulated with 135U/ml rmIL-2 (R&D systems) and Dynabeads® T-Activator CD3/CD28 for T-Cell Expansion and Activation (Gibco) 2-3 days at 37 degrees. In vitro activated cells were labelled with increasing amount of n-CoDeR® antibodies specific for TNFR2 or isotype control, ranging from 0.00003-133 nM. Cells were then incubated with an APC conjugated a-mouse IgG secondary ab (Jackson) followed by analysis by flow cytometry (FACSVerse, BD), The titration curves are shown in FIG. 3E, The EC50 values for the titration curves were calculated in Microsoft Excel and are shown in Table 6, For the human antibodies the EC50 values differed from 0.6n M (4-H02) to 52.7 nM (1-003). The mouse antibodies bound to in vitro activated cells with similar affinity (0,072 nM (3-F10) and 0.11 nM (5-A05)).

Specificity of TNFR2 n-CoDeR® Antibodies

The specificity of TNFR2 antibodies to TNFR2 were obtained in FACS blocking experiments with a commercial polyclonal TNFR2 antibody (R&D systems). CD4+ T cells (mouse and human) stimulated 2-3 days with 50 ng/ml rhIL-2 (R&D systems) (human)/135U/ml rm IL-2 (R&D systems) (mouse) and Dynabeads® T-Activator CD3/CD28 for T-Cell Expansion and Activation (Gibco) were blocked with 40 µg/ml polyclonal TNFR2 antibody (R&D systems) for 30 min, immediately followed by 15 min incubation with TNFR2 n-CoDeR® antibodies or isotype control. The concentration of n-CoDeR® antibodies used was based on the titration curves for the individual TNFR2 n-CoDeR® antibodies and a suboptimal concentration for each antibody was chosen. Cells were then washed and incubated 30 min with an APC conjugated secondary antibody (Jackson). Cells were analyzed by flow cytometry (FACSVerse, BD). All binding of TNFR2 specific n-CoDeR® antibodies (both human and mouse) could be blocked by a polyclonal TNFR2 antibody as shown in FIG. 4. These results verifying that TNFR2 n-CoDeR® antibodies specifically bind TNFR2 on in vitro activated CD4+ T cells.

Epitope Mapping of TNFR2 Specific n-CoDeR® Antibodies Against the TNFR2 Antibody Clone MR2-1

The TNFR2 antibody clone MR2-1 (Invitrogen) binds a specific domain of the TNFR2 protein. If the TNFR2 specific n-CoDeR® antibodies bound to the same domain as MR2-1 was tested by FACS blocking experiments.

Human CD4+ T cells were stimulated 2-3 days with 50 ng/ml rhIL-2 (R&D systems) and Dynabeads® T-Activator CD3/CD28 for T-Cell Expansion and Activation (Gibco). Activated cells were blocked with 40 µg/ml MR2-1 (black bars in FIG. 5A), TNFR2 specific n-CoDeR® antibody/polyclonal TNFR2 (R&D systems) (black bars in FIG. 6B) or PBS (grey bars in FIG. 5). After 30 min incubation, cells were immediately stained for TNFR2 specific n-CoDeR® antibody/pTNFR2 (FIG. 5A) or MR2-1 (FIG. 5B) for 15 min. Cells in FIG. 5A was also incubated with an APC conjugated secondary a-human IgG reagent (Jackson). All cells were analyzed by flow cytometry (FACSVerse, BD). Since the percentage of MR2-1+ cells were the same for n-CoDeR® blocked as non-blocked cells (FIG. 5B) and the binding of n-CoDeR® antibodies were the same with or without MR2-1 block (FIG. 5A) these n-CoDeR® antibodies probably bind other epitopes of the TNFR2 protein than the MR2-1 antibody.

Binding of TNFR2 n-CoDeR® Antibodies to Cynomolgus

To validate the cross-reactivity of TNFR2 antibodies to Cynomolgus, Cynomolgus CD4+ T cells were stimulated 2 days with 50 ng/ml PMA (Sigma) and 100 ng/ml Ionomycin (Sigma). Cells were incubated with TNFR2 specific n-CoDeR® antibodies at 3 different concentrations (0.1, 1 and 10 µg/ml) and then incubated with an APC conjugated secondary a-human IgG reagent (Jackson). Cells were analyzed by flow cytometry (FACSVerse, BD) and the result show that most of the human TNFR2 specific n-CoDeR® antibodies could bind Cynomolgus TNFR2, the results for the individual antibodies are presented in FIG. 4.

In summary, the data in example 2 show that the human antibodies specifically bind to TNFR2 endogenously expressed on human immune cells. Furthermore, the data show that this binding can be blocked by adding a polyclonal commercially available antibody against TNFR2, which indicates very high specificity for TNFR2. The same is true for the surrogate clones 3F10 and 5A05 regarding murine cells expressing murine TNFR2. Also, the binding of the human clones is unaffected by MR2-1 antibodies showing a different epitope specificity compared to MR2-1. T

TABLE 6

$EC_{50}$ values calculated on the titration of TNFR2 specific antibodies to in vitro activated CD4+ T cells.

| Clone | $EC_{50}$ (nM) |
|---|---|
| 1-C08 | 2.6 |
| 1-E06 | 4.1 |

TABLE 6-continued $EC_{50}$ values calculated on the titration of TNFR2 specific antibodies to in vitro activated CD4+ T cells.

| Clone | $EC_{50}$ (nM) |
|---|---|
| 1-G10 | 3.3 |
| 1-H10 | 1.1 |
| 4-H02 | 0.59 |
| 5-B02 | 0.80 |
| 5-B08 | 1.2 |
| 1-G04 | 18 |
| 1-H09 | 16 |
| 1-D01 | 3.9 |
| 5-F10 | 32 |
| 1-B11 | 27 |
| 1-C07 | 36 |
| 1-B05 | 1.5 |
| 1-F02 | 0.79 |
| 1-F06 | 2.5 |
| 4-E08 | 2.3 |
| 1-G05 | 0.66 |
| 1-A09 | 48 |
| 1-B09 | 29 |
| 1-C03 | 53 |
| 1-C05 | 12 |
| 3-F10 (mouse) | 0.072 |
| 5-A05 (mouse | 0.11 |

Example 3—Test of Ligand Blocking Characteristics (See Also FIGS. 6-7 and the Above Description of these Figures.)

ELISA Method 96-well plates were coated with hTNFRII (Sinobioologicals Cat nr10414-H08H) or mTNFRII (Sinobioologicals Cat No. 50128 M08H) at 2.5 pmol/well in ELISA coating buffer (0.1 M sodium carbonate pH 9.5) and incubated overnight at 4° C. After washing in ELISA wash buffer (PBS with 0.05% Tween20), the plates were incubated under slow agitation for 1 h in room temperature with n-CoDeR® mAbs at 10 µg/ml (one-dose ELISA) or 33 nM and subsequent 1:2 dilutions (titration ELISA) in block buffer containing 0.45% fish gelatin. Subsequently, recombinant hTNF-α-bio (R&D Cat. No. BT210) or mTNF-α (Gibco Cat. No. PMC3014) were added at a final concentration of 5 nM and 2 nM respectively and allowed to incubate for another 15 min. Thereafter, plates were washed. For the human ELISAs, Streptavidin-HRP (Jackson Cat No. 016-030-084) diluted 1:2000 in block buffer were added and again incubated for 1 h at room temperature followed by washes first in ELISA buffer and then in Tris buffer (pH 9.8). The substrate (Super Signal ELISA Pico from Thermo Scientific Cat. No. 37069) were thereafter diluted according to the manufacturers instruction, added to the wells and incubated in darkness for 10 min before reading in a Tecan Ultra. For the mouse ELISAs, rabbit anti-mTNF-α (Sinobiologicals Cat. No. 50349-RP02) diluted to 1 µg/ml in was added and allowed to incubate for 1 h in room temperature. After washing, anti-Rabbit-HRP diluted 1:10 000 in block buffer was added and again incubated for 1 h at room temperature. Substrate adding and reading were performed as above.

The data for anti-human and anti-mouse antibodies is presented in Tables 7 and 8, respectively, below, and in FIGS. 6 and 7.

TABLE 7

EC50 values of ligand blocking human antibodies: Antibodies were titrated, and EC 50 values were calculated.

| Clone | EC50 (nM) | Block |
|---|---|---|
| 001-H10 | 0.9 | Complete |
| 004-H02 | 0.4 | Complete |
| 005-B08 | 0.3 | Complete |
| 005-B02 | 0.2 | Complete |
| 001-E06 | 0.3 | Partial |
| 001-G10 | 1.6 | Partial |
| 001-C08 | 1.1 | Partial |
| 001-H09 | 1.4 | Partial |
| 005-F10 | 0.03 | Partial |
| 001-G04 | 3.2 | Partial |
| 001-B11 | 1.0 | Weak |
| 001-C07 | 0.8 | Weak |
| 001-D01 | 1.4 | Weak |

TABLE 8

EC50 values of ligand blocking murine antibodies: Antibodies were titrated, and EC 50 values were calculated.

| Clone | EC50 (nM) | Block |
|---|---|---|
| 3-F10 | 1.9 | Complete |
| 4-C01 | 2.7 | Complete |
| 4-A06 | 2.0 | Partial |
| 4-A07 | >500 | Partial |
| 4-F06 | 6.2 | Partial |
| 5-C09 | 8.6 | Partial |
| 2-D09 | 4.4 | Partial |
| 4-B12 | >500 | Partial |
| 3-G06 | 13 | Partial |
| 2-H01 | 25 | Weak |
| 4-C02 | >500 | Weak |
| 4-G09 | 2.6 | Weak |
| 4-C03 | 8.3 | Weak |

Blocking Definitions

Complete blockers are defined as reducing the TNF-α binding with more than 98%

Partial blockers are defined as reducing the TNF-α binding with 60-98%

Weak blockers are defined as reducing the TNF-α binding with less than 60%

Figure 7A:
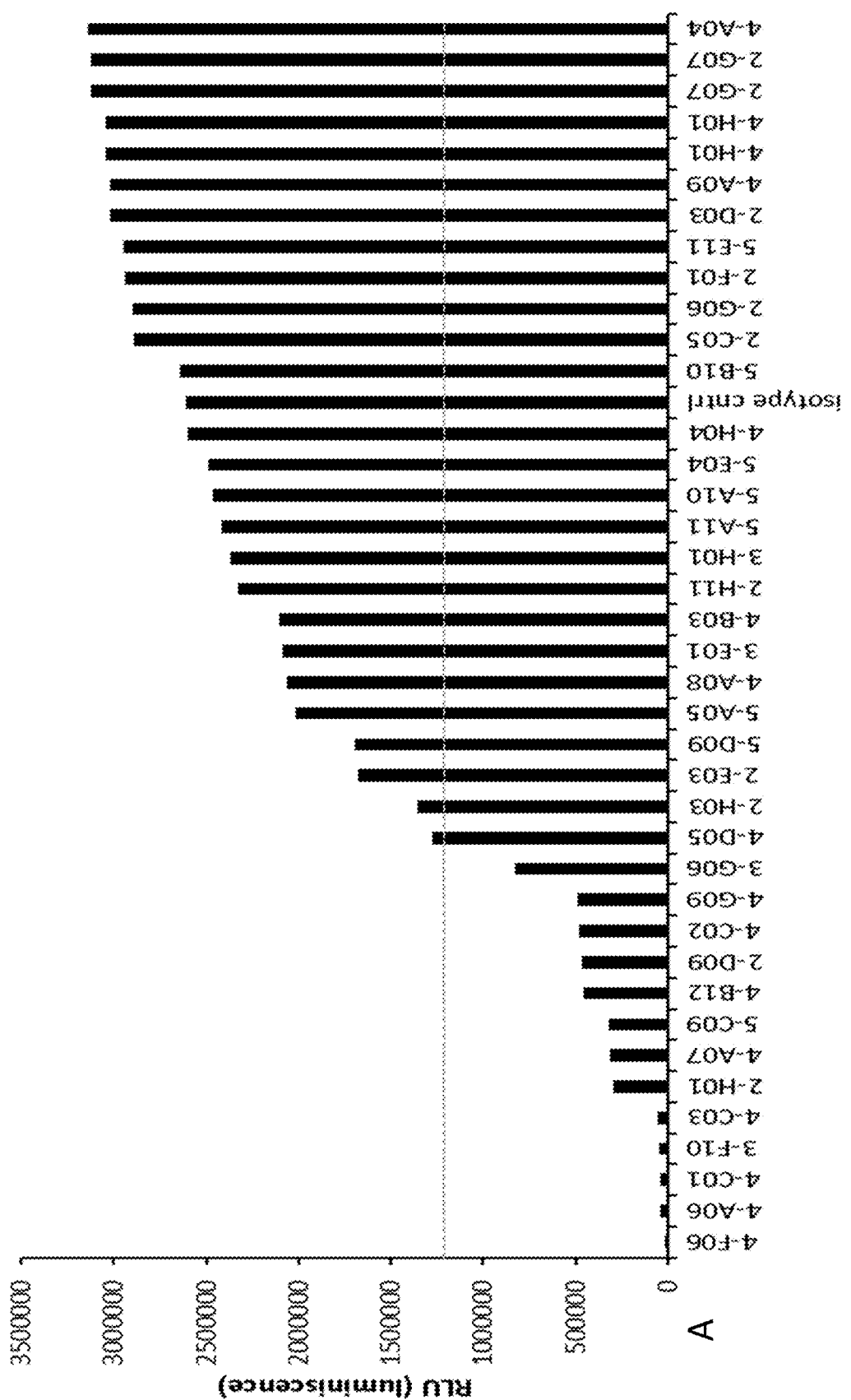
Figure 7C:
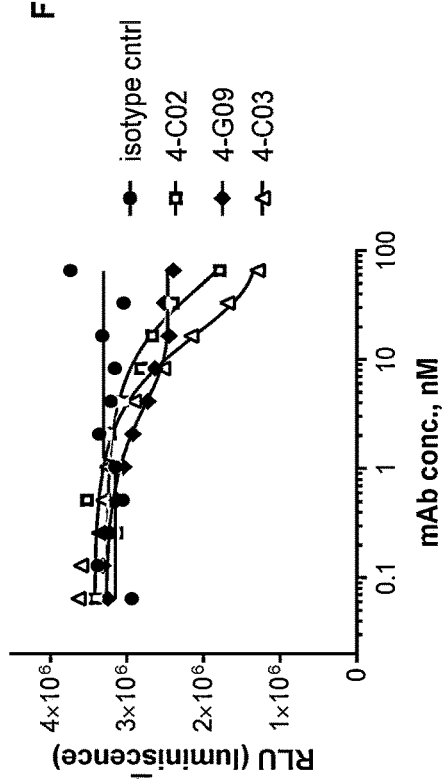
Figure 7E:
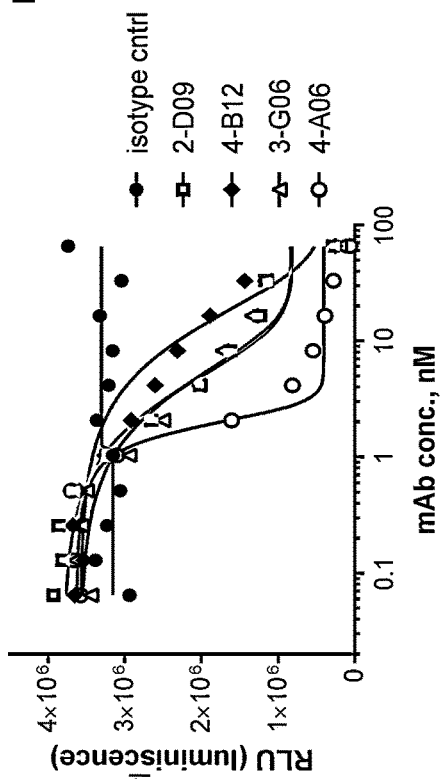
Figure 7B:
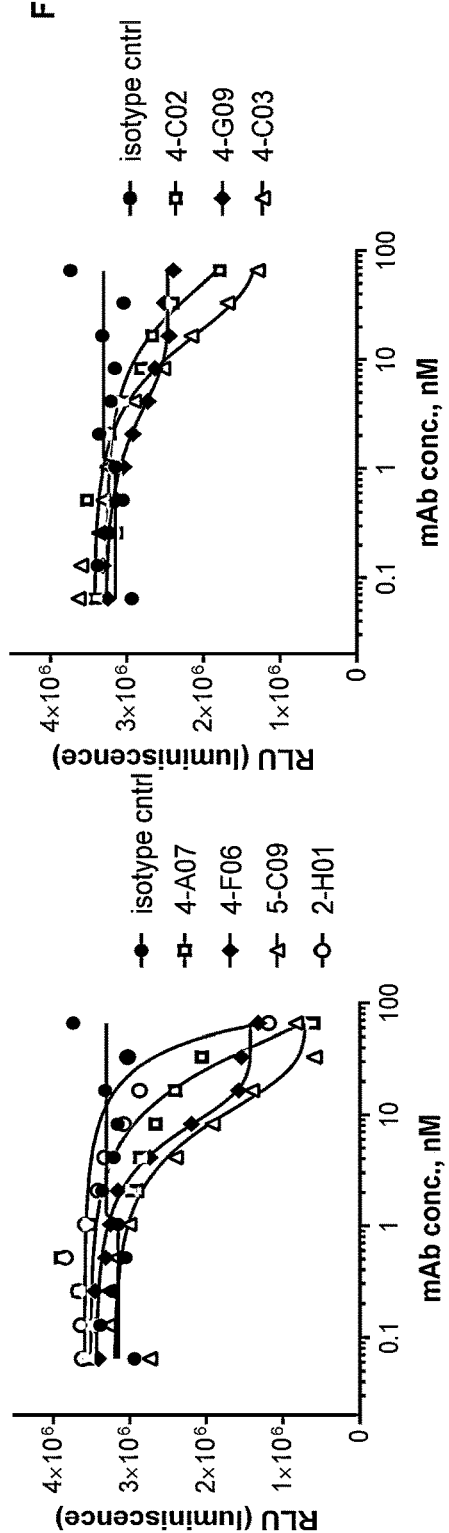
Figure 7D:
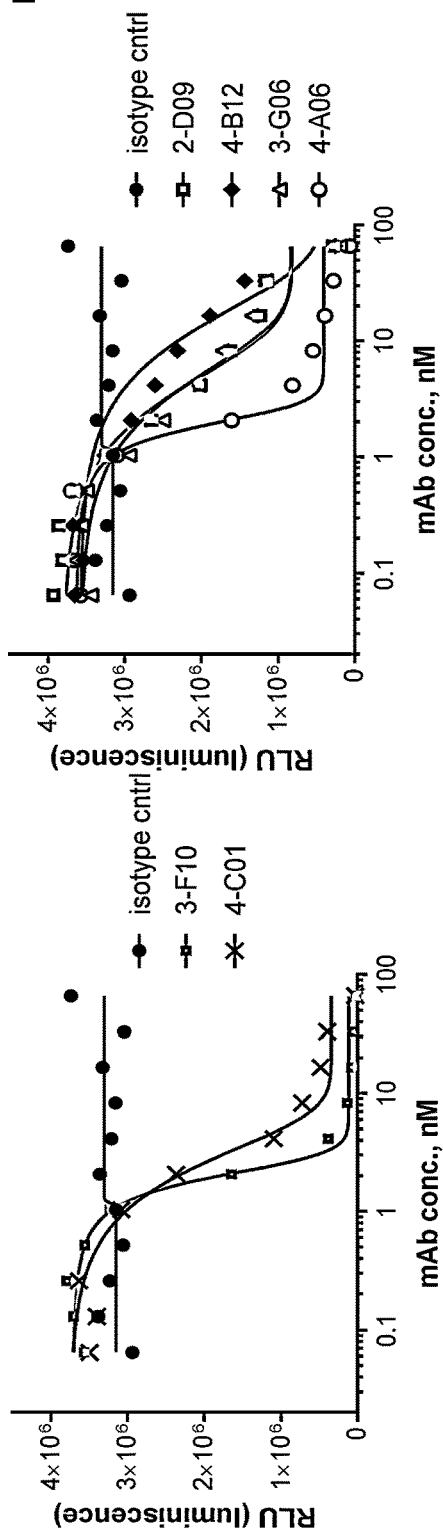

Non-blocking antibodies are defined as not reaching more than 50% block in high-dose, one-point ELISA as shown in FIGS. 6A and 7A The data shown in this example show that various antibodies have been generaled ranging from antibodies which completely inhibit the ligand TNF-α from binding to antibodies that do not inhibit ligand blocking at all. This is true for both human antibodies and murine surrogates.

Example 4—In Vitro Functionality of Antibodies (See Also FIGS. 8-10 and the Above Description of these Figures.)

TNF-α Non-Blocking TNFR2 Antibodies Enhance Cytokine Stimulated NK Cells IFN-γ Production, in Contrast to TNF-α Blocking TNFR2 Antibodies The agonistic/antagonistic characteristics of TNFR2 specific antibodies were evaluated using a NK cell assay described by Almishri et al. (TNFα Augments Cytokine-Induced NK Cell IFNγ Production through TNFR2. Almishri W. et al. *J Innate Immun.* 2016; 8:617-629).

In brief, human NK cells were isolated from human PBMCs by MACS using "NK isolation kit" (Miltenyi). 100 μl NK cells ($1 \times 10^6$ cells/ml) were cultured with 20 ng/ml rhIL-2 (R&D systems) and 20 ng/ml rhIL-12 (R&D systems) together with 10 μg/ml TNFR2 specific antibodies, 10 μg/ml isotype control or 100 ng/ml TNF-α (R&D systems) in U-bottom plates (Corning® 96 Well TC-Treated Microplates, Sigma-Aldrich). Supernatants were collected after 24h and the amount of IFN-γ produced was assessed by MSD. As a control, anti-TNF-α antibody neutralizing TNF-α (Cat. No. AF-210-NA, R&D systems) was included. As seen in FIG. 8 D, a dose of 1 μg/ml completely neutralized soluble TNF-α and this dose also lowered the IFN-γ release.

Human non-blocking TNFR2 antibodies distinctly enhanced the IL-2 and IL-12 stimulated NK cells IFN-γ production (2-3 times more IFN-γ than isotype control) while antagonistic antibodies (here shown by complete blockers) showed antagonistic effects on NK cell IFN-γ production (FIG. 8A).

This test was considered non-representative to perform with the mouse surrogate antibodies due to lack of endogenously produced TNF-α in the murine cultures and expression of inhibitory FcγR on murine NK cells and only activating FcγR on the human counterpart. Instead, the memory T cell activation assay (induction of CD25), as well as the myeloid-derived suppressive cells' (MDSCs) suppression assay, (both described below) was used to address the agonist or antagonistic properties of the murine surrogate antibodies.

Ligand Non-Blocking, but not Blocking, TNFR2 Antibodies Induce CD25 Expression on Memory CD4$^+$ T Cells To further understand the agonistic/antagonistic characteristics of the TNFR2 antibodies, their ability of enhancing the proportion of CD25 expressing memory CD4$^+$ T cells were evaluated.

Briefly, human CD4$^+$ T cells were isolated from PBMCs by MACS using the "CD4$^+$ T cell isolation kit" from Miltenyi. CD4$^+$ T cells were cultured with 10 ng/ml rhIL-2 (R&D systems) and 10 μg/ml TNFR2 specific antibody or indicated amount of rhTNF-α (R&D systems). After 3 days the expression of 0025 on memory cells (CD45RO$^+$ cells) were analyzed by FACS (FIG. 9A).

Similarly, mouse CD4$^+$ T cells were isolated from spleen by MACS using the "CD4$^+$ T cell isolation kit" (Miltenyi) and cultured with 10 ng/ml rmIL-2 (R&D systems) and 10 μg/ml TNFR2 specific antibody or indicated amount of rmTNF-α (R&D systems). The expression of CD25 on memory cells (CD44+CD62L$^-$ cells) were analyzed by FACS after 3 days (FIG. 9B).

The percentage of CD25 expressing cells was enhanced in memory cell cultures stimulated with non-blocking TNFR2, again demonstrating an agonistic activity, in both human and mouse. However, stimulation with blocking antibodies did not increase CD25 expression in these cultures.

Ligand Non-Blocking, but not Blocking, Anti-TNFR2 mAb Reverse Myeloid-Derived Suppressive Cells' (MDSCs) Suppressive Function in T Cell/MDSC Co-Culture Assays The impact of human anti-TNFR2 mAb on MDSCs' suppressive function was assessed in T cell/MDSC co-culture assays. Briefly, MDSCs were generated by culturing MACS-isolated, human CD14$^+$ monocytes in 50% ascitic fluid isolated from cancer patients, and 50% R-10 for 3 days. MDSCs were then washed and pre-incubated with 10 μg/ml anti-TNFR2 mAb for 30 min. Without washing the cells, titrating numbers of MDSCs were co-cultured with MACS-isolated, CFSE-labelled CD3$^+$ T cells in the presence of CD3/CD28 Dynabeads®. After 72 hours, the percentage of activated CD25+ T cells was assessed by FACS. IFN-γ and IL-10 secretion was measured by MSD according to manufactures' instruction.

In contrast to blocking anti-TNFR2 mAb (dark grey bars), non-blocking anti-TNFR2 mAb (light grey bars) were shown to increase the percentage of activated CD25+ in the co-culture (FIG. 10A). By measuring the amount of secreted Interferon-gamma (IFN-γ) and Interleukin-10 in the supernatant, the ratio of the two cytokines was used to estimate the Th1/Th2 balance. As demonstrated in FIG. 10B, the ratio of IFN-γ to IL-10 was significantly elevated by non-blocking anti-TNFR2 antibodies compared to blocking, antagonistic antibodies indicating that non-blocking antibodies induce a shift towards the Th1 pathway.

As for the human antibodies, the effect of mouse anti-TNFR2 antibodies has been tested in a similar suppression assay. CD11b+ myeloid cells were here directly MACS-isolated from CT26 mouse tumors and pre-incubated for 30 min with anti-TNFR2 mAb. CD3+ responder T cells were purified from naïve Balb/C spleens. Myeloid suppressor cells and CFSE-labelled T cells were co-cultured in different ratios for 3 days. The percent of proliferating CFSE$^{low}$ T cells was determined by FACS. Similar to the results for the human assays, the percentage of proliferating responder cells is significantly lower after incubation with blocking than with non-blocking antibodies (FIG. 10C).

In the MDCS suppression cultures, the myeloid cells express high levels of various FcγRs. To test if the observed agonistic and antagonistic effects are Fc dependent, the ligand non-blocking agonistic antibody 1F02 was tested in several formats, the hIgG1, binding good to activatory FcγRs, the hIgG2, binding good to also the inhibitory FcγRIIB and an Fc defective format with severely diminished binding to all FcγRs. The results in FIG. 10 D show that the agonistic activity of the non-blocking 1-F02 antibody is independent of antibody isotype and FcγR binding.

In summary, the data in example 4 show that ligand non-blocking antibodies are agonistic as measured by several methods in vitro: NK cell mediated IFN-γ release, activation of CD4+ memory cells as measured by CD25 expression and T cell proliferation and CD25 expression in an MDCS co-culture assay. Furthermore, the data shows that this is an intrinsic characteristic independent of presence of ligand and also independent of antibody isotype. We also show that the surrogate murine antibody 5A05, have similar characteristics of agonism. T cell or NK cell stimulating antibodies, could be used in treatment of cancer and could induce an endogenous immune response ultimately destroying the malignant cells.

The agonistic ligand non-blocking antibodies are shown according to the invention while the antagonistic ligand blocking antibodies are included for comparison.

Example 5—Surrogate Ligand Non-Blocking, Agonistic Anti-Mouse TNFR2 mAb has In Vivo Anti-Tumor Effect (See Also FIGS. 11-17 and the Above Description of these Figures)
Therapeutic Effect in Different Tumor Models To assess the in vivo anti-tumor effect of ligand non-blocking, agonistic anti-TNFR2 mAbs a mouse surrogate, called 5-A05, was investigated in vivo in different tumor models, using different isotype formats, and alone or in combination with anti-PD-1 as described below.

Mice were bred and maintained in local facilities in accordance with home office guidelines. Six to eight weeks-old female BalbC and C57/BL6 mice were supplied by Taconic (Bomholt, Denmark) and maintained in local animal facilities. CT26, MC38 and B16 cells (ATCC) were grown in glutamax buffered RPMI, supplemented with 10% FCS. When cells were semi confluent, they were detached with trypsin and resuspended in sterile PBS at 10×106 cells/ml. Mice were s.c. injected with 100 μl cell suspension corresponding to 1×106 cells/mouse. 3-8 days after injection dependent on model, mice were treated twice weekly with 10 mg/kg antibody i.p. (isotype control, 3-F10 or 5-A05) and as indicated in figures. Tumors were measured two times/week until they reached a diameter of 15 mm, where after the mice were terminated The ligand non-blocking, agonistic anti-mouse TNFR2 mAb 5-A05 show therapeutic anti-tumor effect in three different tumor models (FIG. 11-14), with curative effect in more treatment sensitive CT26 (FIG. 11) and tumor growth inhibiting effect in more treatment resistant MC38 and B16 (FIG. 12-14).

The Anti-Tumor Effect of Ligand Non-Blocking, Agonistic Anti-Mouse TNFR2 mAb does not Require FcγR Binding but is Enhanced by Such Binding To assess the importance of Fc-FcγR interaction on the in vivo anti-tumor effect of the ligand non-blocking, agonistic anti-TNFR2 mouse surrogate mAb 5A05, different Fc formats of this antibody was investigated in vivo in the CT26 tumor model as described below.

Mice were bred and maintained as described above. CT26 cells (ATCC) were grown and injected as described above. When tumors reached 3×3 mm, mice were treated twice weekly with 10 mg/kg antibody i.p. (isotype control, 5A05 IgG1, 5A05 IgG2a or 5-A05-N297A (Fc defective). Tumors were measured two times/week until they reached a diameter of 15 mm, where after the mice were terminated.

The Fc-defective 5-A05-N297A shows clear therapeutic activity compared to isotype control indicating that Fc-engagement is not totally obligate to the therapeutic efficacy of this ligand non-blocking, agonistic anti-mouse TNFR2 mAb (FIGS. 11 A and B). In addition, both IgG1 and IgG2a formats show enhanced therapeutic efficacy. However, the IgG1 format preferentially binding to inhibiting Fcγ-receptors shows superior therapeutic effect indicative of agonism being one important mechanism of action of this anti-mouse TNFR2 mAb (FIG. 11 A-B). This is in contrast to a ligand blocking, antagonistic surrogate antibody 3-F10 which shows no activity in the Fc defective format and shows best activity in the murine IgG2a format, known to preferentially bind the activatory FcγR.

The ligand non-blocking agonistic antibody (5-A05) is in accordance with the invention and the ligand blocking antagonistic antibody (3-F10) is included for reference.
Combinational Effect with Anti-PD-1 mAb To assess the combinational in vivo anti-tumor effect of ligand non-blocking, agonistic anti-TNFR2 mAbs a mouse surrogate (5-A05) with anti-PD-1, the treatment combination was investigated in vivo in the MC38 tumor model as described below.

Mice were bred and maintained as described above. M038 cells (ATCC) were grown and injected as described above, Eight days after injection, mice were treated twice weekly with 10 mg/kg antibody i.p. (isotype control, anti-mouse PD-1, 5-A05 or a combination of anti-mouse PD-1 and 5-A05) and as indicated in FIG. 12 A-E. Tumors were measured two times/week until they reached a diameter of 15 mm, where after the mice were terminated.

The anti-mouse PD-1 and the ligand non-blocking, agonistic anti-mouse TNFR2 mAb 5-A05 both show tumor growth inhibiting therapeutic effect in effect in the MC38 model (FIG. 12 A-E). When the anti-PD1 and 5-A05 are combined, tumors are cured in the treatment resistant MC38 model (FIG. 12 D-E).

Combinational Effect with Anti-PD-L1 mAb

To assess the combinational in vivo anti-tumor effect of agonistic anti-TNFR2 mAbs, we further combined the mouse surrogate (5A05) with anti-PD-L1 for treatment in the MC38 tumor model as described below.

Mice were bred and maintained as described above. MC38 cells (obtained from Dr M. Cragg, Southampton University) were grown and injected as described above. Six days after injection, mice were treated twice with isotype control antibody or 3F10 (day 1 and 4), or four consecutive days with anti-PD-L1 (clone 10F.9G2, Bioxcell) followed by a fifth injection two days later (in total five injections day 1,2,3,4 and 7), or a combination of both. All antibodies were administered at 10 mg/kg i.p. Tumors were measured with calipers twice weekly until they reached a volume of 2000 mm3, where after the mice were terminated.

The anti-mouse PD-L1 and the agonistic anti-mouse TNFR2 mAb 5A05 both show tumor growth inhibiting therapeutic effect in effect in the MC38 model (FIG. 13). When the anti-PD-L1 and the antagonistic anti-mouse TNFR2 mAb 5A05 are combined, the anti-tumor effect is even further enhanced (FIG. 13).

Immune Cell Modulation In Vivo

To investigate the effects in immune cell in the tumor in vivo, BalbC mice were inoculated with CT26 cells as described above. After the tumors reached approximately 7×7 mm, the mice were treated with 10 mg/kg antibodies administered i.p. as indicated in FIG. 15. Mice were treated at day 1, 4 and 7 and terminated at day 8. Tumors were dissected out, mechanically divided into small pieces and digested using a mixture of Collagenase 100 µg/ml liberase and 100 µg/ml Dnase in 37° C. for 2×5 min with Vortex in between. After filtration through a 70 µm filter, the cell suspension was washed (400 g for 10 min) with PBS containing 10% FBS. Thereafter, the cells were resuspended in MACS buffer and stained with an antibody panel staining CD45, CD3, CD8, CD4 and CD25 or an antibody panel staining MHCII, F4/80, Ly6C, CD1b and Ly6G. Before staining, the cells were blocked for unspecific binding using 100 µg/ml IVIG (purified intravenous immunoglobulins). Cells were analyzed in a FACS Verse. Mouse Tregs were quantified as being $CD45^+CD3^+CD4^+CD25^+$ and TAMs as being $CD11b^+Ly6G^-Ly6C^-F4/80^+MHCII^+$.

As seen in FIG. 15, treatment with the agonistic TNFR2 antibody results in an increase in $CD8^+$ T cell influx in the tumor. A weaker tendency towards T reg depletion is also seen. Together, this results in a much improved $CD8^+$ T cell to T reg ratio (FIG. 15 C). In addition, the agonistic antibody modulates the myeloid compartment by reducing the number of tumor associated macrophages.

PBMC-NOG/SCID Model

To confirm the in vitro findings of agonistic/T-cell proliferative activity of the non-ligand blocking, agonistic anti-TNFR2 mAb 1-F02, we analyzed the capacity of this mAb to induce proliferation of T-cells the PBMC-NOG model in vivo as described below.

Mice were bred and maintained in local facilities in accordance with home office guidelines, Eight weeks-old female NOG mice were supplied by Taconic (Bomholt, Denmark) and maintained in local animal facilities. For the PBMC-NOG (primary human xenograft) model, human PBMCs were isolated using Ficoll Paque PLUS and after washing the cells were resuspended in sterile PBS at $75\times10^6$ cells/ml. NOG mice were i.v. injected with 200 µl cell suspension corresponding to $15\times10^6$ cells/mouse. Two weeks after injection, the mice were treated twice (two days apart) with 10 mg/kg of either isotype control, Yervoy, anti-CD25, Campath, 1-F02 or 1-H10 (ligand blocking antagonistic anti-TNFR2 mAb). The spleens of the mice were collected 2 days after the last injection. Human T cell subsets were identified and quantified by FACS using following markers: CD45, CD3, CD4, CD8, CD25, CD127 (all from BD Biosciences). In a separate experiment, spleens from untreated human PBMC were sacrificed to determine the expression of TNFR2 on human T cells by FACS (FIG. 16). This FACS data showed that the TNFR2 expression on Tregs and CD8+T cells are very comparable between the human T cells grown and activated in vivo in the NOG mice, and T cells from human tumors 1-F02 induced proliferation of T-cells in accordance with what has been seen in vitro and in vivo with the non-ligand blocking, agonistic anti-mouse surrogate TNFR2 mAb while the antagonistic 1-H10 did not induce proliferation (FIG. 17).

In summary, example 5 shows that:
1, Agonistic ligand non-blocking antibodies can have strong anti-tumor effects across several tumor models
2, This effect can be increased by combining with anti-PD1 antibodies
3, Agonistic non-ligand blocking antibodies do not show obligate FcγR dependency for anti-tumor effect, but the effect is enhanced by engagement of, primarily inhibitory, FcγRs
4. Agonistic non-ligand blocking antibodies increase CD8 positive T-cell influx and decrease Treg numbers in tumors. In addition, they decrease TAM numbers in tumors, thus altering both T-cell and myeloid cell composition in the tumor.
5. In human tumors, T cells express TNFR2
6. In a human xenograft model where tumor TNFR2 expression is mimicked on T cells, agonistic ligand non-blocking antibody 1-F02 increase the number of T cells.

Example 6—Agonistic Ligand Non-Blocking Antibodies do not Induce Large Amounts of Proinflammatory Cytokines (See Also FIGS. 18-19 and the Above Description of these Figures.)

Release of large amounts of pro-inflammatory cytokines is one possible side effect of immune modulatory antibodies used for treatment of patients. Hence, we here measured cytokine release induced by agonistic, ligand non-blocking antibodies using two different methods. The first is based on antibody stimulation in in vitro cultures, and the second is based on xenografting human immune cells to immune deficient mice. For in vitro, the set-up of the culture has been shown to largely impact the release of cytokines (Vessillier et al., J Immunol Methods. 2015 September; 424: 43-52). To account for differences in methodologies, three different in vitro culture set-ups were used in accordance with recent publications.

For the High Density Cell Culture (HDC) Cytokine Release Assays (CRA), PBMCs were cultured at $1\times10^7$ cells/ml in serum-free CTL-Test medium (Cell Technology Limited) supplemented with 2 mM glutamine, 1 mM pyruvate, 100 IU/ml of penicillin and streptomycin. 2 ml of cell culture was plated in a 12-well plate. After 48 h, 10 µg/ml antibody was added to 1×10⁵ pre-incubated PBMCs in a 96-well flat-bottom plate and incubated for 24 h.

The PBMC Solid Phase (SP) CRA was performed by coating wells of a 96-well plate with 1 μg/ml antibody for 1 h. After washing of the plate with PBS, 1×10⁵ PBMCs in 200 μl complete medium were added per well and incubated for 48 h.

The cytokine release was also measured after stimulation of 200 μl of whole blood with 5 μg/ml of antibody for 48 h.

At the end of the incubation period, plates were centrifuged, and the culture supernatant was taken and stored at −20° C. Concentrations of IFN-γ, IL-2, IL-4, IL-6, IL-10, IL-8 and TNF-α were measured using custom made MSD plates, according to the manufacturer's instructions (Meso Scale Discovery, USA).

In summary, the ligand non-blocking agonistic antibodies only induced any significant cytokine release beyond IFN-γ in any of the in vitro settings (data not shown). The positive control antibodies, Alemtuzumab and OKT3 did induce cytokines, most pronounced of all was IFN-γ. As seen in FIG. 18, the non-blocking agonistic antibodies did not induce IFN-γ in two out of three in vitro settings; furthermore, the antibody 1-F02 did not induce IFN-γ in any of the in vitro settings.

PBMC-NOG Tolerability Model

To investigate the tolerability of the ligand non-blocking, agonistic anti-human TNFR2 mAb 1-F02, we analyzed the in vivo cytokine release in the PBMC-NOG model as described below.

Mice were bred and maintained in local facilities in accordance with home office guidelines. Eight weeks-old female NOG mice were supplied by Taconic (Bomholt, Denmark) and maintained in local animal facilities. For the PBMC-NOG (primary human xenograft) model, human PBMCs were isolated using Ficoll Paque PLUS and after washing the cells were re-suspended in sterile PBS at 125×10⁶ cells/ml. NOG mice were i.v. injected with 200 μl cell suspension corresponding to 25×10⁶ cells/mouse. 2 weeks after injection, blood samples were taken to analyze the level of "humanization" meaning the amount of human cells in the blood of the NOG mice. When the blood was composed of approx. 40% human T-cells, the mice were considered humanized. The mice were then treated with 10 μg of either Yervoy, anti-CD3 (OKT-3), 1-F02, or isotype control mAb. Body temperature was measured prior to antibody injection and at 1 h post injection (FIG. 19 A). As seen in FIG. 19 A, the positive control antibody OKT3 induced dramatic lowering of body temperature as previously published, and in accordance with the toxicity seen in the clinic with this antibody. In contrast, 1-F02 did not show any effect on body temperature. Five hours post injection of antibodies the experiments were terminated, and blood was collected for analysis of cytokine release (MSD). The cytokines measured were human IFN-γ, TNF-α, IL-6 and IL1β. Of these, IFN-γ and TNF-α, were quantified in high enough levels to be reliable. As seen in FIGS. 19 B and C, the positive control antibody OKT3 induced both significant IFN-γ and TNF-α, release (in accordance with the toxicity seen in the clinic with this antibody) whereas 1-F02 treated mice had no significant IFN-γ release. However, there was a tendency towards increase in TNF-α release, although not significant and not as dramatic as for OKT3.

In summary, example 6 shows that the TNFR2 ligand non-blocking agonistic antibodies, here exemplified with the antibody called 1-F02, do not induce substantial levels of cytokine release as measured by several previously published methods. Since cytokine release is a limiting factor for several immunomodulatory antibodies, this indicates an acceptable safety profile in this regard.

Example 7—Epitopes of Generated TNFR2 Targeting Antibodies

Domain Construct Knock-Outs

In a first set of experiments, DNA constructs encoding different variants of TNFR2, missing one or more of the 4 extracellular domains, described in table 9, were used. In a second set of experiments, DNA constructs encoding variants of TNFR2 where different parts of domain 3 were exchanged with the corresponding murine part, as described in table 10, were used. The latter is possible since none of the antibodies is cross-reactive to murine TNFR. In both cases, the constructs were purchased from GeneArt (ThermoFisher). The constructs were cloned into an expression vector, containing the CMV-promotor and the OriP origin of plasmid replication, and transiently expressed in suspension adapted HEK293-EBNA cells.

TABLE 9

TNFR2 constructs used for transfection where one or several domains have been deleted.

| Construct | Description |
| --- | --- |
| hTNFR2 | wild type, full length human TNFR2 (uniprot #P20333) |
| hTNFR2-Δ1 | hTNFR2 with domain TNFR-Cys 1 (aa 39-76) deleted |
| hTNFR2-Δ2 | hTNFR2 with domain TNFR-Cys 2 (aa 77-118) deleted |
| hTNFR2-Δ3 | hTNFR2 with domain TNFR-Cys 3 (aa 119-162) deleted |
| hTNFR2-Δ4 | hTNFR2 with domain TNFR-Cys 4 (aa 163-201) deleted |
| hTNFR2-Δ1 + 3 | hTNFR2 with domain TNFR-Cys 1 and 3 (aa 39-76 and 119-162) deleted |
| hTNFR2-Δ2 + 4 | hTNFR2 with domain TNFR-Cys 2 and 4 (aa 77-118 and 163-201) deleted |

TABLE 10

TNFR2 constructs used for transfection various parts of domain 3 have been exchanged for the corresponding murine sequence.

| Construct | Description |
| --- | --- |
| hTNFR2 | wild type, full length human TNFR2 (uniprot #P20333) |
| mTNFR2 | wild type, full length murine TNFR2 (uniprot #P25119) |
| hTNFR2-m1 | hTNFR2 with aa 119-132 replaced by aa 120-133 from mTNFR2 |
| hTNFR2-m2 | hTNFR2 with aa 134-144 replaced by aa 135-146 from mTNFR2 |
| hTNFR2-m3 | hTNFR2 with aa 151-160 replaced by aa 153-162 from mTNFR2 |
| hTNFR2-m4 | hTNFR2 with aa 130-144 replaced by aa 131-146 from mTNFR2 |

Flow Cytometry Based Binding Analysis

HEK-293-E cells were transfected with the respective cDNA plasmids of TNFR2 variants using Lipofectamin 2000. 48h after transfection, cells were harvested and stained with the indicated antibodies for 30 minutes. After 2 washing steps with PBS, surface bound antibodies were stained with a secondary anti-IgG coupled to APC. Prior to flow cytometry analysis on BD-Verse flow cytometer, cells were washed and stained for live/dead.

Flow cytometry based binding experiments of transfected HEK 293 cells clearly showed, that domain 1 and domain 2 either does not affect the binding (domain 1), or only marginally affects binding (domain 2), of any of the antibodies to these cells. As a positive control a polyclonal anti-human TNFR2 antibody was used. The positive control antibody showed high binding to all tested constructs, whereas the negative antibody showed no binding (FIG. 20). All tested antibodies showed a complete loss of binding to TNFR2 lacking domain 3. Similarly, most antibodies could not bind to TNFR2 if domain 4 was missing. All antagonistic antibodies (1H10, 4H02 and 5B08) showed drastically reduced binding to TNFR2 Δ4 of more than 50% compared to binding to TNFR2 Δ1 and TNFR2 Δ2. Similarly, removing two domains from TNFR2 clearly showed that the lack of domain 3 or 4 severely abrogated binding of all tested antibodies to TNFR2, with the possible exception of agonistic antibody 1F06, while the lack of domain 4 abolished binding of agonistic antibodies and reduced the binding of the antagonistic antibodies significantly. (FIGS. 20 E and F).

Binding to Mouse-Human Chimeric TNFR2

To further narrow down the binding site and define the epitopes, parts of the human TNFR2 domain 3 were replaced by the corresponding mouse sequence, Since all antibodies shows very little cross-reactivity to mouse TNFR2, a loss of binding to certain constructs would allow refining the binding epitope. FIG. 21 displays the different mouse-human chimeric TNFR2 constructs. Four different replacements were made, exchanging either 14 (m1), 12 (m2), 10 (m3) or 16 (m4) amino acids from the human sequence with the corresponding mouse sequence. The other three domains (1, 2, 4) contain exclusively human sequences.

These constructs (TNFR2 domains 1~4 with mutations in 3) were then transfected into HEK293 cells and antibodies were tested for binding using a flow cytometry approach. As positive controls, polyclonal antibodies against mouse TNFR2 as well as against human TNFR2 were used. As expected, due to sequence similarity, both polyclonal control antibodies showed significant cross-reactivity and recognized both, human and mouse TNFR2. Obviously, best signals were achieved when matching the antibodies to its intended target.

Our monoclonal antibodies showed strong binding to human TNFR2, but no or only very little binding to mouse TNFR2 (FIG. 22 left panels). Similar binding with very little reduction was observed for all clones to the hTNFR2 m1 construct with mutations in aa 119-132, indicating, that none of the antibodies bind to an epitope within that region. However, mutations in aa 134-144 (hTNFR2 m2 construct) abrogated binding completely for half of the tested antibodies, corresponding to the antagonistic blocking antibodies 1-H10, 4-H02 and 5-B08, indicating that the antibodies bind at least partially within this region. The 1-G10 is a partial blocker also strongly affected by this replacement. Noteworthy, the agonistic antibodies (1-F02, 1-F06 and 4-E08) retained binding using construct 2, strongly suggesting a different epitope compared to the antagonistic antibodies. Interestingly, all antibodies lost binding to the hTNFR2 m3 construct with mutations in aa 151-160. This indicates, that all antibodies, both agonists and antagonists, have a partial epitope within that a sequence. Testing a slightly larger construct hTNFR2 m4 with mutations in aa 130-144 showed similar binding as with construct hTNFR2 m2.

Conclusions Binding Epitopes

Grouping the antibodies into their functionally role, the agonistic antibodies (1-F02, 1-F06 and 4-E08), seems to bind a very distal C-terminal part of domain 3 encompassing aa 151-160 and likely extend to a larger part of domain 4, whereas the epitope for the antagonists (1-H10, 5-B08 and 4-H02) are shifted more towards the center of domain 3, encompassing aa 134-160 and probably covers a smaller part of domain 4. However, despite this, their epitopes seem to overlap to some extent.

None of the antibodies bind to the N-terminal part of domain 3, aa 119-134. Binding sites to domain 4 is quite likely for all antibodies, but has not been identified completely.

The invention claimed is:

1. An agonistic antibody molecule that specifically binds to TNFR2 on a target cell, wherein the antibody molecule does not block TNF-α ligand binding to TNFR2, and where said agonistic antibody comprises VH-CDR1 of SEQ ID NO: 1, VH-CDR2 of SEQ ID NO: 2, VH-CDR3 of SEQ ID NO: 3, VL-CDR1 of SEQ ID NO: 4, VL-CDR2 of SEQ ID NO: 5, and VL-CDR3 of SEQ ID NO: 6.

2. An antibody molecule according to claim 1, wherein the antibody molecule has intrinsic agonistic activity.

3. An antibody molecule according to claim 1, wherein the antibody molecule also binds to an Fcγ receptor.

4. An antibody molecule according to claim 1, wherein the antibody molecule binds with higher affinity to inhibitory Fcγ receptors than to activating Fcγ receptors.

5. An antibody molecule according to claim 1, wherein the binding of the antibody molecule to TNFR2 results in change in numbers and/or frequency of TNFR2 expressing cells in diseased tissue.

6. An antibody molecule according to claim 1, wherein the binding of the antibody molecule to TNFR2 results in infiltration of T-cells and/or myeloid cells into diseased tissue and/or a change in composition of T-cells and/or myeloid cells in diseased tissue.

7. An antibody molecule according to claim 1, wherein the antibody molecule is selected from the group consisting of: a full-size antibody, a chimeric antibody, a divalent or multivalent antibody molecule comprising single chain antibodies, Fabs, Fvs, scFvs, Fab's, and/or (Fab')₂ and an antigen-binding fragment thereof.

8. An antibody molecule according to claim 1, which binds to human TNFR2 (hTNFR2) and/or to cynomolgus monkey TNFR2 (cmTNFR2).

9. An antibody molecule according to claim 1, wherein the antibody molecule is selected from the group consisting of a human IgG antibody molecule, a humanized IgG antibody molecule, and an IgG antibody molecule of human origin.

10. An antibody molecule according to claim 9, wherein the antibody molecule is a human IgG2 antibody.

11. An antibody molecule according to claim 1, wherein the antibody molecule is a monoclonal antibody.

12. An antibody molecule according to claim 1, wherein the antibody molecule does not bind specifically to an epitope comprising or consisting of the sequence KCSPG (SEQ ID NO: 224).

13. An antibody molecule according to claim 1, wherein the antibody molecule comprises a variable heavy chain (VH) comprising SEQ ID NO: 7 and a variable light chain (VL) comprising SEQ ID NO: 8.

14. An isolated nucleotide sequence encoding an antibody molecule as defined in claim 1.

15. A plasmid comprising a nucleotide sequence as defined in claim 14.

16. A virus comprising a nucleotide sequence as defined in claim 14.

17. A virus according to claim 16, further comprising a nucleotide sequence encoding an antibody molecule that specifically binds to a check-point inhibitor.

18. A cell comprising a nucleotide sequence as defined in claim 14.

19. A method of treating a disease comprising administering to a patient an antibody molecule as defined in claim 1.

20. A method of treating cancer or a chronic inflammatory disease comprising administering to a patient an antibody molecule as defined in claim 1.

21. A method according to claim 20, wherein the patient to be treated is a patient having high TNFR2 expression in diseased tissue.

22. A method of treating cancer comprising administering to a patient an antibody molecule as defined in claim 1, wherein said antibody is administered in combination with:
   an antibody molecule that specifically binds to a check-point inhibitor;
   a nucleotide sequence encoding an antibody molecule that specifically binds to a check-point inhibitor;
   a plasmid comprising a nucleotide sequence encoding an antibody molecule that specifically binds to a check-point inhibitor; and/or
   a cell comprising a nucleotide sequence encoding an antibody molecule that specifically binds to a check-point inhibitor, a plasmid comprising a nucleotide sequence encoding an antibody molecule that specifically binds to a check-point inhibitor or a virus comprising a nucleotide sequence encoding an antibody molecule that specifically binds to a check-point inhibitor.

23. A pharmaceutical composition comprising or consisting of an antibody molecule as defined in claim 1 and further comprising a pharmaceutically acceptable diluent, carrier, vehicle and/or excipient.

24. A method of treating cancer, comprising administering a pharmaceutical composition according to claim 23 to a subject in combination with a second pharmaceutical composition comprising:
   an antibody molecule that specifically binds to a check-point inhibitor;
   a nucleotide sequence encoding an antibody molecule that specifically binds to a check-point inhibitor;
   a plasmid comprising a nucleotide sequence encoding an antibody molecule that specifically binds to a check-point inhibitor; and/or
   a cell comprising a nucleotide sequence encoding an antibody molecule that specifically binds to a check-point inhibitor, a plasmid comprising a nucleotide sequence encoding an antibody molecule that specifically binds to a check-point inhibitor or a virus comprising a nucleotide sequence encoding an antibody molecule that specifically binds to a check-point inhibitor.

25. A method according to claim 20, wherein the patient is a patient having cancer or a chronic inflammatory disease and exhibits high TNFR2 expression in diseased tissue.

26. A method for treatment of cancer according to claim 24, wherein also a therapeutically effective amount of:
   an antibody molecule that specifically binds to a check-point inhibitor;
   a nucleotide sequence encoding an antibody molecule that specifically binds to a check-point inhibitor;
   a plasmid comprising a nucleotide sequence encoding an antibody molecule that specifically binds to a check-point inhibitor; and/or
   a cell comprising a nucleotide sequence encoding an antibody molecule that specifically binds to a check-point inhibitor, a plasmid comprising a nucleotide sequence encoding an antibody molecule that specifically binds to a check-point inhibitor or a virus comprising a nucleotide sequence encoding an antibody molecule that specifically binds to a check-point inhibitor is administered to the subject.

27. A method according to claim 22, wherein the check-point inhibitor is PD-1.

28. A method according to claim 22, wherein the check-point inhibitor is PD-L1.

29. A method according to claim 20, wherein the cancer is a solid cancer.

* * * * *

UNITED STATES PATENT AND TRADEMARK OFFICE
CERTIFICATE OF CORRECTION

| | | |
|---|---|---|
| PATENT NO. | : 12,139,547 B2 | Page 1 of 1 |
| APPLICATION NO. | : 17/290340 | |
| DATED | : November 12, 2024 | |
| INVENTOR(S) | : Frendéus et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 729 days.

Signed and Sealed this
Eighth Day of April, 2025

Coke Morgan Stewart
*Acting Director of the United States Patent and Trademark Office*

SEQUENCE LISTING

```
<160> NUMBER OF SEQ ID NOS: 225

<210> SEQ ID NO 1
<211> LENGTH: 14
<212> TYPE: PRT
<213> ORGANISM: Homo sapiens

<400> SEQUENCE: 1

Phe Ser Asp Tyr Tyr Met Ser Trp Val Arg Gln Ala Pro Gly
1               5                   10

<210> SEQ ID NO 2
<211> LENGTH: 19
<212> TYPE: PRT
<213> ORGANISM: Homo sapiens

<400> SEQUENCE: 2

Ala Asn Ile Asn Thr Asp Gly Ser Glu Lys Tyr Tyr Leu Asp Ser Val
1               5                   10                  15
```

Lys Gly Arg

<210> SEQ ID NO 3
<211> LENGTH: 10
<212> TYPE: PRT
<213> ORGANISM: Homo sapiens

<400> SEQUENCE: 3

Ala Arg Glu Glu Tyr Gly Ala Phe Asp Ile
1               5                   10

<210> SEQ ID NO 4
<211> LENGTH: 14
<212> TYPE: PRT
<213> ORGANISM: Homo sapiens

<400> SEQUENCE: 4

Cys Ser Gly Ser Ser Ser Asn Ile Gly Ser Asn Thr Val Asn
1               5                   10

<210> SEQ ID NO 5
<211> LENGTH: 7
<212> TYPE: PRT
<213> ORGANISM: Homo sapiens

<400> SEQUENCE: 5

Asp Asn Asn Lys Arg Pro Ser
1               5

<210> SEQ ID NO 6
<211> LENGTH: 13
<212> TYPE: PRT
<213> ORGANISM: Homo sapiens

<400> SEQUENCE: 6

Cys Gln Ser Phe Asp Arg Gly Leu Ser Gly Ser Ile Val
1               5                   10

<210> SEQ ID NO 7
<211> LENGTH: 117
<212> TYPE: PRT
<213> ORGANISM: Homo sapiens

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ala Asn Ile Asn Thr Asp Gly Ser Glu Lys Tyr Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Tyr Gly Ala Phe Asp Ile Trp Gly Gln Gly Thr Leu
            100                 105                 110

Val Thr Val Ser Ser
        115

```
<210> SEQ ID NO 8
<211> LENGTH: 112
<212> TYPE: PRT
<213> ORGANISM: Homo sapiens

<400> SEQUENCE: 8

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Phe Asp Arg Gly Leu
                85                  90                  95

Ser Gly Ser Ile Val Phe Gly Gly Thr Lys Leu Thr Val Leu Gly
            100                 105                 110

<210> SEQ ID NO 9
<211> LENGTH: 14
<212> TYPE: PRT
<213> ORGANISM: Homo sapiens

<400> SEQUENCE: 9

Phe Ser Ser Tyr Ala Met His Trp Val Arg Gln Ala Pro Gly
1               5                   10

<210> SEQ ID NO 10
<211> LENGTH: 19
<212> TYPE: PRT
<213> ORGANISM: Homo sapiens

<400> SEQUENCE: 10

Ser Ala Ile Ser Gly Gly Ala Thr Thr Thr Tyr Tyr Ala Asp Ser Val
1               5                   10                  15

Lys Gly Arg

<210> SEQ ID NO 11
<211> LENGTH: 13
<212> TYPE: PRT
<213> ORGANISM: Homo sapiens

<400> SEQUENCE: 11

Ala Lys Gly Gly Thr Gly Asp Pro Tyr Tyr Phe Asp Tyr
1               5                   10

<210> SEQ ID NO 12
<211> LENGTH: 15
<212> TYPE: PRT
<213> ORGANISM: Homo sapiens

<400> SEQUENCE: 12

Cys Thr Gly Ser Ser Ser Asn Ile Gly Ala Gly Tyr Asp Val His
1               5                   10                  15

<210> SEQ ID NO 13
<211> LENGTH: 7
<212> TYPE: PRT
<213> ORGANISM: Homo sapiens
```

<400> SEQUENCE: 13

Arg Asn Asn Gln Arg Pro Ser
1               5

<210> SEQ ID NO 14
<211> LENGTH: 12
<212> TYPE: PRT
<213> ORGANISM: Homo sapiens

<400> SEQUENCE: 14

Cys Ala Ala Arg Asp Asp Gly Leu Ser Gly Pro Val
1               5                   10

<210> SEQ ID NO 15
<211> LENGTH: 120
<212> TYPE: PRT
<213> ORGANISM: Homo sapiens

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Gly Gly Ala Thr Thr Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Thr Gly Asp Pro Tyr Tyr Phe Asp Tyr Trp Gly Gln
            100                 105                 110

Gly Thr Leu Val Thr Val Ser Ser
        115                 120

<210> SEQ ID NO 16
<211> LENGTH: 112
<212> TYPE: PRT
<213> ORGANISM: Homo sapiens

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Arg Asp Asp Gly
                85                  90                  95

Leu Ser Gly Pro Val Phe Gly Gly Gly Thr Lys Leu Thr Val Leu Gly
            100                 105                 110

```
<210> SEQ ID NO 17
<211> LENGTH: 14
<212> TYPE: PRT
<213> ORGANISM: Homo sapiens

<400> SEQUENCE: 17

Phe Ser Asn Ala Trp Met Ser Trp Val Arg Gln Ala Pro Gly
1               5                   10

<210> SEQ ID NO 18
<211> LENGTH: 19
<212> TYPE: PRT
<213> ORGANISM: Homo sapiens

<400> SEQUENCE: 18

Ser Ser Ile Ser Ser Ala Ser Gly Tyr Ile Tyr Tyr Gly Asp Ser Val
1               5                   10                  15

Lys Gly Arg

<210> SEQ ID NO 19
<211> LENGTH: 12
<212> TYPE: PRT
<213> ORGANISM: Homo sapiens

<400> SEQUENCE: 19

Ala Arg Gly Thr Leu Tyr Gly Asp Phe Asp Glu Phe
1               5                   10

<210> SEQ ID NO 20
<211> LENGTH: 14
<212> TYPE: PRT
<213> ORGANISM: Homo sapiens

<400> SEQUENCE: 20

Cys Ser Gly Ser Ser Asn Ile Gly Asn Asn Ala Val Asn
1               5                   10

<210> SEQ ID NO 21
<211> LENGTH: 7
<212> TYPE: PRT
<213> ORGANISM: Homo sapiens

<400> SEQUENCE: 21

Gly Asn Thr Asn Arg Pro Ser
1               5

<210> SEQ ID NO 22
<211> LENGTH: 13
<212> TYPE: PRT
<213> ORGANISM: Homo sapiens

<400> SEQUENCE: 22

Cys Gln Ser Tyr Asp Ser Ser Leu Ser Gly Tyr Val Val
1               5                   10

<210> SEQ ID NO 23
<211> LENGTH: 119
<212> TYPE: PRT
<213> ORGANISM: Homo sapiens

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
```

```
                  20                  25                  30

Trp Met Ser Trp Val Arg Gln Ala Pro Gly Lys Gly Leu Glu Trp Val
        35                  40                  45

Ser Ser Ile Ser Ala Ser Gly Tyr Ile Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Arg Gly Thr Leu Tyr Gly Asp Phe Asp Glu Phe Trp Gln Gly
            100                 105                 110

Thr Leu Val Thr Val Ser Ser
            115

<210> SEQ ID NO 24
<211> LENGTH: 112
<212> TYPE: PRT
<213> ORGANISM: Homo sapiens

<400> SEQUENCE: 24

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
                20                  25                  30

Ala Val Asn Trp Tyr Gln Gln Leu Pro Gly Thr Ala Pro Lys Leu Leu
            35                  40                  45

Ile Tyr Gly Asn Thr Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Tyr Val Val Phe Gly Gly Gly Thr Lys Leu Thr Val Leu Gly
            100                 105                 110

<210> SEQ ID NO 25
<211> LENGTH: 14
<212> TYPE: PRT
<213> ORGANISM: Homo sapiens

<400> SEQUENCE: 25

Phe Ser Ser Asn Glu Met Ser Trp Ile Arg Gln Ala Pro Gly
1               5                   10

<210> SEQ ID NO 26
<211> LENGTH: 18
<212> TYPE: PRT
<213> ORGANISM: Homo sapiens

<400> SEQUENCE: 26

Ser Val Ile Tyr Ser Gly Gly Ser Thr Tyr Tyr Ala Asp Ser Val Lys
1               5                   10                  15

Gly Arg

<210> SEQ ID NO 27
<211> LENGTH: 12
<212> TYPE: PRT
<213> ORGANISM: Homo sapiens
```

```
<400> SEQUENCE: 27

Ala Arg Arg Glu Gly Trp Leu Val Pro Phe Asp Tyr
1               5                   10

<210> SEQ ID NO 28
<211> LENGTH: 14
<212> TYPE: PRT
<213> ORGANISM: Homo sapiens

<400> SEQUENCE: 28

Cys Ser Gly Ser Ser Ser Asn Ile Gly Ser Asn Thr Val Asn
1               5                   10

<210> SEQ ID NO 29
<211> LENGTH: 7
<212> TYPE: PRT
<213> ORGANISM: Homo sapiens

<400> SEQUENCE: 29

Gly Asn Ile Ile Arg Pro Ser
1               5

<210> SEQ ID NO 30
<211> LENGTH: 13
<212> TYPE: PRT
<213> ORGANISM: Homo sapiens

<400> SEQUENCE: 30

Cys Gln Ser Phe Asp Thr Thr Leu Ser Gly Ser Ile Val
1               5                   10

<210> SEQ ID NO 31
<211> LENGTH: 118
<212> TYPE: PRT
<213> ORGANISM: Homo sapiens

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Glu Met Ser Trp Ile Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Glu Gly Trp Leu Val Pro Phe Asp Tyr Trp Gly Gln Gly Thr
            100                 105                 110

Leu Val Thr Val Ser Ser
        115

<210> SEQ ID NO 32
<211> LENGTH: 112
<212> TYPE: PRT
<213> ORGANISM: Homo sapiens

<400> SEQUENCE: 32

Gln Ser Val Leu Thr Gln Pro Pro Ser Ala Ser Gly Thr Pro Gly Gln
```

-continued

```
                1               5                  10                  15
            Arg Val Thr Ile Ser Cys Ser Gly Ser Ser Asn Ile Gly Ser Asn
                               20                  25                  30

Thr Val Asn Trp Tyr Gln Gln Leu Pro Gly Thr Ala Pro Lys Leu Leu
                       35                  40                  45

Ile Tyr Gly Asn Ile Ile Arg Pro Ser Gly Val Pro Asp Arg Phe Ser
                   50                  55                  60

Gly Ser Lys Ser Gly Thr Ser Ala Ser Leu Ala Ile Ser Gly Leu Arg
             65                  70                  75                  80

Ser Glu Asp Glu Ala Asp Tyr Tyr Cys Gln Ser Phe Asp Thr Thr Leu
                               85                  90                  95

Ser Gly Ser Ile Val Phe Gly Gly Thr Lys Leu Thr Val Leu Gly
                       100                 105                 110
```

<210> SEQ ID NO 33
<211> LENGTH: 14
<212> TYPE: PRT
<213> ORGANISM: Homo sapiens

<400> SEQUENCE: 33

```
Phe Ser Arg Tyr Trp Met His Trp Val Arg Gln Val Pro Gly
1               5                  10
```

<210> SEQ ID NO 34
<211> LENGTH: 19
<212> TYPE: PRT
<213> ORGANISM: Homo sapiens

<400> SEQUENCE: 34

```
Ser Gly Ile Ser Asp Ser Gly Val Val Thr Tyr Tyr Ala Asp Ser Val
1               5                  10                  15

Lys Gly Arg
```

<210> SEQ ID NO 35
<211> LENGTH: 10
<212> TYPE: PRT
<213> ORGANISM: Homo sapiens

<400> SEQUENCE: 35

```
Ala Arg Ala Gln Ser Val Ala Phe Asp Ile
1               5                  10
```

<210> SEQ ID NO 36
<211> LENGTH: 15
<212> TYPE: PRT
<213> ORGANISM: Homo sapiens

<400> SEQUENCE: 36

```
Cys Ser Gly Ser Ser Ser Asn Ile Gly Ala Gly His Asp Val His
1               5                  10                  15
```

<210> SEQ ID NO 37
<211> LENGTH: 7
<212> TYPE: PRT
<213> ORGANISM: Homo sapiens

<400> SEQUENCE: 37

```
Tyr Asp Asp Leu Leu Pro Ser
1               5
```

<210> SEQ ID NO 38

<211> LENGTH: 12
<212> TYPE: PRT
<213> ORGANISM: Homo sapiens

<400> SEQUENCE: 38

Cys Ala Ala Trp Asp Asp Ser Leu Ser Gly Trp Val
1               5                   10

<210> SEQ ID NO 39
<211> LENGTH: 117
<212> TYPE: PRT
<213> ORGANISM: Homo sapiens

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
                20                  25                  30

Trp Met His Trp Val Arg Gln Val Pro Gly Lys Gly Leu Glu Trp Val
            35                  40                  45

Ser Gly Ile Ser Asp Ser Gly Val Val Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gln Ser Val Ala Phe Asp Ile Trp Gly Gln Gly Thr Leu
            100                 105                 110

Val Thr Val Ser Ser
        115

<210> SEQ ID NO 40
<211> LENGTH: 112
<212> TYPE: PRT
<213> ORGANISM: Homo sapiens

<400> SEQUENCE: 40

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ala Gly
                20                  25                  30

His Asp Val His Trp Tyr Gln Gln Leu Pro Gly Thr Ala Pro Lys Leu
            35                  40                  45

Leu Ile Tyr Tyr Asp Asp Leu Leu Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Gly Trp Val Phe Gly Gly Gly Thr Lys Leu Thr Val Leu Gly
            100                 105                 110

<210> SEQ ID NO 41
<211> LENGTH: 14
<212> TYPE: PRT
<213> ORGANISM: Homo sapiens

<400> SEQUENCE: 41

Phe Ser Ser Tyr Ala Met Ser Trp Val Arg Gln Ala Pro Gly

```
                1               5                   10
```

<210> SEQ ID NO 42
<211> LENGTH: 19
<212> TYPE: PRT
<213> ORGANISM: Homo sapiens

<400> SEQUENCE: 42

```
Ser Val Ile Ser Gly Ser Gly Gly Ser Thr Tyr Tyr Ala Asp Ala Val
1               5                   10                  15

Lys Gly Arg
```

<210> SEQ ID NO 43
<211> LENGTH: 10
<212> TYPE: PRT
<213> ORGANISM: Homo sapiens

<400> SEQUENCE: 43

```
Thr Thr Asp Ser Gly Ser Gly Ser Tyr Leu
1               5                   10
```

<210> SEQ ID NO 44
<211> LENGTH: 15
<212> TYPE: PRT
<213> ORGANISM: Homo sapiens

<400> SEQUENCE: 44

```
Cys Thr Gly Ser Ser Ser Asn Ile Gly Ala Gly Tyr Asp Val His
1               5                   10                  15
```

<210> SEQ ID NO 45
<211> LENGTH: 7
<212> TYPE: PRT
<213> ORGANISM: Homo sapiens

<400> SEQUENCE: 45

```
Ser Asn Asn Gln Arg Pro Ser
1               5
```

<210> SEQ ID NO 46
<211> LENGTH: 12
<212> TYPE: PRT
<213> ORGANISM: Homo sapiens

<400> SEQUENCE: 46

```
Cys Ala Ala Trp Asp Asp Ser Leu Asn Gly Pro Val
1               5                   10
```

<210> SEQ ID NO 47
<211> LENGTH: 117
<212> TYPE: PRT
<213> ORGANISM: Homo sapiens

<400> SEQUENCE: 47

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ala Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Thr Asp Ser Gly Ser Gly Ser Tyr Leu Trp Gly Gln Gly Thr Leu
            100                 105                 110

Val Thr Val Ser Ser
            115

<210> SEQ ID NO 48
<211> LENGTH: 112
<212> TYPE: PRT
<213> ORGANISM: Homo sapiens

<400> SEQUENCE: 48

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ser Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
            85                  90                  95

Leu Asn Gly Pro Val Phe Gly Gly Gly Thr Lys Leu Thr Val Leu Gly
            100                 105                 110

<210> SEQ ID NO 49
<211> LENGTH: 14
<212> TYPE: PRT
<213> ORGANISM: Homo sapiens

<400> SEQUENCE: 49

Phe Ser Ser Asn Tyr Met Ser Trp Val Arg Gln Ala Pro Gly
1               5                   10

<210> SEQ ID NO 50
<211> LENGTH: 19
<212> TYPE: PRT
<213> ORGANISM: Homo sapiens

<400> SEQUENCE: 50

Ser Val Ile Ser Gly Ser Gly Gly Ser Thr Tyr Tyr Ala Asp Ser Val
1               5                   10                  15

Lys Gly Arg

<210> SEQ ID NO 51
<211> LENGTH: 9
<212> TYPE: PRT
<213> ORGANISM: Homo sapiens

<400> SEQUENCE: 51

Ala Arg Asp Arg Gly Trp Phe Asp Pro
1               5

<210> SEQ ID NO 52
<211> LENGTH: 14

```
<212> TYPE: PRT
<213> ORGANISM: Homo sapiens

<400> SEQUENCE: 52

Cys Ser Gly Ser Arg Ser Asn Ile Asp Asn Ser Tyr Val Ser
1               5                   10

<210> SEQ ID NO 53
<211> LENGTH: 7
<212> TYPE: PRT
<213> ORGANISM: Homo sapiens

<400> SEQUENCE: 53

Arg Asn Asn Gln Arg Pro Ser
1               5

<210> SEQ ID NO 54
<211> LENGTH: 12
<212> TYPE: PRT
<213> ORGANISM: Homo sapiens

<400> SEQUENCE: 54

Cys Ala Thr Trp Asp Asp Ser Leu Ser Gly Pro Val
1               5                   10

<210> SEQ ID NO 55
<211> LENGTH: 116
<212> TYPE: PRT
<213> ORGANISM: Homo sapiens

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Trp Phe Asp Pro Trp Gly Gln Gly Thr Leu Val
            100                 105                 110

Thr Val Ser Ser
        115

<210> SEQ ID NO 56
<211> LENGTH: 111
<212> TYPE: PRT
<213> ORGANISM: Homo sapiens

<400> SEQUENCE: 56

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Asp Asn Ser
            20                  25                  30

Tyr Val Ser Trp Tyr Gln Gln Leu Pro Gly Thr Ala Pro Lys Leu Leu
        35                  40                  45
```

```
Ile Tyr Arg Asn Asn Gln Arg Pro Ser Gly Val Pro Asp Arg Phe Ser
        50                  55                  60
Gly Ser Lys Ser Gly Thr Ser Ala Ser Leu Ala Ile Ser Gly Leu Arg
 65                  70                  75                  80
Ser Glu Asp Glu Ala Asp Tyr Tyr Cys Ala Thr Trp Asp Asp Ser Leu
                 85                  90                  95
Ser Gly Pro Val Phe Gly Gly Gly Thr Lys Leu Thr Val Leu Gly
                100                 105                 110
```

<210> SEQ ID NO 57
<211> LENGTH: 14
<212> TYPE: PRT
<213> ORGANISM: Homo sapiens

<400> SEQUENCE: 57

```
Phe Ser Arg His Ala Met Asn Trp Val Arg Gln Ala Pro Gly
 1               5                  10
```

<210> SEQ ID NO 58
<211> LENGTH: 19
<212> TYPE: PRT
<213> ORGANISM: Homo sapiens

<400> SEQUENCE: 58

```
Ser Ser Ile Ser Thr Gly Ser Ser Tyr Ile Asp Tyr Ala Asp Ser Val
 1               5                  10                  15
Lys Gly Arg
```

<210> SEQ ID NO 59
<211> LENGTH: 13
<212> TYPE: PRT
<213> ORGANISM: Homo sapiens

<400> SEQUENCE: 59

```
Ala Arg Glu Lys Gly His Tyr Tyr Tyr Gly Met Asp Val
 1               5                  10
```

<210> SEQ ID NO 60
<211> LENGTH: 15
<212> TYPE: PRT
<213> ORGANISM: Homo sapiens

<400> SEQUENCE: 60

```
Cys Thr Gly Ser Ser Ser Asn Ile Gly Ala Gly Tyr Asp Val His
 1               5                  10                  15
```

<210> SEQ ID NO 61
<211> LENGTH: 7
<212> TYPE: PRT
<213> ORGANISM: Homo sapiens

<400> SEQUENCE: 61

```
Gly Asn Ser Tyr Arg Pro Ser
 1               5
```

<210> SEQ ID NO 62
<211> LENGTH: 13
<212> TYPE: PRT
<213> ORGANISM: Homo sapiens

<400> SEQUENCE: 62

```
Cys Gln Ser Tyr Asp Thr Ser Leu Ser Ala Tyr Val Val
 1               5                  10
```

<210> SEQ ID NO 63
<211> LENGTH: 120
<212> TYPE: PRT
<213> ORGANISM: Homo sapiens

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Ala Met Asn Trp Val Arg Gln Ala Pro Gly Lys Gly Leu Glu Trp Val
        35                  40                  45

Ser Ser Ile Ser Thr Gly Ser Ser Tyr Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Gly His Tyr Tyr Tyr Gly Met Asp Val Trp Gly Gln
            100                 105                 110

Gly Thr Leu Val Thr Val Ser Ser
        115                 120

<210> SEQ ID NO 64
<211> LENGTH: 113
<212> TYPE: PRT
<213> ORGANISM: Homo sapiens

<400> SEQUENCE: 64

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Tyr Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Thr Ser
                85                  90                  95

Leu Ser Ala Tyr Val Val Phe Gly Gly Gly Thr Lys Leu Thr Val Leu
            100                 105                 110

Gly

<210> SEQ ID NO 65
<211> LENGTH: 14
<212> TYPE: PRT
<213> ORGANISM: Homo sapiens

<400> SEQUENCE: 65

Phe Ser Asn Ala Trp Met Ser Trp Val Arg Gln Ala Pro Gly
1               5                   10

<210> SEQ ID NO 66
<211> LENGTH: 19
<212> TYPE: PRT

<213> ORGANISM: Homo sapiens

<400> SEQUENCE: 66

Ser Ala Ile Ser Val Ser Gly Ile Asn Thr Tyr Tyr Ala Asp Ser Val
1               5                   10                  15

Lys Gly Arg

<210> SEQ ID NO 67
<211> LENGTH: 11
<212> TYPE: PRT
<213> ORGANISM: Homo sapiens

<400> SEQUENCE: 67

Ala Arg Asp Thr Gly Ser Leu Gly Val Asp Tyr
1               5                   10

<210> SEQ ID NO 68
<211> LENGTH: 14
<212> TYPE: PRT
<213> ORGANISM: Homo sapiens

<400> SEQUENCE: 68

Cys Ser Gly Ser Ser Asn Ile Gly Ser Asn Thr Val Asn
1               5                   10

<210> SEQ ID NO 69
<211> LENGTH: 7
<212> TYPE: PRT
<213> ORGANISM: Homo sapiens

<400> SEQUENCE: 69

Arg Asn Asn Gln Arg Pro Ser
1               5

<210> SEQ ID NO 70
<211> LENGTH: 12
<212> TYPE: PRT
<213> ORGANISM: Homo sapiens

<400> SEQUENCE: 70

Cys Gln Ser Tyr Asp Ser Ser Leu Ser Ile Ser Val
1               5                   10

<210> SEQ ID NO 71
<211> LENGTH: 118
<212> TYPE: PRT
<213> ORGANISM: Homo sapiens

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Ala Ile Ser Val Ser Gly Ile Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Arg Asp Thr Gly Ser Leu Gly Val Asp Tyr Trp Gly Gln Gly Thr
            100                 105                 110

Leu Val Thr Val Ser Ser
        115

<210> SEQ ID NO 72
<211> LENGTH: 111
<212> TYPE: PRT
<213> ORGANISM: Homo sapiens

<400> SEQUENCE: 72

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Ile Ser Val Phe Gly Gly Gly Thr Lys Leu Thr Val Leu Gly
            100                 105                 110

<210> SEQ ID NO 73
<211> LENGTH: 14
<212> TYPE: PRT
<213> ORGANISM: Homo sapiens

<400> SEQUENCE: 73

Ser Ser Ser Tyr Trp Met Ser Trp Val Arg Gln Ala Pro Gly
1               5                   10

<210> SEQ ID NO 74
<211> LENGTH: 19
<212> TYPE: PRT
<213> ORGANISM: Homo sapiens

<400> SEQUENCE: 74

Ser Ala Ile Ser Gly Ser Gly Gly Ser Thr Tyr Tyr Ala Asp Ser Val
1               5                   10                  15

Lys Gly Arg

<210> SEQ ID NO 75
<211> LENGTH: 11
<212> TYPE: PRT
<213> ORGANISM: Homo sapiens

<400> SEQUENCE: 75

Ala Arg Glu Tyr Ser Gly Tyr Glu Phe Asp Phe
1               5                   10

<210> SEQ ID NO 76
<211> LENGTH: 15
<212> TYPE: PRT
<213> ORGANISM: Homo sapiens

<400> SEQUENCE: 76

Cys Thr Gly Ser Ser Ser Asn Ile Gly Ala Arg Ser Asp Val His
```

-continued

<210> SEQ ID NO 77
<211> LENGTH: 7
<212> TYPE: PRT
<213> ORGANISM: Homo sapiens

<400> SEQUENCE: 77

Gly Asn Arg Asn Arg Pro Ser
1               5

<210> SEQ ID NO 78
<211> LENGTH: 13
<212> TYPE: PRT
<213> ORGANISM: Homo sapiens

<400> SEQUENCE: 78

Cys Gln Ser Phe Asp Arg Gly Leu Ser Gly Ser Ile Val
1               5                   10

<210> SEQ ID NO 79
<211> LENGTH: 118
<212> TYPE: PRT
<213> ORGANISM: Homo sapiens

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Ser Ser Tyr
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Tyr Ser Gly Tyr Glu Phe Asp Phe Trp Gly Gln Gly Thr
            100                 105                 110

Leu Val Thr Val Ser Ser
        115

<210> SEQ ID NO 80
<211> LENGTH: 113
<212> TYPE: PRT
<213> ORGANISM: Homo sapiens

<400> SEQUENCE: 80

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Arg
            20                  25                  30

Ser Asp Val His Trp Tyr Gln Gln Leu Pro Gly Thr Ala Pro Lys Leu
        35                  40                  45

Leu Ile Tyr Gly Asn Arg Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

-continued

```
Arg Ser Glu Asp Glu Ala Asp Tyr Tyr Cys Gln Ser Phe Asp Arg Gly
                85                  90                  95
Leu Ser Gly Ser Ile Val Phe Gly Gly Gly Thr Lys Leu Thr Val Leu
            100                 105                 110
Gly

<210> SEQ ID NO 81
<211> LENGTH: 14
<212> TYPE: PRT
<213> ORGANISM: Homo sapiens

<400> SEQUENCE: 81

Ser Ser Ser Tyr Trp Met Ser Trp Val Arg Gln Ala Pro Gly
1               5                   10

<210> SEQ ID NO 82
<211> LENGTH: 19
<212> TYPE: PRT
<213> ORGANISM: Homo sapiens

<400> SEQUENCE: 82

Ser Ala Ile Ser Gly Ser Gly Gly Ser Thr Tyr Tyr Ala Asp Ser Val
1               5                   10                  15
Lys Gly Arg

<210> SEQ ID NO 83
<211> LENGTH: 11
<212> TYPE: PRT
<213> ORGANISM: Homo sapiens

<400> SEQUENCE: 83

Ala Arg Glu Tyr Ser Gly Tyr Glu Phe Asp Phe
1               5                   10

<210> SEQ ID NO 84
<211> LENGTH: 15
<212> TYPE: PRT
<213> ORGANISM: Homo sapiens

<400> SEQUENCE: 84

Cys Thr Gly Ser Ser Ser Asn Ile Gly Ala Arg Ser Asp Val His
1               5                   10                  15

<210> SEQ ID NO 85
<211> LENGTH: 7
<212> TYPE: PRT
<213> ORGANISM: Homo sapiens

<400> SEQUENCE: 85

Gly Asn Arg Asn Arg Pro Ser
1               5

<210> SEQ ID NO 86
<211> LENGTH: 13
<212> TYPE: PRT
<213> ORGANISM: Homo sapiens

<400> SEQUENCE: 86

Cys Gln Ser Phe Asp Arg Gly Leu Ser Gly Ser Ile Val
1               5                   10

<210> SEQ ID NO 87
<211> LENGTH: 118
```

```
<212> TYPE: PRT
<213> ORGANISM: Homo sapiens

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Ser Ser Tyr
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Tyr Ser Gly Tyr Glu Phe Asp Phe Trp Gly Gln Gly Thr
            100                 105                 110

Leu Val Thr Val Ser Ser
            115

<210> SEQ ID NO 88
<211> LENGTH: 113
<212> TYPE: PRT
<213> ORGANISM: Homo sapiens

<400> SEQUENCE: 88

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Arg
            20                  25                  30

Ser Asp Val His Trp Tyr Gln Gln Leu Pro Gly Thr Ala Pro Lys Leu
            35                  40                  45

Leu Ile Tyr Gly Asn Arg Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Phe Asp Arg Gly
                85                  90                  95

Leu Ser Gly Ser Ile Val Phe Gly Gly Gly Thr Lys Leu Thr Val Leu
            100                 105                 110

Gly

<210> SEQ ID NO 89
<211> LENGTH: 14
<212> TYPE: PRT
<213> ORGANISM: Homo sapiens

<400> SEQUENCE: 89

Phe Ser Ser Asn Tyr Met Ser Trp Val Arg Gln Ala Pro Gly
1               5                   10

<210> SEQ ID NO 90
<211> LENGTH: 19
<212> TYPE: PRT
<213> ORGANISM: Homo sapiens

<400> SEQUENCE: 90
```

```
Ser Ser Ile Ser Ser Ser Ser Tyr Ile Tyr Tyr Ala Asp Ser Val
1               5                   10                  15

Lys Gly Arg

<210> SEQ ID NO 91
<211> LENGTH: 11
<212> TYPE: PRT
<213> ORGANISM: Homo sapiens

<400> SEQUENCE: 91

Ala Arg Asp Arg Gly Arg Thr Gly Thr Asp Tyr
1               5                   10

<210> SEQ ID NO 92
<211> LENGTH: 14
<212> TYPE: PRT
<213> ORGANISM: Homo sapiens

<400> SEQUENCE: 92

Cys Ser Gly Thr Thr Ser Asn Ile Gly Ser Tyr Ala Val Asn
1               5                   10

<210> SEQ ID NO 93
<211> LENGTH: 7
<212> TYPE: PRT
<213> ORGANISM: Homo sapiens

<400> SEQUENCE: 93

Gly Asn Ile Asn Arg Pro Ser
1               5

<210> SEQ ID NO 94
<211> LENGTH: 12
<212> TYPE: PRT
<213> ORGANISM: Homo sapiens

<400> SEQUENCE: 94

Cys Gln Ser Tyr Asp Ser Ser Leu Ser Ala Ser Leu
1               5                   10

<210> SEQ ID NO 95
<211> LENGTH: 118
<212> TYPE: PRT
<213> ORGANISM: Homo sapiens

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Arg Thr Gly Thr Asp Tyr Trp Gly Gln Gly Thr
            100                 105                 110

Leu Val Thr Val Ser Ser
```

<210> SEQ ID NO 96
<211> LENGTH: 111
<212> TYPE: PRT
<213> ORGANISM: Homo sapiens

<400> SEQUENCE: 96

Gln Ser Val Leu Thr Gln Pro Pro Ser Ala Ser Gly Thr Pro Gly Gln
1               5                   10                  15

Arg Val Thr Ile Ser Cys Ser Gly Thr Thr Ser Asn Ile Gly Ser Tyr
            20                  25                  30

Ala Val Asn Trp Tyr Gln Gln Leu Pro Gly Thr Ala Pro Lys Leu Leu
        35                  40                  45

Ile Tyr Gly Asn Ile Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Ala Ser Leu Phe Gly Gly Gly Thr Lys Leu Thr Val Leu Gly
            100                 105                 110

<210> SEQ ID NO 97
<211> LENGTH: 14
<212> TYPE: PRT
<213> ORGANISM: Homo sapiens

<400> SEQUENCE: 97

Phe Ser Ser Tyr Ala Met Ser Trp Val Arg Gln Ala Pro Gly
1               5                   10

<210> SEQ ID NO 98
<211> LENGTH: 19
<212> TYPE: PRT
<213> ORGANISM: Homo sapiens

<400> SEQUENCE: 98

Ser Thr Ile Ile Gly Ser Gly Ala Asn Thr Trp Tyr Ala Asp Ser Val
1               5                   10                  15

Lys Gly Arg

<210> SEQ ID NO 99
<211> LENGTH: 13
<212> TYPE: PRT
<213> ORGANISM: Homo sapiens

<400> SEQUENCE: 99

Ala Arg His Glu Gly Tyr Tyr Tyr Tyr Gly Met Asp Val
1               5                   10

<210> SEQ ID NO 100
<211> LENGTH: 15
<212> TYPE: PRT
<213> ORGANISM: Homo sapiens

<400> SEQUENCE: 100

Cys Thr Gly Ser Ser Ser Asn Ile Gly Ala Gly Tyr Val Val His
1               5                   10                  15

<210> SEQ ID NO 101

```
<211> LENGTH: 7
<212> TYPE: PRT
<213> ORGANISM: Homo sapiens

<400> SEQUENCE: 101

Gly Asn Ser Asn Arg Pro Ser
1               5

<210> SEQ ID NO 102
<211> LENGTH: 12
<212> TYPE: PRT
<213> ORGANISM: Homo sapiens

<400> SEQUENCE: 102

Cys Ala Ala Trp Asp Asp Ser Leu Asn Gly Arg Val
1               5                   10

<210> SEQ ID NO 103
<211> LENGTH: 120
<212> TYPE: PRT
<213> ORGANISM: Homo sapiens

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ile Gly Ser Gly Ala Asn Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Gly Tyr Tyr Tyr Gly Met Asp Val Trp Gly Gln
            100                 105                 110

Gly Thr Leu Val Thr Val Ser Ser
        115                 120

<210> SEQ ID NO 104
<211> LENGTH: 112
<212> TYPE: PRT
<213> ORGANISM: Homo sapiens

<400> SEQUENCE: 104

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Arg Val Phe Gly Gly Gly Thr Lys Leu Thr Val Leu Gly
```

```
                    100             105             110
```

<210> SEQ ID NO 105
<211> LENGTH: 14
<212> TYPE: PRT
<213> ORGANISM: Homo sapiens

<400> SEQUENCE: 105

Phe Asp Asp Tyr Gly Met Ser Trp Val Arg Gln Ala Pro Gly
1               5                   10

<210> SEQ ID NO 106
<211> LENGTH: 18
<212> TYPE: PRT
<213> ORGANISM: Homo sapiens

<400> SEQUENCE: 106

Ser Val Ile Tyr Ser Gly Gly Ser Thr Tyr Tyr Ala Asp Ser Val Lys
1               5                   10                  15

Gly Arg

<210> SEQ ID NO 107
<211> LENGTH: 16
<212> TYPE: PRT
<213> ORGANISM: Homo sapiens

<400> SEQUENCE: 107

Cys Ala Arg Asp Arg Ser Ser Ser Trp Tyr Arg Asp Gly Met Asp Val
1               5                   10                  15

<210> SEQ ID NO 108
<211> LENGTH: 15
<212> TYPE: PRT
<213> ORGANISM: Homo sapiens

<400> SEQUENCE: 108

Cys Thr Gly Ser Ser Ser Asn Ile Gly Ala Gly Tyr Asp Val His
1               5                   10                  15

<210> SEQ ID NO 109
<211> LENGTH: 7
<212> TYPE: PRT
<213> ORGANISM: Homo sapiens

<400> SEQUENCE: 109

Gly Asn Ser Asn Arg Pro Ser
1               5

<210> SEQ ID NO 110
<211> LENGTH: 12
<212> TYPE: PRT
<213> ORGANISM: Homo sapiens

<400> SEQUENCE: 110

Cys Ala Ala Trp Asp Asp Ser Leu Ser Gly Trp Val
1               5                   10

<210> SEQ ID NO 111
<211> LENGTH: 121
<212> TYPE: PRT
<213> ORGANISM: Homo sapiens

<400> SEQUENCE: 111

Glu Val Gln Leu Leu Glu Ser Gly Gly Gly Leu Val Gln Pro Gly Gly

```
                1               5                  10                  15
          Ser Leu Arg Leu Ser Cys Ala Ala Ser Gly Phe Thr Phe Asp Asp Tyr
                       20                  25                  30

Gly Met Ser Trp Val Arg Gln Ala Pro Gly Lys Gly Leu Glu Trp Val
                       35                  40                  45

Ser Val Ile Tyr Ser Gly Gly Ser Thr Tyr Tyr Ala Asp Ser Val Lys
                       50                  55                  60

Gly Arg Phe Thr Ile Ser Arg Asp Asn Ser Lys Asn Thr Leu Tyr Leu
           65                  70                  75                  80

Gln Met Asn Ser Leu Arg Ala Glu Asp Thr Ala Val Tyr Tyr Cys Ala
                       85                  90                  95

Arg Asp Arg Ser Ser Ser Trp Tyr Arg Asp Gly Met Asp Val Trp Gly
                       100                 105                 110

Gln Gly Thr Leu Val Thr Val Ser Ser
                       115                 120

<210> SEQ ID NO 112
<211> LENGTH: 112
<212> TYPE: PRT
<213> ORGANISM: Homo sapiens

<400> SEQUENCE: 112

Gln Ser Val Leu Thr Gln Pro Pro Ser Ala Ser Gly Thr Pro Gly Gln
           1               5                  10                  15

Arg Val Thr Ile Ser Cys Thr Gly Ser Ser Ser Asn Ile Gly Ala Gly
                       20                  25                  30

Tyr Asp Val His Trp Tyr Gln Gln Leu Pro Gly Thr Ala Pro Lys Leu
                       35                  40                  45

Leu Ile Tyr Gly Asn Ser Asn Arg Pro Ser Gly Val Pro Asp Arg Phe
                       50                  55                  60

Ser Gly Ser Lys Ser Gly Thr Ser Ala Ser Leu Ala Ile Ser Gly Leu
           65                  70                  75                  80

Arg Ser Glu Asp Glu Ala Asp Tyr Tyr Cys Ala Ala Trp Asp Asp Ser
                       85                  90                  95

Leu Ser Gly Trp Val Phe Gly Gly Gly Thr Lys Leu Thr Val Leu Gly
                       100                 105                 110

<210> SEQ ID NO 113
<211> LENGTH: 14
<212> TYPE: PRT
<213> ORGANISM: Homo sapiens

<400> SEQUENCE: 113

Phe Asp Asp Tyr Gly Met Ser Trp Val Arg Gln Ala Pro Gly
           1               5                  10

<210> SEQ ID NO 114
<211> LENGTH: 18
<212> TYPE: PRT
<213> ORGANISM: Homo sapiens

<400> SEQUENCE: 114

Ser Thr Ile Tyr Ser Gly Asp Asn Ala Tyr Tyr Gly Ala Ser Val Arg
           1               5                  10                  15

Gly Arg

<210> SEQ ID NO 115
<211> LENGTH: 15
```

```
<212> TYPE: PRT
<213> ORGANISM: Homo sapiens

<400> SEQUENCE: 115

Ala Arg Val Tyr Ser Ser Ser Trp Arg Lys Arg Ala Phe Asp Ile
1               5                   10                  15

<210> SEQ ID NO 116
<211> LENGTH: 14
<212> TYPE: PRT
<213> ORGANISM: Homo sapiens

<400> SEQUENCE: 116

Cys Ser Gly Thr Ser Ser Asn Ile Glu Ser Asn Thr Val Asn
1               5                   10

<210> SEQ ID NO 117
<211> LENGTH: 7
<212> TYPE: PRT
<213> ORGANISM: Homo sapiens

<400> SEQUENCE: 117

Ser Asp Asn Gln Arg Pro Ser
1               5

<210> SEQ ID NO 118
<211> LENGTH: 12
<212> TYPE: PRT
<213> ORGANISM: Homo sapiens

<400> SEQUENCE: 118

Cys Ala Ala Trp Asp Asp Ser Leu Ser Gly Trp Val
1               5                   10

<210> SEQ ID NO 119
<211> LENGTH: 121
<212> TYPE: PRT
<213> ORGANISM: Homo sapiens

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Thr Ile Tyr Ser Gly Asp Asn Ala Tyr Tyr Gly Ala Ser Val Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Tyr Ser Ser Ser Trp Arg Lys Arg Ala Phe Asp Ile Trp Gly
            100                 105                 110

Gln Gly Thr Leu Val Thr Val Ser Ser
        115                 120

<210> SEQ ID NO 120
<211> LENGTH: 111
<212> TYPE: PRT
<213> ORGANISM: Homo sapiens
```

<400> SEQUENCE: 120

Gln Ser Val Leu Thr Gln Pro Pro Ser Ala Ser Gly Thr Pro Gly Gln
1               5                   10                  15

Arg Val Thr Ile Ser Cys Ser Gly Thr Ser Ser Asn Ile Glu Ser Asn
            20                  25                  30

Thr Val Asn Trp Tyr Gln Gln Leu Pro Gly Thr Ala Pro Lys Leu Leu
        35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly
            100                 105                 110

<210> SEQ ID NO 121
<211> LENGTH: 14
<212> TYPE: PRT
<213> ORGANISM: Homo sapiens

<400> SEQUENCE: 121

Phe Ser Asp Tyr Tyr Met Ser Trp Ile Arg Gln Ala Pro Gly
1               5                   10

<210> SEQ ID NO 122
<211> LENGTH: 19
<212> TYPE: PRT
<213> ORGANISM: Homo sapiens

<400> SEQUENCE: 122

Ala Leu Ile Trp Tyr Asp Gly Gly Asn Glu Tyr Tyr Ala Asp Ser Val
1               5                   10                  15

Lys Gly Arg

<210> SEQ ID NO 123
<211> LENGTH: 11
<212> TYPE: PRT
<213> ORGANISM: Homo sapiens

<400> SEQUENCE: 123

Val Arg Glu Thr Gly Asn Tyr Gly Met Asp Val
1               5                   10

<210> SEQ ID NO 124
<211> LENGTH: 15
<212> TYPE: PRT
<213> ORGANISM: Homo sapiens

<400> SEQUENCE: 124

Cys Thr Gly Ser Ser Ser Asn Ile Gly Ala Gly Tyr Asp Val His
1               5                   10                  15

<210> SEQ ID NO 125
<211> LENGTH: 7
<212> TYPE: PRT
<213> ORGANISM: Homo sapiens

<400> SEQUENCE: 125

Arg Asn Asn Gln Arg Pro Ser
1               5

<210> SEQ ID NO 126
<211> LENGTH: 12
<212> TYPE: PRT
<213> ORGANISM: Homo sapiens

<400> SEQUENCE: 126

Cys Ala Thr Trp Asp Asp Arg Val Asn Gly Pro Val
1               5                   10

<210> SEQ ID NO 127
<211> LENGTH: 118
<212> TYPE: PRT
<213> ORGANISM: Homo sapiens

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ala Leu Ile Trp Tyr Asp Gly Gly Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Glu Thr Gly Asn Tyr Gly Met Asp Val Trp Gly Gln Gly Thr
            100                 105                 110

Leu Val Thr Val Ser Ser
        115

<210> SEQ ID NO 128
<211> LENGTH: 112
<212> TYPE: PRT
<213> ORGANISM: Homo sapiens

<400> SEQUENCE: 128

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Thr Trp Asp Asp Arg
                85                  90                  95

Val Asn Gly Pro Val Phe Gly Gly Gly Thr Lys Leu Thr Val Leu Gly
            100                 105                 110

<210> SEQ ID NO 129
<211> LENGTH: 14
<212> TYPE: PRT
<213> ORGANISM: Homo sapiens

```
<400> SEQUENCE: 129

Phe Ser Asp Tyr Tyr Met Ser Trp Ile Arg Gln Ala Pro Gly
1               5                   10

<210> SEQ ID NO 130
<211> LENGTH: 19
<212> TYPE: PRT
<213> ORGANISM: Homo sapiens

<400> SEQUENCE: 130

Ala Leu Ile Trp Tyr Asp Gly Gly Asn Glu Tyr Tyr Ala Asp Ser Val
1               5                   10                  15

Lys Gly Arg

<210> SEQ ID NO 131
<211> LENGTH: 11
<212> TYPE: PRT
<213> ORGANISM: Homo sapiens

<400> SEQUENCE: 131

Ala Arg Tyr Tyr Gly Asp Gly Gly Phe Asp Pro
1               5                   10

<210> SEQ ID NO 132
<211> LENGTH: 15
<212> TYPE: PRT
<213> ORGANISM: Homo sapiens

<400> SEQUENCE: 132

Cys Thr Gly Ser Ser Ser Asn Ile Gly Ala Gly Tyr Val Val His
1               5                   10                  15

<210> SEQ ID NO 133
<211> LENGTH: 7
<212> TYPE: PRT
<213> ORGANISM: Homo sapiens

<400> SEQUENCE: 133

Ser Asn Asn Gln Arg Pro Ser
1               5

<210> SEQ ID NO 134
<211> LENGTH: 12
<212> TYPE: PRT
<213> ORGANISM: Homo sapiens

<400> SEQUENCE: 134

Cys Ala Ala Trp Asp Asp Ser Leu Asn Gly Pro Val
1               5                   10

<210> SEQ ID NO 135
<211> LENGTH: 118
<212> TYPE: PRT
<213> ORGANISM: Homo sapiens

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45
```

Ala Ile Ile Ser Tyr Asp Gly Gly Lys Tyr Phe Ala Asp Pro Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Tyr Gly Asp Gly Phe Asp Pro Trp Gly Gln Gly Thr
            100                 105                 110

Leu Val Thr Val Ser Ser
            115

<210> SEQ ID NO 136
<211> LENGTH: 112
<212> TYPE: PRT
<213> ORGANISM: Homo sapiens

<400> SEQUENCE: 136

Gln Ser Val Leu Thr Gln Pro Pro Ser Ala Ser Gly Thr Pro Gly Gln
 1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Ser Asn Asn Gln Arg Pro Ser Gly Val Pro Asp Arg Phe
     50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Pro Val Phe Gly Gly Gly Thr Lys Leu Thr Val Leu Gly
            100                 105                 110

<210> SEQ ID NO 137
<211> LENGTH: 14
<212> TYPE: PRT
<213> ORGANISM: Homo sapiens

<400> SEQUENCE: 137

Phe Ser Ser Asn Tyr Met Ser Trp Val Arg Gln Ala Pro Gly
 1               5                   10

<210> SEQ ID NO 138
<211> LENGTH: 19
<212> TYPE: PRT
<213> ORGANISM: Homo sapiens

<400> SEQUENCE: 138

Ala Leu Ile Trp Tyr Asp Gly Ser Asn Lys Tyr Tyr Ala Asp Ser Val
 1               5                   10                  15

Lys Gly Arg

<210> SEQ ID NO 139
<211> LENGTH: 8
<212> TYPE: PRT
<213> ORGANISM: Homo sapiens

<400> SEQUENCE: 139

Ala Lys Asp Pro Leu Phe Asp Ser
 1               5

```
<210> SEQ ID NO 140
<211> LENGTH: 15
<212> TYPE: PRT
<213> ORGANISM: Homo sapiens

<400> SEQUENCE: 140

Cys Thr Gly Arg Ser Ser Asn Ile Gly Ala Gly Tyr Asp Val His
1               5                   10                  15

<210> SEQ ID NO 141
<211> LENGTH: 7
<212> TYPE: PRT
<213> ORGANISM: Homo sapiens

<400> SEQUENCE: 141

Asp Asn Asn Lys Arg Pro Ser
1               5

<210> SEQ ID NO 142
<211> LENGTH: 12
<212> TYPE: PRT
<213> ORGANISM: Homo sapiens

<400> SEQUENCE: 142

Cys Ala Ala Trp Asp Asp Ser Leu Asn Gly Pro Val
1               5                   10

<210> SEQ ID NO 143
<211> LENGTH: 115
<212> TYPE: PRT
<213> ORGANISM: Homo sapiens

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ala Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Pro Leu Phe Asp Ser Trp Gly Gln Gly Thr Leu Val Thr
            100                 105                 110

Val Ser Ser
        115

<210> SEQ ID NO 144
<211> LENGTH: 112
<212> TYPE: PRT
<213> ORGANISM: Homo sapiens

<400> SEQUENCE: 144

Gln Ser Val Leu Thr Gln Pro Pro Ser Ala Ser Gly Thr Pro Gly Gln
1               5                   10                  15

Arg Val Thr Ile Ser Cys Thr Gly Arg Ser Ser Asn Ile Gly Ala Gly
            20                  25                  30
```

```
Tyr Asp Val His Trp Tyr Gln Gln Leu Pro Gly Thr Ala Pro Lys Leu
            35                  40                  45

Leu Ile Tyr Asp Asn Asn Lys Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Ser
                 85                  90                  95

Leu Asn Gly Pro Val Phe Gly Gly Thr Lys Leu Thr Val Leu Gly
            100                 105                 110
```

<210> SEQ ID NO 145
<211> LENGTH: 14
<212> TYPE: PRT
<213> ORGANISM: Homo sapiens

<400> SEQUENCE: 145

```
Phe Asn Thr Tyr Ser Met Asn Trp Val Arg Gln Ala Pro Gly
 1               5                  10
```

<210> SEQ ID NO 146
<211> LENGTH: 18
<212> TYPE: PRT
<213> ORGANISM: Homo sapiens

<400> SEQUENCE: 146

```
Ser Val Leu Tyr Ser Asp Asp Thr His Tyr Ala Asp Ser Val Lys
 1               5                  10                  15

Gly Arg
```

<210> SEQ ID NO 147
<211> LENGTH: 17
<212> TYPE: PRT
<213> ORGANISM: Homo sapiens

<400> SEQUENCE: 147

```
Ala Arg Asp Cys Gly Gly Asp Cys His Ser Gly Asp Asp Ala Phe Asp
 1               5                  10                  15

Ile
```

<210> SEQ ID NO 148
<211> LENGTH: 14
<212> TYPE: PRT
<213> ORGANISM: Homo sapiens

<400> SEQUENCE: 148

```
Cys Ser Gly Ser Ser Ser Asn Ile Gly Ser Asn Thr Val Asn
 1               5                  10
```

<210> SEQ ID NO 149
<211> LENGTH: 7
<212> TYPE: PRT
<213> ORGANISM: Homo sapiens

<400> SEQUENCE: 149

```
Asp Asn Asp Lys Arg Pro Ser
 1               5
```

<210> SEQ ID NO 150
<211> LENGTH: 12
<212> TYPE: PRT
<213> ORGANISM: Homo sapiens

<400> SEQUENCE: 150

Cys Ala Ala Trp His Asp Ser Leu Asn Gly Trp Val
1               5                   10

<210> SEQ ID NO 151
<211> LENGTH: 123
<212> TYPE: PRT
<213> ORGANISM: Homo sapiens

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ser Met Asn Trp Val Arg Gln Ala Pro Gly Lys Gly Leu Glu Trp Val
        35                  40                  45

Ser Val Leu Tyr Ser Asp Asp Thr His Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Cys Gly Gly Asp Cys His Ser Gly Asp Ala Phe Asp Ile
            100                 105                 110

Trp Gly Gln Gly Thr Leu Val Thr Val Ser Ser
        115                 120

<210> SEQ ID NO 152
<211> LENGTH: 111
<212> TYPE: PRT
<213> ORGANISM: Homo sapiens

<400> SEQUENCE: 152

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Asp Asn Asp Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp His Asp Ser Leu
                85                  90                  95

Asn Gly Trp Val Leu Gly Gly Gly Thr Lys Leu Thr Val Leu Gly
            100                 105                 110

<210> SEQ ID NO 153
<211> LENGTH: 14
<212> TYPE: PRT
<213> ORGANISM: Homo sapiens

<400> SEQUENCE: 153

Phe Ser Ala Tyr Gly Met His Trp Val Arg Gln Ala Pro Gly
1               5                   10

```
<210> SEQ ID NO 154
<211> LENGTH: 19
<212> TYPE: PRT
<213> ORGANISM: Homo sapiens

<400> SEQUENCE: 154

Ala Val Val Ser Tyr Asp Gly Arg Glu Lys His Tyr Ala Asp Ser Val
1               5                   10                  15

Lys Gly Arg

<210> SEQ ID NO 155
<211> LENGTH: 14
<212> TYPE: PRT
<213> ORGANISM: Homo sapiens

<400> SEQUENCE: 155

Ala Arg Ser Asp Gly Gly Tyr Asp Ser Asp Ser Gly Tyr Tyr
1               5                   10

<210> SEQ ID NO 156
<211> LENGTH: 14
<212> TYPE: PRT
<213> ORGANISM: Homo sapiens

<400> SEQUENCE: 156

Cys Ser Gly Ser Thr Ser Asn Ile Gly Ser Asn Phe Val Tyr
1               5                   10

<210> SEQ ID NO 157
<211> LENGTH: 7
<212> TYPE: PRT
<213> ORGANISM: Homo sapiens

<400> SEQUENCE: 157

Asp Asn Asn Lys Arg Pro Ser
1               5

<210> SEQ ID NO 158
<211> LENGTH: 11
<212> TYPE: PRT
<213> ORGANISM: Homo sapiens

<400> SEQUENCE: 158

Cys Ser Ser Tyr Ala Tyr Ser Asp Asn Ile Leu
1               5                   10

<210> SEQ ID NO 159
<211> LENGTH: 121
<212> TYPE: PRT
<213> ORGANISM: Homo sapiens

<400> SEQUENCE: 159

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ala Tyr
                20                  25                  30

Gly Met His Trp Val Arg Gln Ala Pro Gly Lys Gly Leu Glu Trp Val
            35                  40                  45

Ala Val Val Ser Tyr Asp Gly Arg Glu Lys His Tyr Ala Asp Ser Val
        50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Ser Asp Gly Gly Tyr Asp Ser Asp Ser Gly Tyr Tyr Trp Gly
                100                 105                 110

Gln Gly Thr Leu Val Thr Val Ser Ser
            115                 120

<210> SEQ ID NO 160
<211> LENGTH: 110
<212> TYPE: PRT
<213> ORGANISM: Homo sapiens

<400> SEQUENCE: 160

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Ser Asn
            20                  25                  30

Phe Val Tyr Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ser Tyr Ala Tyr Ser Asp
                85                  90                  95

Asn Ile Leu Phe Gly Gly Gly Thr Lys Leu Thr Val Leu Gly
            100                 105                 110

<210> SEQ ID NO 161
<211> LENGTH: 14
<212> TYPE: PRT
<213> ORGANISM: Homo sapiens

<400> SEQUENCE: 161

Phe Ser Asn Ala Trp Met Ser Trp Val Arg Gln Ala Pro Gly
1               5                   10

<210> SEQ ID NO 162
<211> LENGTH: 19
<212> TYPE: PRT
<213> ORGANISM: Homo sapiens

<400> SEQUENCE: 162

Ser Gly Ile Ser Ser Ser Gly Ser Ala Tyr Tyr Ala Asp Ser Val
1               5                   10                  15

Lys Gly Arg

<210> SEQ ID NO 163
<211> LENGTH: 18
<212> TYPE: PRT
<213> ORGANISM: Homo sapiens

<400> SEQUENCE: 163

Ala Arg His Tyr Tyr His Ile Ala Gly Tyr Tyr Tyr Asp Thr Phe
1               5                   10                  15

Asp Ile

<210> SEQ ID NO 164
<211> LENGTH: 14
<212> TYPE: PRT
```

<213> ORGANISM: Homo sapiens

<400> SEQUENCE: 164

Cys Ser Gly Ser Ser Ser Asn Ile Gly Gly Asn Thr Val Asn
1               5                   10

<210> SEQ ID NO 165
<211> LENGTH: 7
<212> TYPE: PRT
<213> ORGANISM: Homo sapiens

<400> SEQUENCE: 165

Gly Asn Thr Asn Arg Pro Ser
1               5

<210> SEQ ID NO 166
<211> LENGTH: 12
<212> TYPE: PRT
<213> ORGANISM: Homo sapiens

<400> SEQUENCE: 166

Cys Ala Ala Trp Asp Asp Ser Leu Ser Gly Val Val
1               5                   10

<210> SEQ ID NO 167
<211> LENGTH: 125
<212> TYPE: PRT
<213> ORGANISM: Homo sapiens

<400> SEQUENCE: 167

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Gly Ile Ser Ser Ser Gly Ser Ser Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Tyr Tyr Tyr His Ile Ala Gly Tyr Tyr Tyr Asp Thr Phe
            100                 105                 110

Asp Ile Trp Gly Gln Gly Thr Leu Val Thr Val Ser Ser
        115                 120                 125

<210> SEQ ID NO 168
<211> LENGTH: 111
<212> TYPE: PRT
<213> ORGANISM: Homo sapiens

<400> SEQUENCE: 168

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Gly Asn
            20                  25                  30

Thr Val Asn Trp Tyr Gln Gln Leu Pro Gly Thr Ala Pro Lys Leu Leu
        35                  40                  45

Ile Tyr Gly Asn Thr Asn Arg Pro Ser Gly Val Pro Asp Arg Phe Ser

```
                    50                  55                  60
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Val Val Phe Gly Gly Gly Thr Lys Leu Thr Val Leu Gly
            100                 105                 110
```

<210> SEQ ID NO 169
<211> LENGTH: 14
<212> TYPE: PRT
<213> ORGANISM: Homo sapiens

<400> SEQUENCE: 169

```
Phe Ser Ser Tyr Ala Met Ser Trp Val Arg Gln Ala Pro Gly
 1               5                  10
```

<210> SEQ ID NO 170
<211> LENGTH: 19
<212> TYPE: PRT
<213> ORGANISM: Homo sapiens

<400> SEQUENCE: 170

```
Ala Thr Ile Ser Tyr His Gly Ser Asp Lys Asp Tyr Ala Asp Ser Val
 1               5                  10                  15

Lys Gly Arg
```

<210> SEQ ID NO 171
<211> LENGTH: 18
<212> TYPE: PRT
<213> ORGANISM: Homo sapiens

<400> SEQUENCE: 171

```
Ala Arg Asp Ala Asn Tyr His Ser Ser Gly Tyr Tyr Tyr Asp Val Phe
 1               5                  10                  15

Asp Ile
```

<210> SEQ ID NO 172
<211> LENGTH: 14
<212> TYPE: PRT
<213> ORGANISM: Homo sapiens

<400> SEQUENCE: 172

```
Cys Ser Gly Ser Ser Asn Ile Gly Ser Asn Thr Val Asn
 1               5                  10
```

<210> SEQ ID NO 173
<211> LENGTH: 7
<212> TYPE: PRT
<213> ORGANISM: Homo sapiens

<400> SEQUENCE: 173

```
Gly Asn Ser Asn Arg Pro Ser
 1               5
```

<210> SEQ ID NO 174
<211> LENGTH: 12
<212> TYPE: PRT
<213> ORGANISM: Homo sapiens

<400> SEQUENCE: 174

```
Cys Ala Ala Trp Asp Asp Ser Leu Ser Thr Trp Val
```

<210> SEQ ID NO 175
<211> LENGTH: 125
<212> TYPE: PRT
<213> ORGANISM: Homo sapiens

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Thr Ile Ser Tyr His Gly Ser Asp Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Asn Tyr His Ser Ser Gly Tyr Tyr Tyr Asp Val Phe
            100                 105                 110

Asp Ile Trp Gly Gln Gly Thr Leu Val Thr Val Ser Ser
        115                 120                 125

<210> SEQ ID NO 176
<211> LENGTH: 111
<212> TYPE: PRT
<213> ORGANISM: Homo sapiens

<400> SEQUENCE: 176

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Thr Trp Val Phe Gly Gly Gly Thr Lys Leu Thr Val Leu Gly
            100                 105                 110

<210> SEQ ID NO 177
<211> LENGTH: 14
<212> TYPE: PRT
<213> ORGANISM: Homo sapiens

<400> SEQUENCE: 177

Phe Ser Asp Tyr Tyr Met Thr Trp Ile Arg Gln Ala Pro Gly
1               5                   10

<210> SEQ ID NO 178
<211> LENGTH: 19
<212> TYPE: PRT
<213> ORGANISM: Homo sapiens

<400> SEQUENCE: 178

Ser Gly Ile Ser Gly Ser Gly Gly Tyr Ile His Tyr Ala Asp Ser Val
1               5                   10                  15

Lys Gly Arg

<210> SEQ ID NO 179
<211> LENGTH: 11
<212> TYPE: PRT
<213> ORGANISM: Homo sapiens

<400> SEQUENCE: 179

Ala Arg Glu Gly Leu Leu Pro Asp Ala Phe Asp
1               5                   10

<210> SEQ ID NO 180
<211> LENGTH: 14
<212> TYPE: PRT
<213> ORGANISM: Homo sapiens

<400> SEQUENCE: 180

Cys Ser Gly Ser Ser Ser Asn Ile Gly Asn Asn Tyr Val Ser
1               5                   10

<210> SEQ ID NO 181
<211> LENGTH: 7
<212> TYPE: PRT
<213> ORGANISM: Homo sapiens

<400> SEQUENCE: 181

Arg Asn Asn Gln Arg Pro Ser
1               5

<210> SEQ ID NO 182
<211> LENGTH: 12
<212> TYPE: PRT
<213> ORGANISM: Homo sapiens

<400> SEQUENCE: 182

Cys Ala Ala Trp Asp Asp Ser Val Ser Gly Trp Val
1               5                   10

<210> SEQ ID NO 183
<211> LENGTH: 119
<212> TYPE: PRT
<213> ORGANISM: Homo sapiens

<400> SEQUENCE: 183

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Val
        35                  40                  45

Ser Gly Ile Ser Gly Ser Gly Gly Tyr Ile His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Leu Pro Asp Ala Phe Asp Ile Trp Gly Gln Gly

```
                100             105             110
Thr Leu Val Thr Val Ser Ser
            115

<210> SEQ ID NO 184
<211> LENGTH: 111
<212> TYPE: PRT
<213> ORGANISM: Homo sapiens

<400> SEQUENCE: 184

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Val
                85                  90                  95

Ser Gly Trp Val Phe Gly Gly Gly Thr Lys Leu Thr Val Leu Gly
            100                 105                 110

<210> SEQ ID NO 185
<211> LENGTH: 14
<212> TYPE: PRT
<213> ORGANISM: Homo sapiens

<400> SEQUENCE: 185

Phe Ser Ser Tyr Ser Met Asn Trp Val Arg Gln Ala Pro Gly
1               5                   10

<210> SEQ ID NO 186
<211> LENGTH: 19
<212> TYPE: PRT
<213> ORGANISM: Homo sapiens

<400> SEQUENCE: 186

Ala Val Met Ser Tyr Asp Glu Tyr Asn Thr Tyr Ala Asp Ser Val
1               5                   10                  15

Lys Gly Arg

<210> SEQ ID NO 187
<211> LENGTH: 13
<212> TYPE: PRT
<213> ORGANISM: Homo sapiens

<400> SEQUENCE: 187

Ala Lys Gly Phe Tyr Gly Asp Tyr Pro Leu Trp Asp Tyr
1               5                   10

<210> SEQ ID NO 188
<211> LENGTH: 14
<212> TYPE: PRT
<213> ORGANISM: Homo sapiens

<400> SEQUENCE: 188

Cys Ser Gly Gly Asn Ser Asn Ile Gly Thr Asn Thr Val Asp
1               5                   10
```

<210> SEQ ID NO 189
<211> LENGTH: 7
<212> TYPE: PRT
<213> ORGANISM: Homo sapiens

<400> SEQUENCE: 189

Ser Asn Asn Gln Arg Pro Ser
1               5

<210> SEQ ID NO 190
<211> LENGTH: 12
<212> TYPE: PRT
<213> ORGANISM: Homo sapiens

<400> SEQUENCE: 190

Cys Ala Ala Trp Asp Asp Ser Val Asn Gly Pro Val
1               5                   10

<210> SEQ ID NO 191
<211> LENGTH: 120
<212> TYPE: PRT
<213> ORGANISM: Homo sapiens

<400> SEQUENCE: 191

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Val Met Ser Tyr Asp Glu Tyr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Phe Tyr Gly Asp Tyr Pro Leu Trp Asp Tyr Trp Gly Gln
            100                 105                 110

Gly Thr Leu Val Thr Val Ser Ser
        115                 120

<210> SEQ ID NO 192
<211> LENGTH: 111
<212> TYPE: PRT
<213> ORGANISM: Homo sapiens

<400> SEQUENCE: 192

Gln Ser Val Leu Thr Gln Pro Pro Ser Ala Ser Gly Thr Pro Gly Gln
1               5                   10                  15

Arg Val Thr Ile Ser Cys Ser Gly Gly Asn Ser Asn Ile Gly Thr Asn
            20                  25                  30

Thr Val Asp Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Val 85                  90                  95
Asn Gly Pro Val Phe Gly Gly Gly Thr Lys Leu Thr Val Leu Gly
            100                 105                 110

<210> SEQ ID NO 193
<211> LENGTH: 14
<212> TYPE: PRT
<213> ORGANISM: Homo sapiens

<400> SEQUENCE: 193

Phe Ser Ser Tyr Glu Met Asn Trp Val Arg Gln Ala Pro Gly
1               5                   10

<210> SEQ ID NO 194
<211> LENGTH: 18
<212> TYPE: PRT
<213> ORGANISM: Homo sapiens

<400> SEQUENCE: 194

Ser Thr Ile Thr Gly Gly Gly Ser Ile Tyr Asp Ala Asn Ser Val Gln
1               5                   10                  15

Gly Arg

<210> SEQ ID NO 195
<211> LENGTH: 18
<212> TYPE: PRT
<213> ORGANISM: Homo sapiens

<400> SEQUENCE: 195

Ala Arg Asp Ser Thr Tyr His Ser Ser Gly Tyr Tyr Tyr Asp Val Phe
1               5                   10                  15

Asp Ile

<210> SEQ ID NO 196
<211> LENGTH: 14
<212> TYPE: PRT
<213> ORGANISM: Homo sapiens

<400> SEQUENCE: 196

Cys Ser Gly Ser Ser Ser Asn Ile Gly Ser Asn Thr Val Asn
1               5                   10

<210> SEQ ID NO 197
<211> LENGTH: 7
<212> TYPE: PRT
<213> ORGANISM: Homo sapiens

<400> SEQUENCE: 197

Gly Asn Ser Asn Arg Pro Ser
1               5

<210> SEQ ID NO 198
<211> LENGTH: 13
<212> TYPE: PRT
<213> ORGANISM: Homo sapiens

<400> SEQUENCE: 198

Cys Ala Ala Trp Asp Asp Ser Leu Ser Gly His Trp Val
1               5                   10

<210> SEQ ID NO 199
<211> LENGTH: 124
<212> TYPE: PRT

-continued

<213> ORGANISM: Homo sapiens

<400> SEQUENCE: 199

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Thr Ile Thr Gly Gly Ser Ile Tyr Asp Ala Asn Ser Val Gln
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ser Thr Tyr His Ser Ser Gly Tyr Tyr Tyr Asp Val Phe Asp
            100                 105                 110

Ile Trp Gly Gln Gly Thr Leu Val Thr Val Ser Ser
            115                 120

<210> SEQ ID NO 200
<211> LENGTH: 112
<212> TYPE: PRT
<213> ORGANISM: Homo sapiens

<400> SEQUENCE: 200

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly His Trp Val Phe Gly Gly Gly Thr Lys Leu Thr Val Leu Gly
            100                 105                 110

<210> SEQ ID NO 201
<211> LENGTH: 14
<212> TYPE: PRT
<213> ORGANISM: Homo sapiens

<400> SEQUENCE: 201

Phe Ser Ser Tyr Gly Met His Trp Val Arg Gln Ala Pro Gly
1               5                   10

<210> SEQ ID NO 202
<211> LENGTH: 20
<212> TYPE: PRT
<213> ORGANISM: Homo sapiens

<400> SEQUENCE: 202

Ser Ala Val Phe Gly Ser Gly His Gly Asn Thr Phe Tyr Ala Asp Ala
1               5                   10                  15

```
Val Lys Gly Arg
            20
```

<210> SEQ ID NO 203
<211> LENGTH: 14
<212> TYPE: PRT
<213> ORGANISM: Homo sapiens

<400> SEQUENCE: 203

```
Ala Arg Glu Gln Leu Trp Phe Gly Gln Asp Ala Phe Asp Ile
1               5                   10
```

<210> SEQ ID NO 204
<211> LENGTH: 14
<212> TYPE: PRT
<213> ORGANISM: Homo sapiens

<400> SEQUENCE: 204

```
Cys Ser Gly Ser Ser Ser Asn Ile Gly Ser Asn Thr Val Asn
1               5                   10
```

<210> SEQ ID NO 205
<211> LENGTH: 7
<212> TYPE: PRT
<213> ORGANISM: Homo sapiens

<400> SEQUENCE: 205

```
Gly Asn Ser Asn Arg Pro Ser
1               5
```

<210> SEQ ID NO 206
<211> LENGTH: 12
<212> TYPE: PRT
<213> ORGANISM: Homo sapiens

<400> SEQUENCE: 206

```
Cys Gln Ser Tyr Asp Ser Ser Leu Ser Ala Ser Val
1               5                   10
```

<210> SEQ ID NO 207
<211> LENGTH: 122
<212> TYPE: PRT
<213> ORGANISM: Homo sapiens

<400> SEQUENCE: 207

```
Glu Val Gln Leu Leu Glu Ser Gly Gly Gly Leu Val Gln Pro Gly Gly
1               5                   10                  15

Pro Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Val Phe Gly Ser Gly His Gly Asn Thr Phe Tyr Ala Asp Ala
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Glu Gln Leu Trp Phe Gly Gln Asp Ala Phe Asp Ile Trp
            100                 105                 110

Gly Gln Gly Thr Leu Val Thr Val Ser Ser
        115                 120
```

<210> SEQ ID NO 208
<211> LENGTH: 111
<212> TYPE: PRT
<213> ORGANISM: Homo sapiens

<400> SEQUENCE: 208

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Ala Ser Val Phe Gly Gly Gly Thr Lys Leu Thr Val Leu Gly
            100                 105                 110

<210> SEQ ID NO 209
<211> LENGTH: 14
<212> TYPE: PRT
<213> ORGANISM: Homo sapiens

<400> SEQUENCE: 209

Phe Ser Asp Ala Trp Met Thr Trp Val Arg Gln Ala Pro Gly
1               5                   10

<210> SEQ ID NO 210
<211> LENGTH: 19
<212> TYPE: PRT
<213> ORGANISM: Homo sapiens

<400> SEQUENCE: 210

Ser Asp Leu Ser Asp Ser Gly Gly Ser Thr Tyr Tyr Ala Asp Ser Val
1               5                   10                  15

Lys Gly Arg

<210> SEQ ID NO 211
<211> LENGTH: 11
<212> TYPE: PRT
<213> ORGANISM: Homo sapiens

<400> SEQUENCE: 211

Gly Arg Leu Ala Ala Gly Gly Pro Val Asp Tyr
1               5                   10

<210> SEQ ID NO 212
<211> LENGTH: 15
<212> TYPE: PRT
<213> ORGANISM: Homo sapiens

<400> SEQUENCE: 212

Cys Thr Gly Ser Ser Ser Asn Ile Gly Ala Gly Tyr Asp Val His
1               5                   10                  15

<210> SEQ ID NO 213
<211> LENGTH: 7
<212> TYPE: PRT

-continued

<213> ORGANISM: Homo sapiens

<400> SEQUENCE: 213

Ser Asn Asn Gln Arg Pro Ser
1               5

<210> SEQ ID NO 214
<211> LENGTH: 12
<212> TYPE: PRT
<213> ORGANISM: Homo sapiens

<400> SEQUENCE: 214

Cys Ser Val Trp Asp Asp Ser Leu Asn Ser Trp Val
1               5                   10

<210> SEQ ID NO 215
<211> LENGTH: 118
<212> TYPE: PRT
<213> ORGANISM: Homo sapiens

<400> SEQUENCE: 215

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Thr Trp Val Arg Gln Ala Pro Gly Lys Gly Leu Glu Trp Val
        35                  40                  45

Ser Asp Leu Ser Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg Leu Ala Ala Gly Gly Pro Val Asp Tyr Trp Gly Gln Gly Thr
            100                 105                 110

Leu Val Thr Val Ser Ser
        115

<210> SEQ ID NO 216
<211> LENGTH: 112
<212> TYPE: PRT
<213> ORGANISM: Homo sapiens

<400> SEQUENCE: 216

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ser Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ser Val Trp Asp Asp Ser
                85                  90                  95

Leu Asn Ser Trp Val Phe Gly Gly Gly Thr Lys Leu Thr Val Leu Gly
            100                 105                 110

<210> SEQ ID NO 217
<211> LENGTH: 330
<212> TYPE: PRT
<213> ORGANISM: Homo sapiens

<400> SEQUENCE: 217

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 218
<211> LENGTH: 105
<212> TYPE: PRT
<213> ORGANISM: Homo sapiens

<400> SEQUENCE: 218

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
                100                 105

<210> SEQ ID NO 219
<211> LENGTH: 330
<212> TYPE: PRT
<213> ORGANISM: Mus musculus

<400> SEQUENCE: 219

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
                100                 105                 110

Pro Ala Pro Asn Leu Leu Gly Gly Pro Ser Val Phe Ile Phe Pro Pro
            115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270
```

```
Asn Tyr Lys Asn Thr Glu Pro Val Leu Asp Ser Asp Gly Ser Tyr Phe
            275                 280                 285
Met Tyr Ser Lys Leu Arg Val Glu Lys Lys Asn Trp Val Glu Arg Asn
        290                 295                 300
Ser Tyr Ser Cys Ser Val Val His Glu Gly Leu His Asn His His Thr
305                 310                 315                 320
Thr Lys Ser Phe Ser Arg Thr Pro Gly Lys
            325                 330

<210> SEQ ID NO 220
<211> LENGTH: 330
<212> TYPE: PRT
<213> ORGANISM: Mus musculus

<400> SEQUENCE: 220

Ala Lys Thr Thr Ala Pro Ser Val Tyr Pro Leu Ala Pro Val Cys Gly
1               5                   10                  15
Asp Thr Thr Gly Ser Ser Val Thr Leu Gly Cys Leu Val Lys Gly Tyr
            20                  25                  30
Phe Pro Glu Pro Val Thr Leu Thr Trp Asn Ser Gly Ser Leu Ser Ser
        35                  40                  45
Gly Val His Thr Phe Pro Ala Val Leu Gln Ser Asp Leu Tyr Thr Leu
    50                  55                  60
Ser Ser Ser Val Thr Val Thr Ser Ser Thr Trp Pro Ser Gln Ser Ile
65                  70                  75                  80
Thr Cys Asn Val Ala His Pro Ala Ser Ser Thr Lys Val Asp Lys Lys
                85                  90                  95
Ile Glu Pro Arg Gly Pro Thr Ile Lys Pro Cys Pro Pro Cys Lys Cys
            100                 105                 110
Pro Ala Pro Asn Leu Leu Gly Gly Pro Ser Val Phe Ile Phe Pro Pro
        115                 120                 125
Lys Ile Lys Asp Val Leu Met Ile Ser Leu Ser Pro Ile Val Thr Cys
    130                 135                 140
Val Val Val Asp Val Ser Glu Asp Asp Pro Asp Val Gln Ile Ser Trp
145                 150                 155                 160
Phe Val Asn Asn Val Glu Val His Thr Ala Gln Thr Gln Thr His Arg
                165                 170                 175
Glu Asp Tyr Ala Ser Thr Leu Arg Val Val Ser Ala Leu Pro Ile Gln
            180                 185                 190
His Gln Asp Trp Met Ser Gly Lys Glu Phe Lys Cys Lys Val Asn Asn
        195                 200                 205
Lys Asp Leu Pro Ala Pro Ile Glu Arg Thr Ile Ser Lys Pro Lys Gly
    210                 215                 220
Ser Val Arg Ala Pro Gln Val Tyr Val Leu Pro Pro Pro Glu Glu Glu
225                 230                 235                 240
Met Thr Lys Lys Gln Val Thr Leu Thr Cys Met Val Thr Asp Phe Met
                245                 250                 255
Pro Glu Asp Ile Tyr Val Glu Trp Thr Asn Asn Gly Lys Thr Glu Leu
            260                 265                 270
Asn Tyr Lys Asn Thr Glu Pro Val Leu Asp Ser Asp Gly Ser Tyr Phe
        275                 280                 285
Met Tyr Ser Lys Leu Arg Val Glu Lys Lys Asn Trp Val Glu Arg Asn
    290                 295                 300
Ser Tyr Ser Cys Ser Val Val His Glu Gly Leu His Asn His His Thr
```

```
                305                 310                 315                 320
Thr Lys Ser Phe Ser Arg Thr Pro Gly Lys
                325                 330

<210> SEQ ID NO 221
<211> LENGTH: 105
<212> TYPE: PRT
<213> ORGANISM: Mus musculus

<400> SEQUENCE: 221

Gln Pro Lys Ser Ser Pro Ser Val Thr Leu Phe Pro Pro Ser Ser Glu
1               5                   10                  15

Glu Leu Glu Thr Asn Lys Ala Thr Leu Val Cys Thr Ile Thr Asp Phe
            20                  25                  30

Tyr Pro Gly Val Val Thr Val Asp Trp Lys Val Asp Gly Thr Pro Val
        35                  40                  45

Thr Gln Gly Met Glu Thr Thr Gln Pro Ser Lys Gln Ser Asn Asn Lys
    50                  55                  60

Tyr Met Ala Ser Ser Tyr Leu Thr Leu Thr Ala Arg Ala Trp Glu Arg
65                  70                  75                  80

His Ser Ser Tyr Ser Cys Gln Val Thr His Glu Gly His Thr Val Glu
                85                  90                  95

Lys Ser Leu Ser Arg Ala Asp Cys Ser
            100                 105

<210> SEQ ID NO 222
<211> LENGTH: 1356
<212> TYPE: DNA
<213> ORGANISM: Homo sapiens

<400> SEQUENCE: 222
gaggtgcagc tgttggagtc tgggggaggc ttggtacagc ctggggggtc cctgagactc      60
tcctgtgcag cctctggatt cacctttgat gattatggca tgagctgggt ccgccaagct     120
ccagggaagg ggctggagtg ggtctcagtt atttatagcg gtggtagtac atattacgca     180
gactccgtga agggccgatt caccatctcc agagacaatt ccaagaacac gctgtatctg     240
caaatgaaca gcctgagagc cgaggacact gccgtgtatt actgtgcgag agatcgaagc     300
agcagctggt accgcgatgg tatggacgtc tggggccaag gtacactggt caccgtgagc     360
tcagcctcca ccaagggccc atcggtcttc ccctggcac cctcctccaa gagcacctct      420
gggggcacag cggccctggg ctgcctggtc aaggactact cccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gaaagttgag     660
cccaaatctt gtgacaaaac tcacacatgc ccaccgtgcc cagcacctga actcctgggg     720
ggaccgtcag tcttcctctt ccccccaaaa cccaaggaca cctcatgat ctcccggacc      780 cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccctcccag cccccatcga gaaaaccatc    1020
tccaaagcca aagggcagcc ccgagaacca caggtgtaca ccctgccccc atcccgggat    1080
gagctgacca agaaccaggt cagcctgacc tgcctggtca aaggcttcta tcccagcgac    1140
```

```
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaatga                              1356

<210> SEQ ID NO 223
<211> LENGTH: 654
<212> TYPE: DNA
<213> ORGANISM: Homo sapiens

<400> SEQUENCE: 223
cagtctgtgc tgactcagcc accctcagcg tctgggaccc ccgggcagag ggtcaccatc      60
tcctgcactg ggagcagctc caacatcggg gcaggttatg atgtacactg gtatcagcag     120
ctcccaggaa cggcccccaa actcctcatc tatggtaaca gcaatcggcc ctcagggtc      180 cctgaccgat tctctggctc caagtctggc acctcagcct ccctggccat cagtgggctc     240
cggtccgagg atgaggctga ttattactgt gcagcatggg atgacagcct gagtggttgg     300
gtgttcggcg gaggaaccaa gctgacggtc ctaggtcagc ccaaggctgc cccctcggtc     360
actctgttcc cgccctcctc tgaggagctt caagccaaca ggccacact ggtgtgtctc      420 ataagtgact ctacccggg agccgtgaca gtggcctgga aggcagatag cagccccgtc     480
aaggcgggag tggagaccac cacaccctcc aaacaaagca caacaagta cgcggccagc     540 agctatctga gcctgacgcc tgagcagtgg aagtcccaca gaagctacag ctgccaggtc     600
acgcatgaag ggagcaccgt ggagaagaca gtggccccta cagaatgttc atga          654

<210> SEQ ID NO 224
<211> LENGTH: 5
<212> TYPE: PRT
<213> ORGANISM: Homo sapiens

<400> SEQUENCE: 224

Lys Cys Ser Pro Gly
1               5

<210> SEQ ID NO 225
<211> LENGTH: 5
<212> TYPE: PRT
<213> ORGANISM: Homo sapiens

<400> SEQUENCE: 225

Lys Cys Arg Pro Gly
1               5
```